(12) United States Patent
Medin et al.

(10) Patent No.: US 11,597,917 B2
(45) Date of Patent: Mar. 7, 2023

(54) IN VITRO AND IN VIVO ENRICHMENT STRATEGY TARGETING LYMPHOCYTES DERIVED FROM VECTOR TRANSDUCED HSCS FOR THERAPY OF DISORDERS

(71) Applicants: THE MEDICAL COLLEGE OF WISCONSIN, INC., Milwaukee, WI (US); UNIVERSITY HEALTH NETWORK, Toronto (CA); WASHINGTON UNIVERSITY IN ST. LOUIS, St. Louis, MO (US)

(72) Inventors: Jeffrey A. Medin, Shorewood, WI (US); John F. Dipersio, St. Louis, MO (US); Murtaza S. Nagree, Milwaukee, WI (US)

(73) Assignees: The Medical College of Wisconsin, Inc., Milwaukee, WI (US); University Health Network, Toronto (CA); Washington University in St. Louis, St. Louis, MO (US)

(*) Notice: Subject to any disclaimer, the term of this patent is extended or adjusted under 35 U.S.C. 154(b) by 415 days.

(21) Appl. No.: 16/619,883

(22) PCT Filed: Jun. 6, 2018

(86) PCT No.: PCT/US2018/036292
§ 371 (c)(1),
(2) Date: Dec. 5, 2019

(87) PCT Pub. No.: WO2019/009979
PCT Pub. Date: Jan. 10, 2019

(65) Prior Publication Data
US 2020/0181582 A1    Jun. 11, 2020

Related U.S. Application Data

(60) Provisional application No. 62/664,671, filed on Apr. 30, 2018, provisional application No. 62/516,022, filed on Jun. 6, 2017.

(51) Int. Cl.
| | |
|---|---|
| *C12N 9/04* | (2006.01) |
| *A61P 43/00* | (2006.01) |
| *A61K 9/00* | (2006.01) |
| *A61K 35/28* | (2015.01) |
| *C12N 5/0789* | (2010.01) |
| *C12N 7/00* | (2006.01) |
| *C12N 9/40* | (2006.01) |
| *C12N 9/24* | (2006.01) |
| *C12N 9/80* | (2006.01) |
| *C12N 15/86* | (2006.01) |

(52) U.S. Cl.
CPC .......... *C12N 9/0006* (2013.01); *A61K 9/0019* (2013.01); *A61K 35/28* (2013.01); *A61P 43/00* (2018.01); *C12N 5/0647* (2013.01); *C12N 7/00* (2013.01); *C12N 9/2465* (2013.01); *C12N 9/2477* (2013.01); *C12N 9/80* (2013.01); *C12N 15/86* (2013.01); *C12Y 101/01205* (2013.01); *C12Y 302/0102* (2013.01); *C12Y 302/01022* (2013.01); *C12Y 302/01045* (2013.01); *C12Y 305/01023* (2013.01); *C12N 2510/02* (2013.01); *C12N 2740/15043* (2013.01)

(58) Field of Classification Search
CPC ...... C12N 9/0006; C12N 5/0647; C12N 7/00; C12N 9/2465; C12N 9/2477; C12N 9/80; C12N 15/86; C12N 2510/02; C12N 2740/15043; C12N 2740/16043; C12N 2830/205; A61K 9/0019; A61K 35/28; A61K 48/005; A61P 43/00; C12Y 101/01205; C12Y 302/0102; C12Y 302/01022; C12Y 302/01045; C12Y 305/01023

See application file for complete search history.

(56) References Cited

U.S. PATENT DOCUMENTS

| | | | |
|---|---|---|---|
| 6,013,516 | A | 1/2000 | Verma |
| 6,207,455 | B1 | 3/2001 | Chang |
| 6,235,522 | B1 | 5/2001 | Kingsman |
| 6,277,633 | B1 | 8/2001 | Olsen |
| 6,326,007 | B1 | 12/2001 | Yilma |
| 6,627,442 | B1 | 9/2003 | Humeau |
| 7,575,924 | B2 | 8/2009 | Trono |
| 7,968,332 | B2 | 6/2011 | Charneau |
| 8,329,462 | B2 | 12/2012 | Trono |
| 8,349,606 | B2 | 1/2013 | Charneau |
| 8,551,773 | B2 | 10/2013 | Trono |

(Continued)

FOREIGN PATENT DOCUMENTS

| | | | | |
|---|---|---|---|---|
| EP | 3293259 | A1 * | 3/2018 | ............ A61K 38/47 |
| WO | 1999004026 | A2 | 1/1999 | |

(Continued)

OTHER PUBLICATIONS

Yu X et al. Lentiviral Vectors with Two Independent Internal Promoters Transfer High-Level Expression of Multiple Transgenes to Human Hematopoietic Stem-Progenitor Cells. 2003. Molecular Therapy. vol. 7, No. 6. p. 827-838 (Year: 2003).*

(Continued)

Primary Examiner — Paul J Holland
(74) Attorney, Agent, or Firm — Quarles & Brady LLP

(57) ABSTRACT

The present invention is related to a dual promoter lentiviral vector and methods of use for the treatment of diseases and disorders, specifically lysosomal storage disorders.

26 Claims, 17 Drawing Sheets
Specification includes a Sequence Listing.

(56) References Cited

U.S. PATENT DOCUMENTS

| | | | |
|---|---|---|---|
| 8,652,807 | B2 | 2/2014 | Charneau |
| 9,023,646 | B2 | 5/2015 | Trono |
| 9,476,062 | B2 | 10/2016 | Trono |
| 2002/0123471 | A1 | 9/2002 | Uberla |
| 2014/0010861 | A1 | 1/2014 | Bancel et al. |
| 2016/0296563 | A1 | 10/2016 | Sourdive et al. |

FOREIGN PATENT DOCUMENTS

| | | | | |
|---|---|---|---|---|
| WO | 2001034843 A1 | | 5/2001 | |
| WO | WO-2009114942 A1 | * | 9/2009 | ......... A61K 48/0058 |
| WO | WO-2016183593 A2 | * | 11/2016 | |
| WO | WO-2018132667 A1 | * | 7/2018 | ............. A61K 38/50 |

OTHER PUBLICATIONS

Kim EY et al. Long-term expression of the human glucocerebrosidase gene in vivo after transplantation of bone-marrow-derived cells transformed with a lentivirus vector. 2005. J. Gene Med. 7:878-887. (Year: 2005).*

Singh RK et al. Protein Engineering Approaches in the Post-Genomic Era. 2017. Current Protein and Peptide Science. 18, 1-11. (Year: 2017).*

Zhang M et al. Propagated Perturbations from a Peripheral Mutation Show Interactions Supporting WW Domain Thermostability. 2018. Structure. 26, 1474-1485. (Year: 2018).*

Brady, R. O., et al. "Enzymatic defect in Fabry's disease: ceramidetrihexosidase deficiency." New England Journal of Medicine 276.21 (1967): 1163-1167.

Brady, R. O., et al. "Replacement therapy for inherited enzyme deficiency: use of purified ceramidetrihexosidase in Fabry's disease." New England Journal of Medicine 289.1 (1973): 9-14.

International Searching Authority, International Search Report & Written Opinion for application PCT/US2018/036292, dated Sep. 18, 2018.

Medin, J. A., et al. "Correction in trans for Fabry disease: expression, secretion and uptake of alpha-galactosidase A in patient-derived cells driven by a high-titer recombinant retroviral vector." Proceedings of the National Academy of Sciences 93.15 (1996): 7917-7922.

Nagree, M. S., et al. "Towards in vivo amplification: Overcoming hurdles in the use of hematopoietic stem cells in transplantation and gene therapy." World journal of stem cells 7.11 (2015): 1233.

Naldini, L., et al. "In vivo gene delivery and stable transduction of nondividing cells by a lentiviral vector." Science 272.5259 (1996): 263-267.

Sangiolo, D., et al. "Lentiviral vector conferring resistance to mycophenolate mofetil and sensitivity to ganciclovir for in vivo T-cell selection." Gene therapy 14.21 (2007): 1549-1554.

Shi, Q., et al. "Lentivirus-mediated platelet-derived factor VIII gene therapy in murine haemophilia A." Journal of Thrombosis and Haemostasis 5.2 (2007): 352-361.

Yam, P., et al. "Ex vivo selection and expansion of cells based on expression of a mutated inosine monophosphate dehydrogenase 2 after HIV vector transduction: effects on lymphocytes, monocytes, and CD34+ stem cells." Molecular Therapy 14.2 (2006): 236-244.

Zufferey, R., et al. "Multiply attenuated lentiviral vector achieves efficient gene delivery in vivo." Nature biotechnology 15.9 (1997): 871-875.

* cited by examiner

Figure 4C-F
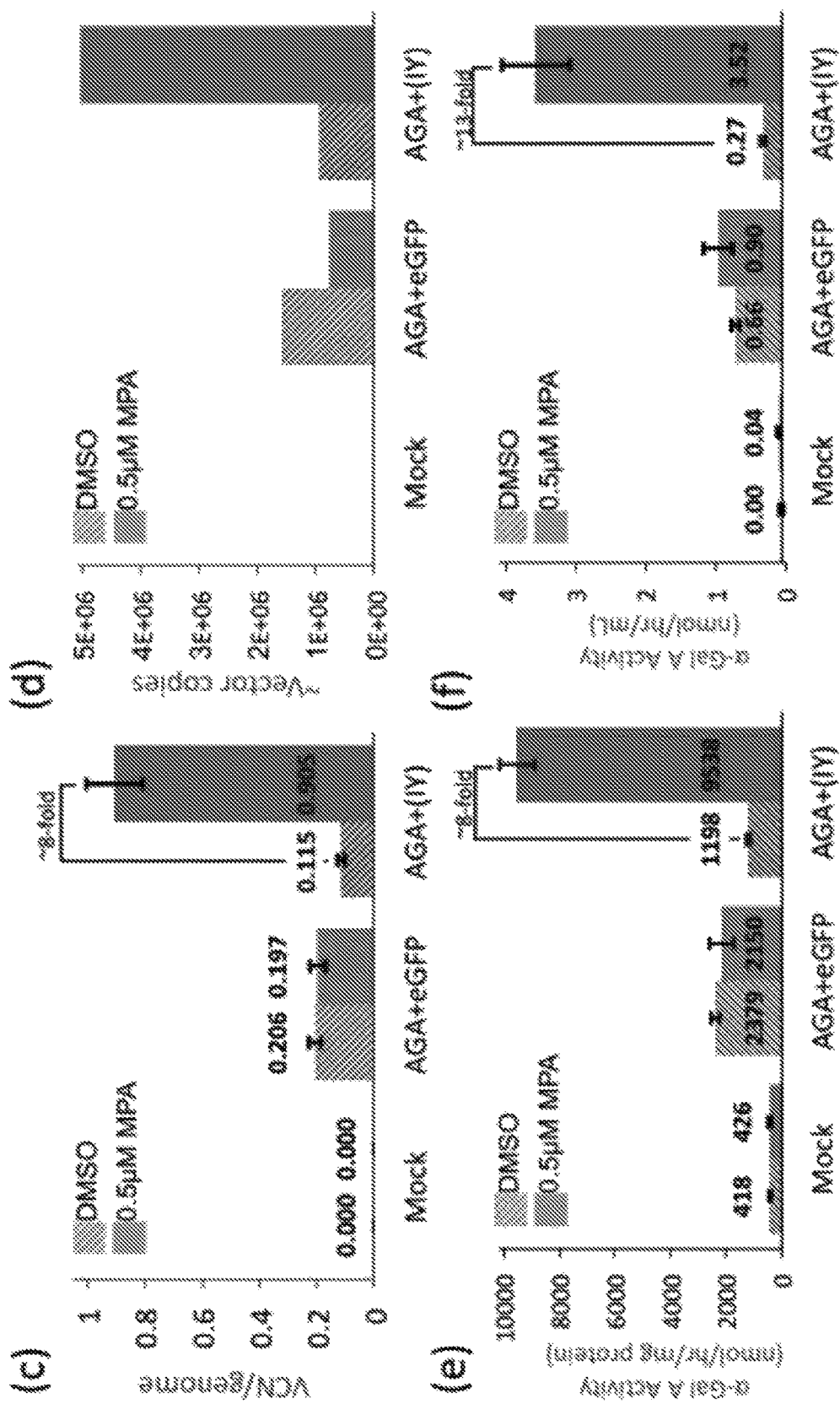

SEQUENCE LISTING

<160> NUMBER OF SEQ ID NOS: 12

<210> SEQ ID NO 1
<211> LENGTH: 8523
<212> TYPE: DNA
<213> ORGANISM: Artificial Sequence
<220> FEATURE:
<223> OTHER INFORMATION: synthetic vector

<400> SEQUENCE: 1

```
aaattgtaag cgttaatatt ttgttaaaat tcgcgttaaa ttttgttaa atcagctcat      60 tttttaacca ataggccgaa atcggcaaaa tcccttataa atcaaaagaa tagaccgaga    120
tagggttgag tgttgttcca gtttggaaca agagtccact attaaagaac gtggactcca   180
acgtcaaagg gcgaaaaacc gtctatcagg gcgatggccc actacgtgaa ccatcaccct   240
aatcaagttt tttggggtcg aggtgccgta agcactaaa tcggaaccct aaagggagcc    300
cccgatttag agcttgacgg ggaaagccgg cgaacgtggc gagaaaggaa gggaagaaag   360
cgaaaggagc gggcgctagg gcgctggcaa gtgtagcggt cacgctgcgc gtaaccacca   420
cacccgccgc gcttaatgcg ccgctacagg gcgcgtccat tcgccattca ggctgcgcaa   480
ctgttgggaa gggcgatcgg tgcgggcctc ttcgctatta cgccagctgg cgaaagggg    540 atgtgctgca aggcgattaa gttgggtaac gccagggttt cccagtcac gacgttgtaa    600 aacgacggcc agtgaattgt aatacgactc actatagggc gaattgggcc cgacgtcgca   660
tgcttggaag ggctaattca ctcccaaaga agacaagata tccttgatct gtggatctac   720
cacacacaag gctacttccc tgattagcag aactacacac cagggccagg ggtcagatat   780
ccactgacct ttggatggtg ctacaagcta gtaccagttg agccagataa ggtagaagag   840
gccaataaag gagagaacac cagcttgtta caccctgtga gcctgcatgg gatggatgac   900
ccggagagag aagtgttaga gtggaggttt gacagccgcc tagcatttca tcacgtggcc   960
cgagagctgc atccggagta cttcaagaac tgctgatatc gagcttgcta caagggactt  1020
tccgctgggg actttccagg gaggcgtggc ctgggcggga ctggggagtg gcgagccctc  1080
agatcctgca tataagcagc tgcttttgc ctgtactggg tctctctggt tagaccagat   1140
ctgagcctgg gagctctctg gctaactagg gaacccactg cttaagcctc aataaagctt  1200
gccttgagtg cttcaagtag tgtgtgcccg tctgttgtgt gactctggta actagagatc   1260
cctcagaccc ttttagtcag tgtggaaaat ctctagcagt ggcgcccgaa cagggacttg   1320
aaagcgaaag ggaaaccaga ggagctctct cgacgcagga ctcggcttgc tgaagcgcgc   1380
acggcaagag gcgagggggcg gcgactggtg agtacgccaa aaattttgac tagcggaggc   1440
tagaaggaga gagatgggtg cgagagcgtc agtattaagc gggggagaat tagatcgcga   1500
tgggaaaaaa ttcggttaag gccagggga aagaaaaaat ataaattaaa acatatagta   1560
tgggcaagca gggagctaga acgattcgca gttaatcctg gcctgttaga acatcagaa    1620
```

```
ggctgtagac aaatactggg acagctacaa ccatcccttc agacaggatc agaagaactt    1680
agatcattat ataatacagt agcaaccctc tattgtgtgc atcaaaggat agagataaaa    1740
gacaccaagg aagctttaga caagatagag gaagagcaaa acaaaagtaa gaccaccgca    1800
cagcaagcgg ccgctgatct tcagacctgg aggaggagat atgagggaca attggagaag    1860
tgaattatat aaatataaag tagtaaaaat tgaaccatta ggagtagcac ccaccaaggc    1920
aaagagaaga gtggtgcaga gagaaaaaag agcagtggga ataggagctt tgttccttgg    1980
gttcttggga gcagcaggaa gcactatggg cgcagcgtca atgacgctga cggtacaggc    2040
cagacaatta ttgtctggta tagtgcagca gcagaacaat ttgctgaggg ctattgaggc    2100
gcaacagcat ctgttgcaac tcacagtctg gggcatcaag cagctccagg caagaatcct    2160
ggctgtggaa agatacctaa aggatcaaca gctcctgggg atttggggtt gctctggaaa    2220
actcatttgc accactgctg tgccttggaa tgctagttgg agtaataaat ctctggaaca    2280
gatttggaat cacacgacct ggatggagtg ggacagagaa attaacaatt acacaagctt    2340
aatacactcc ttaattgaag aatcgcaaaa ccagcaagaa aagaatgaac aagaattatt    2400
ggaattagat aaatgggcaa gtttgtggaa ttggtttaac ataacaaatt ggctgtggta    2460
tataaaatta ttcataatga tagtaggagg cttggtaggt ttaagaatag ttttgctgt    2520
actttctata gtgaatagag ttaggcaggg atattcacca ttatcgtttc agacccacct    2580
cccaaccccg aggggacccg acaggcccga aggaatagaa gaagaaggtg gagagagaga    2640
cagagacaga tccattcgat tagtgaacgg atctcgacgg gatcgatttt aaaagaaaag    2700
gggggattgg ggggtacagt gcaggggaaa gaatagtaga cataatagca acagacatac    2760
aaactaaaga attacaaaaa caaattacaa aaattcaaaa ttttatcgat aagctttgca    2820
aagatggata agttttttaaa cagagaggaa tctttgcagc taatggacct tctaggtctg    2880
accccgtacg cctcgagaga tctgatcata atcagccata ccacatttgt agaggtttta    2940
cttgctttaa aaaacctccc cacactcccc ctgaacctga aacataaaat gaatgcaatt    3000
gttgttgtta acttgtttat tgcagcttat aatggttaca ataaggcaa tagcatcaca    3060
aatttcacaa ataaggcatt ttttcactg cattctagtt ttggtttgtc caaactcatc    3120
aatgtatctt atcatgtctg gatctcaaat ccctcggaag ctgcgcctgt cttaggttgg    3180
agtgatacat ttttatcact tttacccgtc tttggattag gcagtagctc tgacggccct    3240
cctgtcttag gttagtgaaa atgtcactc tcttacccgt cattggctgt ccagcttagc    3300
tcgcagggga ggtggtctgc ctgcaggcgg atggcgttaa catatgacaa ctttctcccg    3360
ggtaatctga ccgttcgcta gccctgggga gagaggtcgg tgattcggtc aacgagggag    3420
ccgactgccg acgtgcgctc cggaggcttg cagaatgcgg aacaccgcgc gggcaggaac    3480
agggcccaca ctaccgcccc acaccccgcc tcccgcaccg cccccttccg gccgctgctc    3540
tcggcgcgcc ccgctgagca gccgctattg gccacagccc atcgcggtcg gcgcgctgcc    3600
attgctcccct ggcgctgtcc gtctgcgagg gtactagtga gacgtgcggc ttccgtttgt    3660
cacgtccggc acgccgcgaa ccgcaaggaa ccttcccgac ttaggggcgg agcaggaagc    3720
gtcgccgggg ggcccacaag ggtagcgcg aagatccggg tgacgctgcg aacgacgtg    3780
aagaatgtgc gagacccagg gtcggcgccg ctgcgtttcc cggaaccacg cccagagcag    3840
ccgcgtccct gcgcaaaccc agggctgcca aggaaaaggc gcaaccccaa ccccgtggtt    3900
aattaaggtg aaaggagtgg gaattggctc cggtgcccgt cagtgggcag agcgcacatc    3960
gcccacagtc cccgagaagt tggggggagg ggtcggcaat tgaaccggtg cctagagaag    4020
```

```
gtggcgcggg gtaaactggg aaagtgatgt cgtgtactgg ctccgccttt ttcccgaggg   4080
tgggggagaa ccgtatataa gtgcagtagt cgccgtgaac gttcttttc gcaacgggtt    4140 tgccgccaga acacaggtaa gtgccgtgtg tggttcccgc gggcctggcc tctttacggg   4200
ttatggccct tgcgtgcctt gaattacttc cacctggctg cagtacgtga ttcttgatcc   4260
cgagcttcgg gttggaagtg ggtgggagag ttcgaggcct tgcgcttaag gagccccttc   4320
gcctcgtgct tgagttgagg cctggcctgg gcgctgggc cgccgcgtgc gaatctggtg    4380
gcaccttcgc gcctgtctcg ctgctttcga taagtctcta gccatttaaa atttttgatg   4440
acctgctgcg acgcttttt tctggcaaga tagtcttgta aatgcgggcc aagatctgca    4500
cactggtatt tcggttttg gggccgcggg cggcgacggg gccgtgcgt cccagcgcac     4560 atgttcggcg aggcgggcc tgcgagcgcg gccaccgaga atcggacggg ggtagtctca    4620
agctggccgg cctgctctgg tgcctggcct cgcgccgccg tgtatcgccc cgccctgggc   4680
ggcaaggctg gcccggtcgg caccagttgc gtgagcggaa agatggccgc ttcccggccc   4740
tgctgcaggg agctcaaaat ggaggacgcg gcgctcggga gagcgggcgg gtgagtcacc   4800
cacacaaagg aaaagggcct ttccgtcctc agccgtcgct tcatgtgact ccacggagta   4860
ccgggcgccg tccaggcacc tcgattagtt ctcgagcttt tggagtacgt cgtctttagg   4920 ttgggggag gggttttatg cgatggagtt tccccacact gagtgggtgg agactgaagt    4980
taggccagct tggcacttga tgtaattctc cttggaattt gccctttttg agtttggatc   5040
ttggttcatt ctcaagcctc agacagtggt tcaaagtttt tttcttccat ttcaggtgtc   5100
gtgaggaatt ctgcagtcga cggtaccgcg ggcgcgcccc gggatccaag cttcaattgt   5160
ggtcactcga caatcaacct ctggattaca aaatttgtga agattgact ggtattctta    5220 actatgttgc tccttttacg ctatgtggat acgctgcttt aatgcctttg tatcatgcta   5280
ttgcttcccg tatggctttc attttctcct ccttgtataa atcctggttg ctgtctcttt   5340
atgaggagtt gtgccccgtt gtcaggcaac gtggcgtggt gtgcactgtg tttgctgacg   5400 caaccccccac tggttggggc attgccacca cctgtcagct ccttccgggg actttcgctt   5460
tccccctccc tattgccacg gcggaactca tcgccgcctg ccttgcccgc tgctggacag   5520
gggctcggct gttgggcact gacaattccg tggtgttgtc ggggaagctg acgtcctttc   5580
catggctgct cgcctgtgtt gccacctgga ttctgcgcgg gacgtccttc tgctacgtcc   5640
cttcggccct caatccagcg gaccttcctt cccgcggcct gctgccggct ctgcggcctc   5700
ttccgcgtct tcgccttcgc cctcagacga gtcggatctc cctttgggcc gcctccccgc   5760
ctgctcgaga cctagaaaaa catggagcaa tcacaagtag caatacagca gctaccaatg   5820
ctgattgtgc ctggctagaa gcacaagagg aggaggaggt gggttttcca gtcacacctc   5880
aggtaccttt aagaccaatg acttacaagg cagctgtaga tcttagccac ttttaaaag   5940 aaaaggggg actggaaggg ctaattcact cccaacgaag acaagatctg cttttgctt    6000 gtactgggtc tctctggtta gaccagatct gagcctggga gctctctggc taactaggga   6060
acccactgct taagcctcaa taaagcttgc cttgagtgct tcaagtagtg tgtgcccgtc   6120
tgttgtgtga ctctggtaac tagagatccc tcagaccctt ttagtcagtg tggaaaatct   6180
ctagcagtag tagttcatgt catcttatta ttcagtattt ataacttgca aagaaatgaa   6240
tatcagagag tgagaggacg cgttggatgc atagcttgag tattctatag tgtcacctaa   6300
atagcttggc gtaatcatgg tcatagctgt ttcctgtgtg aaattgttat ccgctcacaa   6360
ttccacacaa catacgagcc ggaagcataa agtgtaaagc ctggggtgcc taatgagtga   6420
```

```
gctaactcac attaattgcg ttgcgctcac tgcccgcttt ccagtcggga aacctgtcgt    6480
gccagctgca ttaatgaatc ggccaacgcg cggggagagg cggtttgcgt attgggcgct    6540
cttccgcttc ctcgctcact gactcgctgc gctcggtcgt tcggctgcgg cgagcggtat    6600
cagctcactc aaaggcggta atacggttat ccacagaatc aggggataac gcaggaaaga    6660
acatgtgagc aaaaggccag caaaaggcca ggaaccgtaa aaaggccgcg ttgctggcgt    6720
ttttccatag gctccgcccc cctgacgagc atcacaaaaa tcgacgctca agtcagaggt    6780
ggcgaaaccc gacaggacta taaagatacc aggcgtttcc ccctggaagc tccctcgtgc    6840
gctctcctgt tccgaccctg ccgcttaccg gatacctgtc cgcctttctc ccttcgggaa    6900
gcgtggcgct ttctcatagc tcacgctgta ggtatctcag ttcggtgtag tcgttcgct    6960 ccaagctggg ctgtgtgcac gaaccccccg ttcagcccga ccgctgcgcc ttatccggta    7020
actatcgtct tgagtccaac ccggtaagac acgacttatc gccactggca gcagccactg    7080
gtaacaggat tagcagagcg aggtatgtag cggtgctac agagttcttg aagtggtggc    7140
ctaactacgg ctacactaga agaacagtat ttggtatctg cgctctgctg aagccagtta    7200
ccttcggaaa aagagttggt agctcttgat ccggcaaaca aaccaccgct ggtagcggtg    7260
gtttttttgt ttgcaagcag cagattacgc gcagaaaaaa aggatctcaa gaagatcctt    7320
tgatcttttc tacggggtct gacgctcagt ggaacgaaaa ctcacgttaa gggattttgg    7380
tcatgagatt atcaaaaagg atcttcacct agatccttt aaattaaaaa tgaagtttta    7440
aatcaatcta agtatatat gagtaaactt ggtctgacag ttaccaatgc ttaatcagtg    7500
aggcacctat ctcagcgatc tgtctatttc gttcatccat agttgcctga ctccccgtcg    7560
tgtagataac tacgatacgg gagggcttac catctggccc cagtgctgca atgataccgc    7620
gagacccacg ctcaccggct ccagatttat cagcaataaa ccagccagcc ggaagggccg    7680
agcgcagaag tggtcctgca actttatccg cctccatcca gtctattaat gttgccggg    7740 aagctagagt aagtagttcg ccagttaata gtttgcgcaa cgttgttgcc attgctacag    7800
gcatcgtggt gtcacgctcg tcgtttggta tggcttcatt cagctccggt tcccaacgat    7860
caaggcgagt tacatgatcc cccatgttgt gcaaaaaagc ggttagctcc ttcggtcctc    7920
cgatcgttgt cagaagtaag ttggccgcag tgttatcact catggttatg gcagcactgc    7980
ataattctct tactgtcatg ccatccgtaa gatgcttttc tgtgactggt gagtactcaa    8040
ccaagtcatt ctgagaatag tgtatgcggc gaccgagttg ctcttgcccg gcgtcaatac    8100
gggataatac cgcgccacat agcagaactt taaaagtgct catcattgga aaacgttctt    8160
cggggcgaaa actctcaagg atcttaccgc tgttgagatc cagttcgatg taacccactc    8220
gtgcacccaa ctgatcttca gcatctttta ctttcaccag cgtttctggg tgagcaaaaa    8280
caggaaggca aaatgccgca aaaagggaa taagggcgac acggaaatgt tgaatactca    8340
tactcttcct ttttcaatat tattgaagca tttatcaggg ttattgtctc atgagcggat    8400
acatatttga atgtatttag aaaaataaac aaataggggt tccgcgcaca tttccccgaa    8460
aagtgccacc tgatgcggtg tgaaataccg cacagatgcg taaggagaaa ataccgcatc    8520
agg                                                                  8523
```

<210> SEQ ID NO 2
<211> LENGTH: 10025
<212> TYPE: DNA
<213> ORGANISM: Artificial Sequence
<220> FEATURE:
<223> OTHER INFORMATION: synthetic vector

<400> SEQUENCE: 2

```
aaattgtaag cgttaatatt ttgttaaaat tcgcgttaaa tttttgttaa atcagctcat      60
tttttaacca ataggccgaa atcggcaaaa tcccttataa atcaaaagaa tagaccgaga     120
tagggttgag tgttgttcca gtttggaaca agagtccact attaaagaac gtggactcca    180
acgtcaaagg gcgaaaaacc gtctatcagg gcgatggccc actacgtgaa ccatcaccct    240
aatcaagttt tttggggtcg aggtgccgta aagcactaaa tcggaaccct aaagggagcc    300
cccgatttag agcttgacgg ggaaagccgg cgaacgtggc gagaaaggaa gggaagaaag    360
cgaaaggagc gggcgctagg gcgctggcaa gtgtagcggt cacgctgcgc gtaaccacca    420
cacccgccgc gcttaatgcg ccgctacagg gcgcgtccat tcgccattca ggctgcgcaa    480
ctgttgggaa gggcgatcgg tgcgggcctc ttcgctatta cgccagctgg cgaaaggggg    540
atgtgctgca aggcgattaa gttgggtaac gccagggttt tcccagtcac gacgttgtaa    600
aacgacggcc agtgaattgt aatacgactc actatagggc gaattgggcc cgacgtcgca    660
tgcttggaag ggctaattca ctcccaaaga agacaagata tccttgatct gtggatctac    720
cacacacaag gctacttccc tgattagcag aactacacac cagggccagg ggtcagatat    780
ccactgacct ttggatggtg ctacaagcta gtaccagttg agccagataa ggtagaagag    840
gccaataaag gagagaacac cagcttgtta caccctgtga gcctgcatgg gatggatgac    900
ccggagagag aagtgttaga gtggaggttt gacagccgcc tagcatttca tcacgtggcc    960
cgagagctgc atccggagta cttcaagaac tgctgatatc gagcttgcta caagggactt   1020
tccgctgggg actttccagg gaggcgtggc ctgggcggga ctgggagtg gcgagccctc    1080
agatcctgca tataagcagc tgcttttgc ctgtactggg tctctctggt tagaccagat    1140
ctgagcctgg gagctctctg gctaactagg gaacccactg cttaagcctc aataaagctt   1200
gccttgagtg cttcaagtag tgtgtgcccg tctgttgtgt gactctggta actagagatc    1260
cctcagaccc ttttagtcag tgtggaaaat ctctagcagt ggcgcccgaa cagggacttg    1320
aaagcgaaag ggaaaccaga ggagctctct cgacgcagga ctcggcttgc tgaagcgcgc    1380
acggcaagag gcgaggggcg cgactggtg agtacgccaa aaattttgac tagcggaggc    1440
tagaaggaga gagatgggtg cgagagcgtc agtattaagc ggggagaat tagatcgcga    1500
tgggaaaaaa ttcggttaag gccagggggga agaaaaaat ataattaaa acatatagta    1560
tgggcaagca gggagctaga acgattcgca gttaatcctg gcctgttaga acatcagaa    1620
ggctgtagac aaatactggg acagctacaa ccatcccttc agacaggatc agaagaactt    1680
agatcattat ataatacagt agcaaccctc tattgtgtgc atcaaaggat agagataaaa    1740
gacaccaagg aagctttaga caagatagag gaagagcaaa acaaaagtaa gaccaccgca    1800
cagcaagcgg ccgctgatct tcagacctgg aggaggagat atgagggaca attggagaag    1860
tgaattatat aaatataaag tagtaaaaat tgaaccatta ggagtagcac ccaccaaggc    1920
aaagagaaga gtggtgcaga gagaaaaaag agcagtggga ataggagctt tgttccttgg    1980
gttcttggga gcagcaggaa gcactatggg cgcagcgtca atgacgctga cggtacaggc    2040
cagacaatta ttgtctggta tagtgcagca gcagaacaat ttgctgaggg ctattgaggc    2100
gcaacagcat ctgttgcaac tcacagtctg gggcatcaag cagctccagg caagaatcct    2160
ggctgtggaa agatacctaa aggatcaaca gctcctgggg atttggggtt gctctggaaa    2220
actcatttgc accactgctg tgccttggaa tgctagttgg agtaataaat ctctggaaca    2280
gatttggaat cacacgacct ggatggagtg ggacagagaa attaacaatt acacaagctt    2340
```

-continued

```
aatacactcc ttaattgaag aatcgcaaaa ccagcaagaa aagaatgaac aagaattatt    2400
ggaattagat aaatgggcaa gtttgtggaa ttggtttaac ataacaaatt ggctgtggta    2460
tataaaatta ttcataatga tagtaggagg cttggtaggt ttaagaatag ttttgctgt     2520 actttctata gtgaatagag ttaggcaggg atattcacca ttatcgtttc agacccacct    2580
cccaaccccg aggggacccg acaggcccga aggaatagaa gaagaaggtg gagagagaga    2640
cagagacaga tccattcgat tagtgaacgg atctcgacgg gatcgatttt aaaagaaaag    2700
gggggattgg ggggtacagt gcaggggaaa gaatagtaga cataatagca acagacatac    2760
aaactaaaga attacaaaaa caaattacaa aaattcaaaa ttttatcgat aagctttgca    2820
aagatggata aagttttaaa cagagaggaa tctttgcagc taatggacct tctaggtctg    2880
accccgtacg cctcgagaga tctgatcata atcagccata ccacatttgt agaggtttta    2940
cttgctttaa aaacctccc acacctcccc ctgaacctga aacataaaat gaatgcaatt     3000
gttgttgtta acttgtttat tgcagcttat aatggttaca aataaggcaa tagcatcaca    3060
aatttcacaa ataaggcatt tttttcactg cattctagtt ttggtttgtc caaactcatc    3120
aatgtatctt atcatgtctg gatctcaaat ccctcggaag ctgcgcctgt cttaggttgg    3180
agtgatacat ttttatcact tttacccgtc tttggattag gcagtagctc tgacggccct    3240
cctgtcttag gttagtgaaa aatgtcactc tcttacccgt cattggctgt ccagcttagc    3300
tcgcagggga ggtggtctgc ctgcaggtta gaacagtctc ttttcgtatg agtgcagtga    3360
gtggacgccg ccttcgacct gggctgaaga agttcttttc tcgaacttca gttcgccgga    3420
atacatcatt gcccgcacct gtgtcaggct cttagcgccg atatcctggc atgaatgctg    3480
aattccggcg atcaggtaag gcacgaattt gtgaatactg cccttatcct ggacagctcc    3540
agacacgccc tgtgcgactt tgatcttgtc tgcctcggaa aaatacctgt tctgagagga    3600
cagatgctta tccatggcgt ccagtgaccc catgccccta tatttcttca gtctgaaccc    3660
atcactaaag aagtactcgc cggggggctc tgtggttgca gccagcaggc tgcccatcat    3720
cactgtgctt gcccccagag ccagggcttt tgcgatgtgg cccacattct gaattccccc    3780
gtcagcgatc actgggactc cgaatctccg ggcatactcg tacaccttgt agacagcagt    3840
tgcctgaggt cgtccacagg ccagcacttc ctgaatgatg cagattgatc cactccccat    3900
tccgaccctc agagcatcca ctcctgcgtc aatcaggttt ttggcctggg ctgcggtcac    3960
gacattgcct ccgatgacct gcagatttgg gtacttgtcc ttaatgtact tgatcatatt    4020
aatctggaag atgctgtttc cctggcttga atccagcacg accacgtcca ccctgcctg    4080 agccagcaga tccaggcgat atttatcgtc ctcgtgtgtg ccaatagcgg ctccacacag    4140
cagctgtttc tttgcgtcct tactagccag agggtaatct cgattttct tcaggtcggt     4200 gcgggcaatg attgccacca gctcatcgtc ttcattcacg ataggcagtt ttccttctt    4260 agaccgctgc agaatctcgt tggcttcctt cagtgtgatg ccggcaggtg cgaccaccag    4320
atcttcgcgt ttggtcataa tctcttccag aaaacagtca tgctcttcct ccttcaggaa    4380
atcgatgtct cgactagaaa tgattcccac cagtcggctg cccattcgtc cagtatctgt    4440 aatgggggatg ccgcaaaatc cgtgcctagc tttggcctcg aacacatcgc ggaccctgtc   4500
cttgggcctc aggaccactg ggtcggtgat aaagccctgt tcgtatttct tcacctttct    4560
gacctcattg gcctgaaatt ctggagtgca gttatggtga atgaaccga tcccgcctgt     4620 cagtgccata gcaatggcca tgccagcctc ggtgacagtg tccatagggg agctcaccag    4680
gggtgtcttc agggtgattt tcttggtcag ggcagaagtc agatccacct ggtctgcggt    4740
```

-continued

```
aaaatcaata tagccgggca ggatcaggaa gtcgttgtaa gtcagcccgt ctccacaatt    4800
aaacagctgc tgggcggtca gtccatcatc agggacatag gaagtgcctc cagaaatcag    4860
gtagtcggcc atggtggcgc tagccctggg gagagaggtc ggtgattcgg tcaacgaggg    4920
agccgactgc cgacgtgcgc tccggaggct tgcagaatgc ggaacaccgc gcgggcagga    4980
acagggccca cactaccgcc ccacaccccg cctcccgcac cgcccttcc cggccgctgc    5040
tctcggcgcg ccccgctgag cagccgctat tggccacagc ccatcgcggt cggcgcgctg    5100
ccattgctcc ctggcgctgt ccgtctgcga gggtactagt gagacgtgcg gcttccgttt    5160
gtcacgtccg gcacgccgcg aaccgcaagg aaccttcccg acttaggggc ggagcaggaa    5220
gcgtcgccgg ggggcccaca agggtagcgg cgaagatccg ggtgacgctg cgaacggacg    5280
tgaagaatgt gcgagaccca gggtcggcgc cgctgcgttt cccggaacca cgcccagagc    5340
agccgcgtcc ctgcgcaaac ccagggctgc caaggaaaag gcgcaacccc aaccccgtgg    5400
ttaattaagg tgaaaggagt gggaattggc tccggtgccc gtcagtgggc agagcgcaca    5460
tcgcccacag tccccgagaa gttgggggga ggggtcggca attgaaccgg tgcctagaga    5520
aggtggcgcg gggtaaactg ggaaagtgat gtcgtgtact ggctccgcct ttttcccgag    5580
ggtgggggag aaccgtatat aagtgcagta gtcgccgtga acgttctttt tcgcaacggg    5640
tttgccgcca gaacacaggt aagtgccgtg tgtggttccc gcgggcctgg cctctttacg    5700
ggttatggcc cttgcgtgcc ttgaattact tccacctggc tgcagtacgt gattcttgat    5760
cccgagcttc gggttggaag tgggtgggag agttcgaggc cttgcgctta aggagcccct    5820
tcgcctcgtg cttgagttga ggcctggcct gggcgctggg gccgccgcgt gcgaatctgg    5880
tggcaccttc gcgcctgtct cgctgctttc gataagtctc tagccattta aaattttga    5940
tgacctgctg cgacgctttt tttctggcaa gatagtcttg taaatgcggg ccaagatctg    6000
cacactggta tttcggtttt tggggccgcg gcggcgacg gggcccgtgc gtcccagcgc    6060
acatgttcgg cgaggcgggg cctgcgagcg cggccaccga gaatcggacg ggggtagtct    6120
caagctggcc ggcctgctct ggtgcctggc ctcgcgccgc cgtgtatcgc cccgccctgg    6180
gcggcaaggc tggcccggtc ggcaccagtt gcgtgagcgg aaagatgcc gcttcccggc    6240
cctgctgcag ggagctcaaa atggaggacg cggcgctcgg gagagcgggc gggtgagtca    6300
cccacacaaa ggaaaagggc cttttccgtcc tcagccgtcg cttcatgtga ctccacggag    6360
taccgggcgc cgtccaggca cctcgattag ttctcgagct tttggagtac gtcgtcttta    6420
ggttgggggg aggggtttta tgcgatgag tttccccaca ctgagtgggt ggagactgaa    6480
gttaggccag cttggcactt gatgtaattc tccttggaat ttgcccttt tgagtttgga    6540
tcttggttca ttctcaagcc tcagacagtg gttcaaagtt ttttcttcc atttcaggtg    6600
tcgtgaggaa ttctgcagtc gacggtaccg cgggcgcgcc ccgggatcca agcttcaatt    6660
gtggtcactc gacaatcaac ctctggatta caaaatttgt gaaagattga ctggtattct    6720
taactatgtt gctcctttta cgctatgtgg atacgctgct ttaatgcctt tgtatcatgc    6780
tattgcttcc cgtatggctt tcattttctc ctccttgtat aaatcctggt tgctgtctct    6840
ttatgaggag ttgtggcccg ttgtcaggca acgtggcgtg gtgtgcactg tgtttgctga    6900
cgcaaccccc actggttggg gcattgccac cacctgtcag ctccttccg gactttcgc    6960
tttcccctc cctattgcca cggcggaact catcgccgcc tgccttgccc gctgctggac    7020
aggggctcgc ctgttgggca ctgacaattc cgtggtgttg tcgggaagc tgacgtcctt    7080
tccatggctg ctcgcctgtg ttgccacctg gattctgcgc gggacgtcct tctgctacgt    7140
```

```
cccttcggcc ctcaatccag cggaccttcc ttcccgcggc ctgctgccgg ctctgcggcc    7200
tcttccgcgt cttcgccttc gccctcagac gagtcggatc tccctttggg ccgcctcccc    7260
gcctgctcga gacctagaaa aacatggagc aatcacaagt agcaatacag cagctaccaa    7320
tgctgattgt gcctggctag aagcacaaga ggaggaggag gtgggttttc cagtcacacc    7380
tcaggtacct ttaagaccaa tgacttacaa ggcagctgta gatcttagcc acttttttaaa   7440 agaaaagggg ggactggaag ggctaattca ctcccaacga agacaagatc tgcttttttgc   7500 ttgtactggg tctctctggt tagaccagat ctgagcctgg gagctctctg gctaactagg    7560
gaacccactg cttaagcctc aataaagctt gccttgagtg cttcaagtag tgtgtgcccg    7620
tctgttgtgt gactctggta actagagatc cctcagaccc ttttagtcag tgtggaaaat    7680
ctctagcagt agtagttcat gtcatcttat tattcagtat ttataacttg caaagaaatg    7740
aatatcagag agtgagagga cgcgttggat gcatagcttg agtattctat agtgtcacct    7800
aaatagcttg gcgtaatcat ggtcatagct gtttcctgtg tgaaattgtt atccgctcac    7860
aattccacac aacatacgag ccggaagcat aaagtgtaaa gcctggggtg cctaatgagt    7920
gagctaactc acattaattg cgttgcgctc actgcccgct ttccagtcgg gaaacctgtc    7980
gtgccagctg cattaatgaa tcggccaacg cgcggggaga ggcggtttgc gtattgggcg    8040
ctcttccgct tcctcgctca ctgactcgct gcgctcggtc gttcggctgc ggcgagcggt    8100
atcagctcac tcaaaggcgg taatacggtt atccacagaa tcaggggata acgcaggaaa    8160
gaacatgtga gcaaaaggcc agcaaaaggc caggaaccgt aaaaaggccg cgttgctggc    8220 gttttttccat aggctccgcc cccctgacga gcatcacaaa aatcgacgct caagtcagag    8280
gtggcgaaac ccgacaggac tataaagata ccaggcgttt ccccctggaa gctccctcgt    8340
gcgctctcct gttccgaccc tgccgcttac cggatacctg tccgcctttc tcccttcggg    8400
aagcgtggcg ctttctcata gctcacgctg taggtatctc agttcggtgt aggtcgttcg    8460
ctccaagctg ggctgtgtgc acgaaccccc cgttcagccc gaccgctgcg ccttatccgg    8520
taactatcgt cttgagtcca acccggtaag acacgactta tcgccactgg cagcagccac    8580
tggtaacagg attagcagag cgaggtatgt aggcggtgct acagagttct tgaagtggtg    8640
gcctaactac ggctacacta gaagaacagt atttggtatc tgcgctctgc tgaagccagt    8700
taccttcgga aaaagagttg gtagctcttg atccggcaaa caaaccaccg ctggtagcgg    8760
tggttttttt gtttgcaagc agcagattac gcgcagaaaa aaaggatctc aagaagatcc    8820
tttgatcttt tctacggggt ctgacgctca gtggaacgaa aactcacgtt aagggatttt    8880
ggtcatgaga ttatcaaaaa ggatcttcac ctagatcctt ttaaattaaa aatgaagttt    8940
taaatcaatc taaagtatat atgagtaaac ttggtctgac agttaccaat gcttaatcag    9000
tgaggcacct atctcagcga tctgtctatt tcgttcatcc atagttgcct gactccccgt    9060
cgtgtagata actacgatac gggagggctt accatctggc cccagtgctg caatgatacc    9120
gcgagaccca cgctcaccgg ctccagattt atcagcaata aaccagccag ccggaagggc    9180
cgagcgcaga agtggtcctg caactttatc cgcctccatc cagtctatta attgttgccg    9240
ggaagctaga gtaagtagtt cgccagttaa tagtttcgc aacgttgttg ccattgctac     9300
aggcatcgtg gtgtcacgct cgtcgtttgg tatggcttca ttcagctccg gttcccaacg    9360
atcaaggcga gttacatgat ccccatgtt gtgcaaaaaa gcggttagct ccttcggtcc     9420
tccgatcgtt gtcagaagta agttggccgc agtgttatca ctcatggtta tggcagcact    9480
gcataattct cttactgtca tgccatccgt aagatgcttt tctgtgactg gtgagtactc    9540
```

| | | |
|---|---|---|
| aaccaagtca ttctgagaat agtgtatgcg gcgaccgagt tgctcttgcc cggcgtcaat | 9600 | |
| acgggataat accgcgccac atagcagaac tttaaaagtg ctcatcattg gaaaacgttc | 9660 | |
| ttcggggcga aaactctcaa ggatcttacc gctgttgaga tccagttcga tgtaacccac | 9720 | |
| tcgtgcaccc aactgatctt cagcatcttt tactttcacc agcgtttctg ggtgagcaaa | 9780 | |
| aacaggaagg caaaatgccg caaaaaaggg aataagggcg acacggaaat gttgaatact | 9840 | |
| catactcttc ctttttcaat attattgaag catttatcag ggttattgtc tcatgagcgg | 9900 | |
| atacatattt gaatgtattt agaaaaataa acaaataggg gttccgcgca catttccccg | 9960 | |
| aaaagtgcca cctgatgcgg tgtgaaatac cgcacagatg cgtaaggaga aaataccgca | 10020 | |
| tcagg | 10025 | |

<210> SEQ ID NO 3
<211> LENGTH: 11298
<212> TYPE: DNA
<213> ORGANISM: Artificial Sequence
<220> FEATURE:
<223> OTHER INFORMATION: synthetic vector

<400> SEQUENCE: 3

| | | |
|---|---|---|
| aaattgtaag cgttaatatt ttgttaaaat tcgcgttaaa ttttttgttaa atcagctcat | 60 | |
| tttttaacca ataggccgaa atcggcaaaa tcccttataa atcaaaagaa tagaccgaga | 120 | |
| tagggttgag tgttgttcca gtttggaaca agagtccact attaaagaac gtggactcca | 180 | |
| acgtcaaagg gcgaaaaacc gtctatcagg gcgatggccc actacgtgaa ccatcaccct | 240 | |
| aatcaagttt ttggggtcg aggtgccgta aagcactaaa tcggaaccct aaagggagcc | 300 | |
| cccgatttag agcttgacgg ggaaagccgg cgaacgtggc gagaaaggaa gggaagaaag | 360 | |
| cgaaaggagc gggcgctagg gcgctggcaa gtgtagcggt cacgctgcgc gtaaccacca | 420 | |
| cacccgccgc gcttaatgcg ccgctacagg gcgcgtccat tcgccattca ggctgcgcaa | 480 | |
| ctgttgggaa gggcgatcgg tgcgggcctc ttcgctatta cgccagctgg cgaaaggggg | 540 | |
| atgtgctgca aggcgattaa gttgggtaac gccagggttt tcccagtcac gacgttgtaa | 600 | |
| aacgacggcc agtgaattgt aatacgactc actatagggc gaattgggcc cgacgtcgca | 660 | |
| tgcttggaag ggctaattca ctcccaaaga agacaagata tccttgatct gtggatctac | 720 | |
| cacacacaag gctacttccc tgattagcag aactacacac cagggccagg ggtcagatat | 780 | |
| ccactgacct ttggatggtg ctacaagcta gtaccagttg agccagataa ggtagaagag | 840 | |
| gccaataaag gagagaacac cagcttgtta caccctgtga gcctgcatgg gatggatgac | 900 | |
| ccggagagag aagtgttaga gtggaggttt gacagccgcc tagcatttca tcacgtggcc | 960 | |
| cgagagctgc atccggagta cttcaagaac tgctgatatc gagcttgcta caagggactt | 1020 | |
| tccgctgggg actttccagg gaggcgtggc ctgggcggga ctggggagtg gcgagccctc | 1080 | |
| agatcctgca tataagcagc tgcttttttgc ctgtactggg tctctctggt tagaccagat | 1140 | |
| ctgagcctgg gagctctctg gctaactagg gaacccactg cttaagcctc aataaagctt | 1200 | |
| gccttgagtg cttcaagtag tgtgtgcccg tctgttgtgt gactctggta actagagatc | 1260 | |
| cctcagaccc ttttagtcag tgtggaaaat ctctagcagt ggcgcccgaa cagggacttg | 1320 | |
| aaagcgaaag ggaaaccaga ggagctctct cgacgcagga ctcggcttgc tgaagcgcgc | 1380 | |
| acggcaagag gcgaggggcg gcgactggtg agtacgccaa aaattttgac tagcggaggc | 1440 | |
| tagaaggaga gagatgggtg cgagagcgtc agtattaagc gggggagaat tagatcgcga | 1500 | |
| tgggaaaaaa ttcggttaag gccaggggga aagaaaaaat ataaattaaa acatatagta | 1560 | |

```
tgggcaagca gggagctaga acgattcgca gttaatcctg gcctgttaga acatcagaa       1620 ggctgtagac aaatactggg acagctacaa ccatcccttc agacaggatc agaagaactt      1680
agatcattat ataatacagt agcaaccctc tattgtgtgc atcaaaggat agagataaaa      1740
gacaccaagg aagctttaga caagatagag gaagagcaaa acaaaagtaa gaccaccgca      1800
cagcaagcgg ccgctgatct tcagacctgg aggaggagat atgagggaca attggagaag      1860
tgaattatat aaatataaag tagtaaaaat tgaaccatta ggagtagcac ccaccaaggc      1920
aaagagaaga gtggtgcaga gagaaaaaag agcagtggga ataggagctt tgttccttgg      1980
gttcttggga gcagcaggaa gcactatggg cgcagcgtca atgacgctga cggtacaggc      2040
cagacaatta ttgtctggta tagtgcagca gcagaacaat ttgctgaggg ctattgaggc      2100
gcaacagcat ctgttgcaac tcacagtctg gggcatcaag cagctccagg caagaatcct      2160
ggctgtggaa agatacctaa aggatcaaca gctcctgggg atttggggtt gctctggaaa      2220
actcatttgc accactgctg tgccttggaa tgctagttgg agtaataaat ctctggaaca      2280
gatttggaat cacacgacct ggatggagtg ggacagagaa attaacaatt acacaagctt      2340
aatacactcc ttaattgaag aatcgcaaaa ccagcaagaa aagaatgaac aagaattatt      2400
ggaattagat aaatgggcaa gtttgtggaa ttggtttaac ataacaaatt ggctgtggta      2460
tataaaatta ttcataatga tagtaggagg cttggtaggt ttaagaatag ttttgctgt       2520 actttctata gtgaatagag ttaggcaggg atattcacca ttatcgtttc agacccacct      2580
cccaaccccg aggggacccg acaggcccga aggaatagaa gaagaaggtg gagagagaga      2640
cagagacaga tccattcgat tagtgaacgg atctcgacgg gatcgatttt aaaagaaaag      2700
gggggattgg ggggtacagt gcaggggaaa gaatagtaga cataatagca acagacatac      2760
aaactaaaga attacaaaaa caaattacaa aaattcaaaa ttttatcgat aagctttgca      2820
aagatggata aagttttaaa cagagaggaa tctttgcagc taatggacct tctaggtctg      2880
accccgtacg cctcgagaga tctgatcata atcagccata ccacatttgt agaggtttta      2940
cttgctttaa aaaacctccc acacctcccc ctgaacctga acataaaat gaatgcaatt       3000 gttgttgtta acttgtttat tgcagcttat aatggttaca ataaggcaa tagcatcaca      3060 aatttcacaa ataaggcatt ttttcactg cattctagtt ttggtttgtc caaactcatc      3120
aatgtatctt atcatgtctg gatctcaaat ccctcggaag ctgcgcctgt cttaggttgg      3180
agtgatacat ttttatcact tttacccgtc tttggattag gcagtagctc tgacggccct      3240
cctgtcttag gttagtgaaa aatgtcactc tcttacccgt cattggctgt ccagcttagc      3300
tcgcagggga ggtggtctgc ctgcaggtta gaacagtctc ttttcgtatg agtgcagtga      3360
gtggacgccg ccttcgacct gggctgaaga agttcttttc tcgaacttca gttcgccgga      3420
atacatcatt gcccgcacct gtgtcaggct cttagcgccg atatcctggc atgaatgctg      3480
aattccggcg atcaggtaag gcacgaattt gtgaatactg cccttatcct ggacagctcc      3540
agacacgccc tgtgcgactt tgatcttgtc tgcctcggaa aaatacctgt tctgagagga      3600
cagatgctta tccatggcgt ccagtgaccc catgccccta tatttcttca gtctgaaccc      3660
atcactaaag aagtactcgc cgggggcttc tgtggttgca gccagcaggc tgcccatcat      3720
cactgtgctt gcccccagag ccagggcttt tgcgatgtgg cccacattct gaattccccc      3780
gtcagcgatc actgggactc cgaatctccg ggcatactcg tacaccttgt agacagcagt      3840
tgcctgaggt cgtccacagg ccagcacttc ctgaatgatg cagattgatc cactccccat      3900
tccgaccctc agagcatcca ctcctgcgtc aatcaggttt ttggcctggg ctgcggtcac      3960
```

-continued

```
gacattgcct ccgatgacct gcagatttgg gtacttgtcc ttaatgtact tgatcatatt    4020
aatctggaag atgctgtttc cctggcttga atccagcacg accacgtcca cccctgcctg    4080
agccagcaga tccaggcgat atttatcgtc ctcgtgtgtg ccaatagcgg ctccacacag    4140
cagctgtttc tttgcgtcct tactagccag agggtaatct cgattttcct tcaggtcggt    4200
gcgggcaatg attgccacca gctcatcgtc ttcattcacg ataggcagtt ttccttcctt    4260
agaccgctgc agaatctcgt tggcttcctt cagtgtgatg ccggcaggtg cgaccaccag    4320
atcttcgcgt ttggtcataa tctcttccag aaaacagtca tgctcttcct ccttcaggaa    4380
atcgatgtct cgactagaaa tgattcccac cagtcggctg cccattcgtc cagtatctgt    4440
aatggggatg ccgcaaaatc cgtgcctagc tttggcctcg aacacatcgc ggaccctgtc    4500 cttgggctc aggaccactg ggtcggtgat aaagccctgt tcgtatttct tcaccttct    4560 gacctcattg gcctgaaatt ctggagtgca gttatggtga atgaacccga tcccgcctgt    4620
cagtgccata gcaatggcca tgccagcctc ggtgacagtg tccatagggg agctcaccag    4680
gggtgtcttc agggtgattt tcttggtcag ggcagaagtc agatccacct ggtctgcggt    4740
aaaatcaata tagccgggca ggatcaggaa gtcgttgtaa gtcagcccgt ctccacaatt    4800
aaacagctgc tgggcggtca gtccatcatc agggacatag aagtgcctc cagaaatcag    4860 gtagtcggcc atggtggcgc tagccctggg gagagaggtc ggtgattcgg tcaacgaggg    4920
agccgactgc cgacgtgcgc tccggaggct tgcagaatgc ggaacaccgc gcgggcagga    4980
acagggccca cactaccgcc ccacaccccg cctcccgcac cgcccttcc cggccgctgc    5040 tctcggcgcg ccccgctgag cagccgctat tggccacagc ccatcgcggt cggcgcgctg    5100
ccattgctcc ctggcgctgt ccgtctgcga gggtactagt gagacgtgcg gcttccgttt    5160
gtcacgtccg gcacgccgcg aaccgcaagg aaccttcccg acttaggggc ggagcaggaa    5220
gcgtcgccgg ggggcccaca agggtagcgg cgaagatccg ggtgacgctg cgaacggacg    5280
tgaagaatgt gcgagaccca gggtcggcgc cgctgcgttt cccggaacca cgcccagagc    5340
agccgcgtcc ctgcgcaaac ccagggctgc caaggaaaag gcgcaacccc aaccccgtgg    5400
ttaattaagg tgaaaggagt gggaattggc tccggtgccc gtcagtgggc agagcgcaca    5460
tcgcccacag tccccgagaa gttgggggga ggggtcggca attgaaccgg tgcctagaga    5520
aggtggcgcg gggtaaactg ggaaagtgat gtcgtgtact ggctccgcct ttttcccgag    5580
ggtgggggag aaccgtatat aagtgcagta gtcgccgtga acgttctttt tcgcaacggg    5640
tttgccgcca gaacacaggt aagtgccgtg tgtggttccc gcgggcctgg cctcttacg    5700 ggttatggcc cttgcgtgcc ttgaattact tccacctggc tgcagtacgt gattcttgat    5760
cccgagcttc gggttggaag tgggtgggag agttcgaggc cttgcgctta aggagcccct    5820
tcgcctcgtg cttgagttga ggcctggcct gggcgctggg gccgccgcgt gcgaatctgg    5880
tggcaccttc gcgcctgtct cgctgctttc gataagtctc tagccattta aaattttga    5940 tgacctgctg cgacgctttt tttctggcaa gatagtcttg taaatgcggg ccaagatctg    6000
cacactggta tttcggtttt tggggccgcg ggcggcgacg gggcccgtgc gtcccagcgc    6060
acatgttcgg cgaggcgggg cctgcgagcc cggccaccga gaatcggacg ggggtagtct    6120
caagctggcc ggcctgctct ggtgcctggc ctcgcgccgc cgtgtatcgc cccgccctgg    6180
gcggcaaggc tggcccggtc ggcaccagtt gcgtgagcgg aaagatggcc gcttcccggc    6240
cctgctgcag ggagctcaaa atggaggacg cggcgctcgg gagagcgggc gggtgagtca    6300
cccacacaaa ggaaaagggc ctttccgtcc tcagccgtcg cttcatgtga ctccacggag    6360
```

```
taccgggcgc cgtccaggca cctcgattag ttctcgagct tttggagtac gtcgtcttta    6420
ggttgggggg aggggtttta tgcgatggag tttccccaca ctgagtgggt ggagactgaa    6480
gttaggccag cttggcactt gatgtaattc tccttggaat ttgccctttt tgagtttgga    6540
tcttggttca ttctcaagcc tcagacagtg gttcaaagtt ttttctttcc atttcaggtg    6600
tcgtgaggaa ttcgccacca tgcaacttcg aaacccagag ctccacctcg gatgtgccct    6660
tgctctgagg ttcctggcgc tggtgtcttg ggatataccc ggagcacgcg ctctggacaa    6720
cgggctggcc cggactccaa ccatgggttg gctccattgg gaaaggttta tgtgcaactt    6780
ggactgccag gaagaacccg actcctgtat ttccgagaaa ctcttcatgg agatggccga    6840
gctgatggtt agcgaaggct ggaaggatgc cggttatgaa tacttgtgta tcgacgattg    6900
ttggatggct ccccagcggg acagtgaagg acgactccag gcagatccgc aacggttccc    6960
tcatggcata cggcagctcg ccaattacgt gcacagcaag ggtttgaagc tggggatata    7020
tgctgacgtg gcaacaaaaa cctgtgctgg tttccccggc agcttcggct actatgatat    7080
agatgcacaa accttcgctg attggggcgt ggacctgctt aaatttgacg gctgttactg    7140
cgacagcttg gaaaacctcg ccgatggata taaacacatg agccttgcac tcaatcggac    7200
tggccggagc attgtctact cttgcgagtg gccattgtac atgtggcctt ccagaagcc    7260 taactatacg gagattagac agtattgtaa tcactggaga actttgcag atatcgacga    7320 ctcatggaag tccatcaaat ctattctgga ctggacttca ttcaatcagg agcgcatcgt    7380
cgatgttgcc ggtccaggtg gatggaacga ccctgacatg ctcgtaattg ggaatttcgg    7440
actgtcctgg aatcagcagg tcacacagat ggctttgtgg gctatcatgg cagcccact    7500 ctttatgtct aacgatttgc ggcatatttc accacaggcc aaagccctgc tgcaagataa    7560
ggacgtcata gcgattaacc aggaccccact gggaaagcag gctaccagc tgagacaggg    7620 cgacaatttt gaggtctggg aaagacctct tagcgggctg gcgtgggccg tagccatgat    7680
taatcgccag gaaattggcg gccctcgctc ttacactatc gcggtcgcca gtctgggcaa    7740
gggagtcgct tgtaaccccg cctgcttcat aactcagttg ctgcccgtga acggaagct    7800 gggcttctat gaatggacta gcagactccg cagtcatatt aatccgactg gtacggtgct    7860
gctgcaactg gagaatacca tgcagatgtc acttaaggat cttctgtgag aacccgggat    7920
ccaagcttca attgtggtca ctcgacaatc aacctctgga ttacaaaatt tgtgaaagat    7980
tgactggtat tcttaactat gttgctcctt ttacgctatg tggatacgct gctttaatgc    8040
ctttgtatca tgctattgct tcccgtatgg ctttcatttt ctcctccttg tataaatcct    8100
ggttgctgtc tctttatgag gagttgtggc ccgttgtcag gcaacgtggc gtggtgtgca    8160
ctgtgtttgc tgacgcaacc cccactggtt ggggcattgc caccacctgt cagctccttt    8220
ccgggacttt cgctttcccc ctccctattg ccacggcgga actcatcgcc gcctgccttg    8280
cccgctgctg acaggggct cggctgttgg gcactgacaa ttccgtggtg ttgtcgggga    8340
agctgacgtc ctttccatgg ctgctcgcct gtgttgccac ctggattctg cgcgggacgt    8400
ccttctgcta cgtcccttcg ccctcaatc cagcggacct tccttcccgc ggcctgctgc    8460
cggctctgcg gcctcttccg cgtcttgcc ttcgccctca gacgagtcgg atctcccttt    8520
gggccgcctc cccgcctgct cgagacctag aaaaacatgg agcaatcaca agtagcaata    8580
cagcagctac caatgctgat tgtgcctggc tagaagcaca agaggaggag gaggtgggtt    8640
ttccagtcac acctcaggta cctttaagac caatgactta caaggcagct gtagatctta    8700 gccactttt aaaagaaaag gggggactgg aagggctaat tcactcccaa cgaagacaag    8760
```

```
atctgctttt tgcttgtact gggtctctct ggttagacca gatctgagcc tgggagctct      8820
ctggctaact agggaaccca ctgcttaagc ctcaataaag cttgccttga gtgcttcaag      8880
tagtgtgtgc ccgtctgttg tgtgactctg gtaactagag atccctcaga ccctttagt      8940 cagtgtggaa aatctctagc agtagtagtt catgtcatct tattattcag tatttataac      9000
ttgcaaagaa atgaatatca gagagtgaga ggacgcgttg gatgcatagc ttgagtattc      9060
tatagtgtca cctaaatagc ttggcgtaat catggtcata gctgtttcct gtgtgaaatt      9120
gttatccgct cacaattcca cacaacatac gagccggaag cataaagtgt aaagcctggg      9180
gtgcctaatg agtgagctaa ctcacattaa ttgcgttgcg ctcactgccc gctttccagt      9240
cgggaaacct gtcgtgccag ctgcattaat gaatcggcca acgcgcgggg agaggcggtt      9300
tgcgtattgg cgctcttcc gcttcctcgc tcactgactc gctgcgctcg tcgttcggc       9360 tgcggcgagc ggtatcagct cactcaaagg cggtaatacg ttatccaca gaatcagggg      9420 ataacgcagg aaagaacatg tgagcaaaag gccagcaaaa ggccaggaac cgtaaaaagg      9480
ccgcgttgct ggcgtttttc cataggctcc gcccccctga cgagcatcac aaaaatcgac      9540
gctcaagtca gaggtggcga aacccgacag gactataaag ataccaggcg tttccccctg      9600
gaagctccct cgtgcgctct cctgttccga ccctgccgct taccggatac ctgtccgcct      9660
ttctcccttc gggaagcgtg gcgctttctc atagctcacg ctgtaggtat ctcagttcgg      9720
tgtaggtcgt tcgctccaag ctgggctgtg tgcacgaacc ccccgttcag cccgaccgct      9780
gcgccttatc cggtaactat cgtcttgagt ccaacccggt aagacacgac ttatcgccac      9840
tggcagcagc cactggtaac aggattagca gagcgaggta tgtaggcggt gctacagagt      9900
tcttgaagtg gtggcctaac tacggctaca ctagaagaac agtatttggt atctgcgctc      9960
tgctgaagcc agttaccttc ggaaaaagag ttggtagctc ttgatccggc aaacaaacca     10020
ccgctggtag cggtggtttt tttgtttgca agcagcagat tacgcgcaga aaaaaggat      10080 ctcaagaaga tcctttgatc ttttctacgg ggtctgacgc tcagtggaac gaaaactcac     10140
gttaagggat tttggtcatg agattatcaa aaaggatctt cacctagatc cttttaaatt     10200
aaaaatgaag ttttaaatca atctaaagta tatatgagta aacttggtct gacagttacc     10260
aatgcttaat cagtgaggca cctatctcag cgatctgtct atttcgttca tccatagttg     10320
cctgactccc cgtcgtgtag ataactacga tacgggaggg cttaccatct ggccccagtg     10380
ctgcaatgat accgcgagac ccacgctcac cggctccaga tttatcagca ataaaccagc     10440
cagccggaag ggccgagcgc agaagtggtc ctgcaacttt atccgcctcc atccagtcta     10500
ttaattgttg ccgggaagct agagtaagta gttcgccagt taatagtttg cgcaacgttg     10560
ttgccattgc tacaggcatc gtggtgtcac gctcgtcgtt tggtatggct tcattcagct     10620
ccggttccca acgatcaagg cgagttacat gatcccccat gttgtgcaaa aaagcggtta     10680
gctccttcgg tcctccgatc gttgtcagaa gtaagttggc cgcagtgtta tcactcatgg     10740
ttatggcagc actgcataat tctcttactg tcatgccatc cgtaagatgc ttttctgtga     10800
ctggtgagta ctcaaccaag tcattctgag aatagtgtat gcggcgaccg agttgctctt     10860
gcccggcgtc aatacgggat aataccgcgc cacatagcag aactttaaaa gtgctcatca     10920
ttggaaaacg ttcttcgggg cgaaaactct caaggatctt accgctgttg agatccagtt     10980
cgatgtaacc cactcgtgca cccaactgat cttcagcatc ttttactttc accagcgttt     11040
ctgggtgagc aaaaacagga aggcaaaatg ccgcaaaaaa gggaataagg gcgacacgga     11100
aatgttgaat actcatactc ttcctttttc aatattattg aagcatttat cagggttatt     11160
```

```
gtctcatgag cggatacata tttgaatgta tttagaaaaa taaacaaata ggggttccgc     11220
gcacatttcc ccgaaaagtg ccacctgatg cggtgtgaaa taccgcacag atgcgtaagg     11280
agaaaatacc gcatcagg                                                  11298

<210> SEQ ID NO 4
<211> LENGTH: 11626
<212> TYPE: DNA
<213> ORGANISM: Artificial Sequence
<220> FEATURE:
<223> OTHER INFORMATION: synthetic vector

<400> SEQUENCE: 4
ccggtgccta gagaaggtgg cgcggggtaa actgggaaag tgatgtcgtg tactggctcc       60 gccttttttcc cgagggtggg ggagaaccgt atataagtgc agtagtcgcc gtgaacgttc     120
```

```
gtctcatgag cggatacata tttgaatgta tttagaaaaa taaacaaata ggggttccgc     11220
gcacatttcc ccgaaaagtg ccacctgatg cggtgtgaaa taccgcacag atgcgtaagg     11280
agaaaatacc gcatcagg                                                  11298

<210> SEQ ID NO 4
<211> LENGTH: 11626
<212> TYPE: DNA
<213> ORGANISM: Artificial Sequence
<220> FEATURE:
<223> OTHER INFORMATION: synthetic vector

<400> SEQUENCE: 4
ccggtgccta gagaaggtgg cgcggggtaa actgggaaag tgatgtcgtg tactggctcc       60
gcctttttcc cgagggtggg ggagaaccgt atataagtgc agtagtcgcc gtgaacgttc      120
tttttcgcaa cgggtttgcc gccagaacac aggtaagtgc cgtgtgtggt tcccgcgggc      180
ctggcctctt tacgggttat ggcccttgcg tgccttgaat tacttccacc tggctgcagt      240
acgtgattct tgatcccgag cttcgggttg aagtgggtg ggagagttcg aggccttgcg       300
cttaaggagc cccttcgcct cgtgcttgag ttgaggcctg gcctgggcgc tggggccgcc      360
gcgtgcgaat ctggtggcac cttcgcgcct gtctcgctgc tttcgataag tctctagcca      420
tttaaaattt tgatgacct gctgcgacgc ttttttttctg gcaagatagt cttgtaaatg      480
cgggccaaga tctgcacact ggtatttcgg ttttggggc gcgggcggc gacggggccc        540 gtgcgtccca gcgcacatgt tcggcgaggc ggggcctgcg agcgcggcca ccgagaatcg      600 gacggggta gtctcaagct ggccggcctg ctctggtgcc tggcctcgcg ccgccgtgta      660
tcgccccgcc ctgggcggca aggctggccc ggtcggcacc agttgcgtga gcggaaagat      720
ggccgcttcc cggccctgct gcaggagct caaaatggag gacgcggcgc tcgggagagc      780
gggcgggtga gtcacccaca caaaggaaaa gggcctttcc gtcctcagcc gtcgcttcat      840
gtgactccac ggagtaccgg gcgccgtcca ggcacctcga ttagttctcg agcttttgga     900
gtacgtcgtc tttaggttgg ggggaggggt tttatgcgat ggagtttccc cacactgagt      960
gggtggagac tgaagttagg ccagcttggc acttgatgta attctccttg gaatttgccc     1020
tttttgagtt tggatcttgg ttcattctca agcctcagac agtggttcaa agttttttttc    1080 ttccatttca ggtgtcgtga ggaattcgct agcgccacca tggagttctc aagccccctct   1140 cgggaagaat gcccaaaacc tctgtcacgg gtgtctatca tggctggatc actgactggc     1200
ctgctgctgc tgcaggccgt gagctgggcc tccggagccc ggccttgcat cccaaagtct    1260
ttcggctaca gctccgtggt gtgcgtgtgc aacgccacct attgtgactc cttcgatccc    1320 cctaccttc ccgccctggg cacattttct cggtacgagt ctacacgcag cggcaggaga     1380
atggagctga gcatgggccc tatccaggcc aatcacaccg aacaggcct gctgctgacc     1440 ctgcagccag agcagaagtt ccagaaggtg aagggctttg gaggagcaat gacagacgca     1500
gccgccctga acatcctggc cctgtcccca cccgcccaga tctgctgct gaagtcctac     1560 ttctctgagg agggcatcgg ctataacatc atcagggtgc ccatggccag ctgcgacttt    1620
tccatcagaa cctacacata tgccgatacc cctgacgatt tccagctgca caattttttcc   1680 ctgccagagg aggatacaaa gctgaagatc ccactgatcc acagggccct gcagctggcc    1740
cagaggcccg tgagcctgct ggccagcccc tggacctccc ctacatggct gaagaccaac    1800
ggcgccgtga atggcaaggg ctctctgaag ggacagccag cgacatcta ccaccagaca     1860 tgggcccgct atttcgtgaa gtttctggat gcctacgccg agcacaagct gcagttctgg     1920
```

```
gccgtgaccg cagagaacga gccttctgcc ggcctgctga gcggctatcc cttccagtgc   1980
ctgggcttta cacctgagca ccagagggac tttatcgcca gagatctggg cccaaccctg   2040
gccaactcca cacaccacaa tgtgcggctg ctgatgctgg acgatcagcg cctgctgctg   2100
cctcactggg ccaaggtggt gctgaccgac ccagaggccg ccaagtacgt gcacggcatc   2160
gccgtgcact ggtatctgga tttcctggca ccagcaaagg ccaccctggg agagacacac   2220
aggctgttcc ctaacaccat gctgtttgcc agcgaggcct gcgtgggctc caagttttgg   2280
gagcagtccg tgcggctggg ctcttgggac aggggcatgc agtactccca ctctatcatc   2340
accaatctgc tgtatcacgt ggtgggctgg acagactgga acctggccct gaatccagag   2400
ggcggcccca actgggtgag aaatttcgtg gatagcccca tcatcgtgga catcaccaag   2460
gatacattct acaagcagcc aatgttttat cacctgggcc acttctctaa gtttatccca   2520
gagggcagcc agagggtggg cctggtggcc agccagaaga cgacctggat gcagtggcc   2580
ctgatgcacc ctgacggctc cgccgtggtg gtggtgctga atcgctctag caaggacgtg   2640
cctctgacca tcaaggaccc cgccgtgggc tttctggaga ccatttcacc cggctattct   2700
attcataccc atctgtggag gaggcagtaa cctgcagggg atccaagctt caattgtggt   2760
cactcgacaa tcaacctctg gattacaaaa tttgtgaaag attgactggt attcttaact   2820
atgttgctcc ttttacgcta tgtggatacg ctgctttaat gcctttgtat catgctattg   2880
cttcccgtat ggctttcatt ttctcctcct tgtataaatc ctggttgctg tctctttatg   2940
aggagttgtg gcccgttgtc aggcaacgtg gcgtggtgtg cactgtgttt gctgacgcaa   3000
cccccactgg ttggggcatt gccaccacct gtcagctcct ttccgggact ttcgctttcc   3060
ccctccctat tgccacggcg gaactcatcg ccgcctgcct tgcccgctgc tggacagggg   3120
ctcggctgtt gggcactgac aattccgtgg tgttgtcggg aagctgacg tcctttccat   3180
ggctgctcgc ctgtgttgcc acctggattc tgcgcgggac gtccttctgc tacgtccctt   3240
cggccctcaa tccagcggac cttcttccc gcggcctgct gccggctctg cggcctcttc   3300
cgcgtcttcg ccttcgccct cagacgagtc ggatctccct ttgggccgcc tccccgcctg   3360
ctcgagacct agaaaaacat ggagcaatca caagtagcaa tacagcagct accaatgctg   3420
attgtgcctg gctagaagca caagaggagg aggaggtggg ttttccagtc acacctcagg   3480
tacctttaag accaatgact tacaaggcag ctgtagatct tagccacttt ttaaaagaaa   3540
agggggggact ggaagggcta attcactccc aacgaagaca agatctgctt tttgcttgta   3600
ctgggtctct ctggttagac cagatctgag cctgggagct ctctggctaa ctagggaacc   3660
cactgcttaa gcctcaataa agcttgcctt gagtgcttca agtagtgtgt gcccgtctgt   3720
tgtgtgactc tggtaactag agatccctca gacccttta gtcagtgtgg aaaatctcta   3780
gcagtagtag ttcatgtcat cttattattc agtatttata acttgcaaag aaatgaatat   3840
cagagagtga gaggacgcgt tggatgcata gcttgagtat tctatagtgt cacctaaata   3900
gcttggcgta atcatggtca tagctgtttc ctgtgtgaaa ttgttatccg ctcacaattc   3960
cacacaacat acgagccgga agcataaagt gtaaagcctg gggtgcctaa tgagtgagct   4020
aactcacatt aattgcgttg cgctcactgc ccgctttcca gtcgggaaac ctgtcgtgcc   4080
agctgcatta atgaatcggc caacgcgcgg ggagaggcgg tttgcgtatt gggcgctctt   4140
ccgcttcctc gctcactgac tcgctgcgct cggtcgttcg gctgcggcga gcggtatcag   4200
ctcactcaaa ggcggtaata cggttatcca cagaatcagg ggataacgca ggaaagaaca   4260
tgtgagcaaa aggccagcaa aaggccagga accgtaaaaa ggccgcgttg ctggcgtttt   4320
```

```
tccataggct ccgcccccct gacgagcatc acaaaaatcg acgctcaagt cagaggtggc    4380
gaaacccgac aggactataa agataccagg cgtttccccc tggaagctcc ctcgtgcgct    4440
ctcctgttcc gaccctgccg cttaccggat acctgtccgc ctttctccct tcgggaagcg    4500
tggcgctttc tcatagctca cgctgtaggt atctcagttc ggtgtaggtc gttcgctcca    4560
agctgggctg tgtgcacgaa ccccccgttc agcccgaccg ctgcgcctta ccggtaact    4620 atcgtcttga gtccaacccg gtaagacacg acttatcgcc actggcagca gccactggta    4680
acaggattag cagagcgagg tatgtaggcg gtgctacaga gttcttgaag tggtggccta    4740
actacggcta cactagaaga acagtatttg gtatctgcgc tctgctgaag ccagttacct    4800
tcggaaaaag agttggtagc tcttgatccg gcaaacaaac caccgctggt agcggtggtt    4860 ttttgtttg caagcagcag attacgcgca gaaaaaagg atctcaagaa gatcctttga    4920
tcttttctac ggggtctgac gctcagtgga acgaaaactc acgttaaggg attttggtca    4980
tgagattatc aaaaggatc ttcacctaga tccttttaaa ttaaaatga gttttaaat    5040 caatctaaag tatatatgag taaacttggt ctgacagtta ccaatgctta atcagtgagg    5100
cacctatctc agcgatctgt ctatttcgtt catccatagt tgcctgactc cccgtcgtgt    5160
agataactac gatacgggag ggcttaccat ctggccccag tgctgcaatg ataccgcgag    5220
acccacgctc accggctcca gatttatcag caataaacca gccagccgga agggccgagc    5280
gcagaagtgg tcctgcaact ttatccgcct ccatccagtc tattaattgt tgccgggaag    5340
ctagagtaag tagttcgcca gttaatagtt tgcgcaacgt tgttgccatt gctacaggca    5400
tcgtggtgtc acgctcgtcg tttggtatgg cttcattcag ctccggttcc caacgatcaa    5460
ggcgagttac atgatccccc atgttgtgca aaaaagcggt tagctccttc ggtcctccga    5520
tcgttgtcag aagtaagttg gccgcagtgt tatcactcat ggttatggca gcactgcata    5580
attctcttac tgtcatgcca tccgtaagat gcttttctgt gactggtgag tactcaacca    5640
agtcattctg agaatagtgt atgcggcgac cgagttgctc ttgcccggcg tcaatacggg    5700
ataataccgc gccacatagc agaactttaa aagtgctcat cattggaaaa cgttcttcgg    5760
ggcgaaaact ctcaaggatc ttaccgctgt tgagatccag ttcgatgtaa cccactcgtg    5820
cacccaactg atcttcagca tcttttactt tcaccagcgt ttctgggtga gcaaaaacag    5880
gaaggcaaaa tgccgcaaaa aagggaataa gggcgacacg gaaatgttga atactcatac    5940
tcttcctttt tcaatattat tgaagcattt atcagggtta ttgtctcatg agcggataca    6000
tatttgaatg tatttagaaa aataaacaaa taggggttcc gcgcacattt ccccgaaaag    6060
tgccacctga tgcggtgtga ataccgcac agatgcgtaa ggagaaaata ccgcatcagg    6120
aaattgtaag cgttaatatt ttgttaaaat tcgcgttaaa ttttgttaa atcagctcat    6180 ttttaacca ataggccgaa atcggcaaaa tcccttataa atcaaaagaa tagaccgaga    6240
tagggttgag tgttgttcca gtttggaaca agagtccact attaaagaac gtggactcca    6300
acgtcaaagg gcgaaaaacc gtctatcagg gcgatggccc actacgtgaa ccatcaccct    6360
aatcaagttt ttggggtcg aggtgccgta agcactaaa tcggaaccct aaagggagcc    6420
cccgatttag agcttgacgg ggaaagccgg cgaacgtggc gagaaaggaa gggaagaaag    6480
cgaaaggagc gggcgctagg gcgctggcaa gtgtagcggt cacgctgcgc gtaaccacca    6540
cacccgccgc gcttaatgcg ccgctacagg gcgcgtccat tcgccattca ggctgcgcaa    6600
ctgttgggaa gggcgatcgg tgcgggcctc ttcgctatta cgccagctgg cgaaggggg    6660 atgtgctgca aggcgattaa gttgggtaac gccagggttt tcccagtcac gacgttgtaa    6720
```

```
aacgacggcc agtgaattgt aatacgactc actatagggc gaattgggcc cgacgtcgca    6780
tgcttggaag ggctaattca ctcccaaaga agacaagata tccttgatct gtggatctac    6840
cacacacaag gctacttccc tgattagcag aactacacac cagggccagg ggtcagatat    6900
ccactgacct ttggatggtg ctacaagcta gtaccagttg agccagataa ggtagaagag    6960
gccaataaag gagagaacac cagcttgtta caccctgtga gcctgcatgg gatggatgac    7020
ccggagagag aagtgttaga gtggaggttt gacagccgcc tagcatttca tcacgtggcc    7080
cgagagctgc atccggagta cttcaagaac tgctgatatc gagcttgcta caagggactt    7140
tccgctgggg actttccagg gaggcgtggc ctgggcggga ctggggagtg gcgagccctc    7200
agatcctgca tataagcagc tgcttttttgc ctgtactggg tctctctggt tagaccagat    7260
ctgagcctgg gagctctctg gctaactagg gaacccactg cttaagcctc aataaagctt    7320
gccttgagtg cttcaagtag tgtgtgcccg tctgttgtgt gactctggta actagagatc    7380
cctcagaccc ttttagtcag tgtggaaaat ctctagcagt ggcgcccgaa cagggacttg    7440
aaagcgaaag ggaaaccaga ggagctctct cgacgcagga ctcggcttgc tgaagcgcgc    7500
acggcaagag gcgaggggcg gcgactggtg agtacgccaa aaattttgac tagcggaggc    7560
tagaaggaga gagatgggtg cgagagcgtc agtattaagc gggggagaat tagatcgcga    7620
tgggaaaaaa ttcggttaag gccaggggga agaaaaaaat ataaattaaa acatatagta    7680
tgggcaagca gggagctaga acgattcgca gttaatcctg gcctgttaga acatcagaa    7740 ggctgtagac aaatactggg acagctacaa ccatcccttc agacaggatc agaagaactt    7800
agatcattat ataatacagt agcaaccctc tattgtgtgc atcaaaggat agagataaaa    7860
gacaccaagg aagctttaga caagatagag gaagagcaaa acaaaagtaa gaccaccgca    7920
cagcaagcgg ccgctgatct tcagacctgg aggaggagat atgagggaca attggagaag    7980
tgaattatat aaatataaag tagtaaaaat tgaaccatta ggagtagcac ccaccaaggc    8040
aaagagaaga gtggtgcaga gagaaaaaag agcagtggga ataggagctt tgttccttgg    8100
gttcttggga gcagcaggaa gcactatggg cgcagcgtca atgacgctga cggtacaggc    8160
cagacaatta ttgtctggta tagtgcagca gcagaacaat ttgctgaggg ctattgaggc    8220
gcaacagcat ctgttgcaac tcacagtctg ggcatcaag cagctccagg caagaatcct    8280
ggctgtggaa agatacctaa aggatcaaca gctcctgggg atttggggtt gctctggaaa    8340
actcatttgc accactgctg tgccttggaa tgctagttgg agtaataaat ctctggaaca    8400
gatttggaat cacacgacct ggatggagtg ggacagagaa attaacaatt acacaagctt    8460
aatacactcc ttaattgaag aatcgcaaaa ccagcaagaa aagaatgaac aagaattatt    8520
ggaattagat aaatgggcaa gtttgtggaa ttggtttaac ataacaaatt ggctgtggta    8580
tataaaatta ttcataatga tagtaggagg cttggtaggt ttaagaatag ttttttgctgt    8640 actttctata gtgaatagag ttaggcaggg atattcacca ttatcgtttc agacccacct    8700
cccaaccccg aggggacccg acaggcccga aggaatagaa gaagaaggtg gagagagaga    8760
cagagacaga tccattcgat tagtgaacgg atctcgacgg gatcgatttt aaaagaaaag    8820
gggggattgg ggggtacagt gcaggggaaa gaatagtaga cataatagca acagacatac    8880
aaactaaaga attacaaaaa caaattacaa aaattcaaaa ttttatcgat aagctttgca    8940
aagatggata agttttttaaa cagagaggaa tctttgcagc taatggacct tctaggtctg    9000
accccgtacg cctcgagaga tctgatcata atcagccata ccacatttgt agaggtttta    9060
cttgctttaa aaaacctccc acacctcccc ctgaacctga aacataaaat gaatgcaatt    9120
```

```
gttgttgtta acttgtttat tgcagcttat aatggttaca aataaggcaa tagcatcaca    9180
aatttcacaa ataaggcatt tttttcactg cattctagtt ttggtttgtc caaactcatc    9240
aatgtatctt atcatgtctg gatctcaaat ccctcggaag ctgcgcctgt cttaggttgg    9300
agtgatacat ttttatcact tttacccgtc tttggattag gcagtagctc tgacggccct    9360
cctgtcttag gttagtgaaa aatgtcactc tcttacccgt cattggctgt ccagcttagc    9420
tcgcagggga ggtggtctgc ctgcaggtta aacagtctc ttttcgtatg agtgcagtga    9480
gtggacgccg ccttcgacct gggctgaaga agttcttttc tcgaacttca gttcgccgga    9540
atacatcatt gcccgcacct gtgtcaggct cttagcgccg atatcctggc atgaatgctg    9600
aattccggcg atcaggtaag gcacgaattt gtgaatactg cccttatcct ggacagctcc    9660
agacacgccc tgtgcgactt tgatcttgtc tgcctcggaa aaatacctgt tctgagagga    9720
cagatgctta tccatggcgt ccagtgaccc catgccccta tatttcttca gtctgaaccc    9780
atcactaaag aagtactcgc cgggggcttc tgtggttgca gccagcaggc tgcccatcat    9840
cactgtgctt gcccccagag ccagggcttt tgcgatgtgg cccacattct gaattccccc    9900
gtcagcgatc actgggactc cgaatctccg ggcatactcg tacaccttgt agacagcagt    9960
tgcctgaggt cgtccacagg ccagcacttc ctgaatgatg cagattgatc cactcccat    10020 tccgaccctc agagcatcca ctcctgcgtc aatcaggttt ttggcctggg ctgcggtcac   10080
gacattgcct ccgatgacct gcagatttgg gtacttgtcc ttaatgtact tgatcatatt   10140
aatctggaag atgctgtttc cctggcttga atccagcacg accacgtcca cccctgcctg   10200
agccagcaga tccaggcgat atttatcgtc ctcgtgtgtg ccaatagcgg ctccacacag   10260
cagctgtttc tttgcgtcct tactagccag agggtaatct cgattttct tcaggtcggt   10320 gcgggcaatg attgccacca gctcatcgtc ttcattcacg ataggcagtt ttcctttctt   10380
agaccgctgc agaatctcgt tggcttcctt cagtgtgatg ccggcaggtg cgaccaccag   10440
atcttcgcgt ttggtcataa tctcttccag aaaacagtca tgctcttcct ccttcaggaa   10500
atcgatgtct cgactagaaa tgattcccac cagtcggctg cccattcgtc cagtatctgt   10560 aatgggatg ccgcaaaatc cgtgcctagc tttggcctcg aacacatcgc ggaccctgtc   10620
cttggggctc aggaccactg ggtcggtgat aaagccctgt tcgtatttct tcaccttct   10680 gacctcattg gcctgaaatt ctggagtgca gttatggtga atgaacccga tcccgcctgt   10740
cagtgccata gcaatggcca tgccagcctc ggtgacagtg tccataggg agctcaccag   10800 gggtgtcttc agggtgattt tcttggtcag ggcagaagtc agatccacct ggtctgcggt   10860
aaaatcaata tagccgggca ggatcaggaa gtcgttgtaa gtcagcccgt ctccacaatt   10920
aaacagctgc tgggcggtca gtccatcatc agggacatag gaagtgcctc cagaaatcag   10980
gtagtcggcc atggtggcgc tagccctggg gagagaggtc ggtgattcgg tcaacgaggg   11040
agccgactgc cgacgtgcgc tccggaggct tgcagaatgc ggaacaccgc gcgggcagga   11100
acagggccca cactaccgcc ccacaccccg cctcccgcac cgccccttcc cggccgctgc   11160
tctcggcgcg ccccgctgag cagccgctat tggccacagc ccatcgcggt cggcgcgctg   11220
ccattgctcc ctgcgctgt ccgtctgcga gggtactagt gagacgtgcg gcttccgttt   11280
gtcacgtccg gcacgccgcg aaccgcaagg aaccttcccg acttaggggc ggagcaggaa   11340
gcgtcgccgg ggggcccaca agggtagcgg cgaagatccg ggtgacgctg cgaacggacg   11400
tgaagaatgt gcgagaccca gggtcggcgc cgctgcgttt cccggaacca cgcccagagc   11460
agccgcgtcc ctgcgcaaac ccagggctgc caaggaaaag gcgcaacccc aaccccgtgg   11520
```
ttaattaagg tgaaaggagt gggaattggc tccggtgccc gtcagtgggc agagcgcaca 11580
tcgcccacag tccccgagaa gttgggggga ggggtcggca attgaa 11626

<210> SEQ ID NO 5
<211> LENGTH: 1290
<212> TYPE: DNA
<213> ORGANISM: Artificial Sequence
<220> FEATURE:
<223> OTHER INFORMATION: synthetic

<400> SEQUENCE: 5
atgcaacttc gaaacccaga gctccacctc ggatgtgccc ttgctctgag gttcctggcg 60
ctggtgtctt gggatatacc cggagcacgc gctctggaca cgggctggc ccggactcca 120 accatgggtt ggctccattg gaaaggtttt atgtgcaact ggactgcca ggaagaaccc 180 gactcctgta tttccgagaa actcttcatg agatggccg agctgatggt tagcgaaggc 240
tggaaggatg ccggttatga atacttgtgt atcgacgatt gttggatggc tcccagcgg 300 gacagtgaag gacgactcca ggcagatccg caacggttcc ctcatggcat acggcagctc 360
gccaattacg tgcacagcaa gggttttgaag ctggggatat atgctgacgt gggcaacaaa 420
acctgtgctg gtttccccgg cagcttcggc tactatgata tagatgcaca accttcgct 480 gattggggcg tggacctgct taaatttgac ggctgttact gcgacagctt ggaaaacctc 540
gccgatggat ataaacacat gagccttgca ctcaatcgga ctggccggag cattgtctac 600
tcttgcgagt ggccattgta catgtggcct ttccagaagc ctaactatac ggagattaga 660
cagtattgta atcactggag aaactttgca gatatcgacg actcatggaa gtccatcaaa 720
tctattctgg actggacttc attcaatcag gagcgcatcg tcgatgttgc cggtccaggt 780
ggatggaacg accctgacat gctcgtaatt gggaatttcg actgtcctg gaatcagcag 840 gtcacacaga tggctttgtg ggctatcatg gcagccccac tctttatgtc taacgatttg 900
cggcatattt caccacaggc caaagccctg ctgcaagata aggacgtcat agcgattaac 960
caggacccac tgggaaagca gggctaccag ctgagacagg gcgacaattt tgaggtctgg 1020
gaaagacctc ttagcgggct ggcgtgggcc gtagccatga ttaatcgcca ggaaattggc 1080
ggccctcgct cttacactat cgcggtcgcc agtctgggca agggagtcgc ttgtaacccc 1140
gcctgcttca taactcagtt gctgcccgtg aaacggaagc tgggcttcta tgaatggact 1200
agcagactcc gcagtcatat taatccgact ggtacggtgc tgctgcaact ggagaatacc 1260
atgcagatgt cacttaagga tcttctgtga 1290

<210> SEQ ID NO 6
<211> LENGTH: 1611
<212> TYPE: DNA
<213> ORGANISM: Artificial Sequence
<220> FEATURE:
<223> OTHER INFORMATION: synthetic

<400> SEQUENCE: 6
atggagttct caagcccctc tcgggaagaa tgcccaaaac ctctgtcacg ggtgtctatc 60
atggctggat cactgactgg cctgctgctg ctgcaggccg tgagctgggc ctccggagcc 120
cggccttgca tcccaaagtc tttcggctac agctccgtgg tgtgcgtgtg caacgccacc 180
tattgtgact ccttcgatcc ccctaccttt cccgccctgg cacattttc tcggtacgag 240 tctacacgca gcggcaggag aatggagctg agcatgggcc ctatccaggc caatcacacc 300
ggaacaggcc tgctgctgac cctgcagcca gagcagaagt tccagaaggt gaagggcttt 360

| | |
|---|---|
| ggaggagcaa tgacagacgc agccgccctg aacatcctgg ccctgtcccc acccgcccag | 420 |
| aatctgctgc tgaagtccta cttctctgag gagggcatcg gctataacat catcagggtg | 480 |
| cccatggcca gctgcgactt ttccatcaga acctacacat atgccgatac ccctgacgat | 540 |
| ttccagctgc acaattttc cctgccagag gaggatacaa agctgaagat cccactgatc | 600 |
| cacagggccc tgcagctggc ccagaggccc gtgagcctgc tggccagccc ctggacctcc | 660 |
| cctacatggc tgaagaccaa cggcgccgtg aatggcaagg ctctctgaa gggacagcca | 720 |
| ggcgacatct accaccagac atgggcccgc tatttcgtga gtttctgga tgcctacgcc | 780 |
| gagcacaagc tgcagttctg ggccgtgacc gcagagaacg agccttctgc cggcctgctg | 840 |
| agcggctatc ccttccagtg cctgggcttt acacctgagc accagaggga ctttatcgcc | 900 |
| agagatctgg gcccaaccct ggccaactcc acacaccaca atgtgcggct gctgatgctg | 960 |
| gacgatcagc gcctgctgct gcctcactgg gccaaggtgg tgctgaccga cccagaggcc | 1020 |
| gccaagtacg tgcacggcat cgccgtgcac tggtatctgg atttcctggc accagcaaag | 1080 |
| gccaccctgg gagagacaca caggctgttc cctaacacca tgctgtttgc cagcgaggcc | 1140 |
| tgcgtgggct ccaagttttg ggagcagtcc gtgcggctgg gctcttggga caggggcatg | 1200 |
| cagtactccc actctatcat caccaatctg ctgtatcacg tggtgggctg acagactggg | 1260 |
| aacctggccc tgaatccaga gggcggcccc aactgggtga gaaatttcgt ggatagcccc | 1320 |
| atcatcgtgg acatccaccaa ggatacattc tacaagcagc caatgttta tcacctgggc | 1380 |
| cacttctcta gtttatccc agagggcagc cagagggtgg gcctggtggc cagccagaag | 1440 |
| aacgacctgg atgcagtggc cctgatgcac cctgacggct ccgccgtggt ggtggtgctg | 1500 |
| aatcgctcta gcaaggacgt gcctctgacc atcaaggacc ccgccgtggg ctttctggag | 1560 |
| accatttcac ccggctattc tattcatacc tatctgtgga ggaggcagta a | 1611 |

<210> SEQ ID NO 7
<211> LENGTH: 1545
<212> TYPE: DNA
<213> ORGANISM: Artificial Sequence
<220> FEATURE:
<223> OTHER INFORMATION: synthetic

<400> SEQUENCE: 7

| | |
|---|---|
| atggccgact acctgatttc tggaggcact tcctatgtcc ctgatgatgg actgaccgcc | 60 |
| cagcagctgt ttaattgtgg agacgggctg acttacaacg acttcctgat cctgcccggc | 120 |
| tatattgatt ttaccgcaga ccaggtggat ctgacttctg ccctgaccaa gaaaatcacc | 180 |
| ctgaagacac ccctggtgag ctcccctatg acactgtca ccgaggctgg catggccatt | 240 |
| gctatggcac tgacaggcgg gatcgggttc attcaccata actgcactcc agaatttcag | 300 |
| gccaatgagg tcagaaaggt gaagaaatac gaacagggct ttatcaccga cccagtggtc | 360 |
| ctgagcccca aggacagggt ccgcgatgtg ttcgaggcca agctaggca cggattttgc | 420 |
| ggcatcccca ttacagatac tggacgaatg ggcagccgac tggtgggaat catttctagt | 480 |
| cgagacatcg atttcctgaa ggaggaagag catgactgtt ttctggaaga gattatgacc | 540 |
| aaacgcgaag atcggtggt cgcacctgcc ggcatcacac tgaaggaagc caacgagatt | 600 |
| ctgcagcggt ctaagaaagg aaaactgcct atcgtgaatg aagacgatga gctggtggca | 660 |
| atcattgccc gcaccgacct gaagaaaat cgagattacc ctctggctag taaggacgca | 720 |
| aagaaacagc tgctgtgtgg agccgctatt ggcacacacg aggacgataa atatcgcctg | 780 |
| gatctgctgg ctcaggcagg ggtggacgtg gtcgtgctgg attcaagcca gggaaacagc | 840 |

```
atcttccaga ttaatatgat caagtacatt aaggacaagt acccaaatct gcaggtcatc    900
ggaggcaatg tcgtgaccgc agcccaggcc aaaaacctga ttgacgcagg agtggatgct    960
ctgagggtcg gaatggggag tggatcaatc tgcatcattc aggaagtgct ggcctgtgga   1020
cgacctcagg caactgctgt ctacaaggta tacgagtatg cccggagatt cggagtccca   1080
gtgatcgctg acgggggaat tcagaatgtg gccacatcg caaaagccct ggctctgggg   1140
gcaagcacag tgatgatggg cagcctgctg gctgcaacca cagaagcccc cggcgagtac   1200
ttctttagtg atgggttcag actgaagaaa tatagggca tggggtcact ggacgccatg   1260
gataagcatc tgtcctctca gaacaggtat ttttccgagg cagacaagat caaagtcgca   1320
cagggcgtgt ctggagctgt ccaggataag ggcagtattc acaaattcgt gccttacctg   1380
atcgccggaa ttcagcattc atgccaggat atcggcgcta agagcctgac acaggtgcgg   1440
gcaatgatgt attccggcga actgaagttc gagaaaagaa cttcttcagc ccaggtcgaa   1500
ggcggcgtcc actcactgca ctcatacgaa aagagactgt tctaa            1545

<210> SEQ ID NO 8
<211> LENGTH: 1188
<212> TYPE: DNA
<213> ORGANISM: Artificial Sequence
<220> FEATURE:
<223> OTHER INFORMATION: synthetic

<400> SEQUENCE: 8
atgccgggcc ggagttgcgt cgccttagtc ctcctggctg ccgccgtcag ctgtgccgtc     60
gcgcagcacg cgccgccgtg dacagaggac tgcagaaaat caacctatcc tccttcagga    120
ccaacgtaca gaggtgcagt tccatggtac accataaatc ttgacttacc accctacaaa    180
agatggcatg aattgatgct tgacaaggca ccagtgctaa aggttatagt gaattctctg    240
aagaatatga taaatacatt cgtgccaagt ggaaaaatta tgcaggtggt ggatgaaaaa    300
ttgcctggcc tacttggcaa ctttcctggc ccttttgaag aggaaatgaa gggtattgcc    360
gctgttactg atatacctt aggagagatt atttcattca atattttta tgaattattt    420 accatttgta cttcaatagt agcagaagac aaaaaaggtc atctaataca tgggagaaac    480
atggattttg gagtatttct tgggtggaac ataaataatg atacctgggt cataactgag    540 caactaaaaac ctttaacagt gaatttggat ttccaaagaa acaacaaaac tgtcttcaag    600
gcttcaagct ttgctggcta tgtgggcatg ttaacaggat caaaccagg actgttcagt    660 cttacactga tgaacgtttt cagtataaat ggtggttatc tgggtattct agaatggatt    720
ctgggaaaga aagatgtcat gtggataggg ttcctcacta gaacagttct ggaaaatagc    780
acaagttatg aagaagccaa gaattattg ccaagacca agatattggc cccagcctac    840
tttatcctgg gaggcaacca gtctggggaa ggttgtgtga ttacacgaga cagaaaggaa    900
tcattggatg tatatgaact cgatgctaag cagggtagag gtatgtggt acaaacaaat    960 tatgaccgtt ggaaacatcc cttcttcctt gatgatcgca gaacgcctgc aaagatgtgt   1020
ctgaaccgca ccagccaaga gaatatctca tttgaaacca tgtatgatgt cctgtcaaca   1080
aaacctgtcc tcaacaagct gaccgtatac acaaccttga tagatgttac caaaggtcaa   1140
ttcgaaactt acctgcggga ctgccctgac ccttgtatag gttggtga           1188

<210> SEQ ID NO 9
<211> LENGTH: 2859
<212> TYPE: DNA
<213> ORGANISM: Artificial Sequence
```

<220> FEATURE:
<223> OTHER INFORMATION: synthetic

<400> SEQUENCE: 9

| | | | | | |
|---|---|---|---|---|---|
| atgggcgtga | ggcaccccc | ttgctctcac | aggctgctgg | ccgtgtgcgc | actggtgagc | 60 |
| ctggccaccg | ccgccctgct | gggccacatc | ctgctgcacg | acttcctgct | ggtgcccagg | 120 |
| gagctgtccg | gcagctcccc | agtgctggag | gagacccacc | cagcacacca | gcagggcgcc | 180 |
| tctcggccag | gccccgcga | tgcacaggca | cacccaggcc | ggccccgcgc | cgtgccaacc | 240 |
| cagtgcgacg | tgccacccaa | cagccggttt | gactgtgccc | ccgataaggc | catcacacag | 300 |
| gagcagtgcg | aggccagggg | ctgctgttat | atccctgcaa | agcagggcct | ccagggcgcc | 360 |
| cagatgggac | agccatggtg | tttctttcct | ccatcttacc | ccagctataa | gctggagaat | 420 |
| ctgtctagct | ccgagatggg | ctacacagcc | accctgacaa | gaaccacacc | aacattcttt | 480 |
| cccaaggaca | tcctgaccct | gcggctggac | gtgatgatgg | agacagagaa | ccgcctgcac | 540 |
| ttcaccatca | aggaccccgc | caataggaga | tatgaggtgc | ctctggagac | ccacacgtg | 600 |
| cactctcggg | ccctagccc | actgtactcc | gtggagttct | ctgaggagcc | atttggcgtg | 660 |
| atcgtgcggc | gccagctgga | tggacgcgtg | ctgctgaaca | ccacagtggc | ccccctgttc | 720 |
| tttgccgacc | agttcctcca | gctgagcaca | tccctgccct | cccagtatat | caccggcctg | 780 |
| gccgagcacc | tgtctcctct | gatgctgtct | accagctgga | caaggatcac | cctgtggaac | 840 |
| agagacctgg | caccaacccc | tggcgcaaat | ctgtacggca | gccaccctt | ctatctggcc | 900 |
| ctggaggatg | gaggctccgc | ccacggcgtg | tttctgctga | actctaatgc | catggacgtg | 960 |
| gtgctccagc | caagccccgc | cctgtcctgg | cggtctaccg | gcggcatcct | ggacgtgtac | 1020 |
| atcttcctgg | gccctgagcc | aaagtccgtg | gtgcagcagt | acctggacgt | ggtgggctat | 1080 |
| cctttcatgc | ccccttactg | gggactggga | tttcacctgt | gccgctgggg | ctattctagc | 1140 |
| acagccatca | cccggcaggt | ggtggagaac | atgacccgcg | cccactttcc | actggatgtg | 1200 |
| cagtggaatg | acctggatta | catggactcc | aggagagact | tcaccttcaa | caaggacggc | 1260 |
| ttcagggatt | ttcccgccat | ggtgcaggag | ctgcaccagg | cggccggcg | ctacatgatg | 1320 |
| atcgtggacc | ccgccatctc | ctctagcgga | cctgccggca | gctacagacc | atatgacgag | 1380 |
| ggcctgagga | gaggcgtgtt | catcacaaac | gagaccggcc | agcctctgat | cggcaaggtc | 1440 |
| tggccaggct | ccaccgcctt | cccagacttc | accaatccaa | ccgccctggc | ctggtgggag | 1500 |
| gacatggtgg | ccgagttcca | cgaccaggtg | ccttttgatg | catgtggat | cgacatgaac | 1560 |
| gagccatcta | atttcatcag | gggcagcgag | gacggctgcc | ccaacaatga | gctggagaac | 1620 |
| ccaccatatg | tgcctggcgt | ggtgggaggc | accctccagg | cagcaaccat | ctgtgcctcc | 1680 |
| tctcaccagt | ttctgtctac | acactataac | ctgcacaatc | tgtacggact | gaccgaggca | 1740 |
| atcgccagcc | acagagccct | ggtgaaggcc | aggggcacaa | gacccttcgt | gatctccagg | 1800 |
| tctacctttg | ccggacacgg | cagatacgca | ggacactgga | ccggcgacgt | gtggagcagc | 1860 |
| tgggagcagc | tggcctctag | cgtgccagag | atcctccagt | tcaacctgct | gggcgtgccc | 1920 |
| ctggtgggag | cagacgtgtg | cggctttctg | ggcaatacat | ccgaggagct | gtgcgtgagg | 1980 |
| tggacccagc | tgggagcctt | ctatcccttc | atgcgcaacc | acaatagcct | gctgtccctg | 2040 |
| cctcaggagc | catacagctt | ctccgagcct | gcacagcagg | caatgaggaa | ggccctgaca | 2100 |
| ctgcgctatg | ccctgctgcc | acacctgtac | acctgtttc | accaggcaca | cgtggcagga | 2160 |
| gagacagtgg | cccggcccct | gttcctggag | tttcctaagg | attcctctac | ctggacagtg | 2220 |

| | |
|---|---:|
| gaccaccagc tgctgtgggg agaggccctg ctgatcaccc ccgtgctcca ggcaggcaag | 2280 |
| gcagaggtga caggctattt ccctctgggc acatggtacg acctccagac cgtgccagtg | 2340 |
| gaggccctgg gcagcctgcc tccaccacct gccgccccc gcgagcctgc catccactcc | 2400 |
| gagggacagt gggtgacact gccagcacct ctggacacca tcaacgtgca cctgagggcc | 2460 |
| ggctatatca tcccctcca gggccctggc ctgaccacaa ccgagtccag acagcagcca | 2520 |
| atggccctgg ccgtggccct gaccaaggga ggcgaggcca ggggcgagct gttctgggac | 2580 |
| gatggcgagt ctctggaggt gctggagaga ggcgcctaca cacaggtcat cttcctggcc | 2640 |
| aggaacaata caatcgtgaa tgagctggtg agagtgacct ctgagggagc aggactccag | 2700 |
| ctccagaagg tgacagtgct gggagtggca accgcaccac agcaggtgct gagcaacggc | 2760 |
| gtgcccgtga gcaatttcac atactcccct gataccaagg tgctggacat ctgcgtgagc | 2820 |
| ctgctgatgg gcgagcagtt tctggtgtcc tggtgttga | 2859 |

<210> SEQ ID NO 10
<211> LENGTH: 1545
<212> TYPE: DNA
<213> ORGANISM: Artificial Sequence
<220> FEATURE:
<223> OTHER INFORMATION: synthetic

<400> SEQUENCE: 10

| | |
|---|---:|
| ttagaacagt ctcttttcgt atgagtgcag tgagtggacg ccgccttcga cctgggctga | 60 |
| agaagttctt ttctcgaact tcagttcgcc ggaatacatc attgcccgca cctgtgtcag | 120 |
| gctcttagcg ccgatatcct ggcatgaatg ctgaattccg gcgatcaggt aaggcacgaa | 180 |
| tttgtgaata ctgcccttat cctggacagc tccagacacg ccctgtgcga ctttgatctt | 240 |
| gtctgcctcg gaaaaatacc tgttctgaga ggacagatgc ttatccatgg cgtccagtga | 300 |
| ccccatgccc ctatatttct tcagtctgaa cccatcacta agaagtact cgccggggc | 360 |
| ttctgtggtt gcagccagca ggctgcccat catcactgtg cttgccccca gagccagggc | 420 |
| ttttgcgatg tggcccacat tctgaattcc cccgtcagcg atcactggga ctccgaatct | 480 |
| ccgggcatac tcgtacacct tgtagacagc agttgcctga ggtcgtccac aggccagcac | 540 |
| ttcctgaatg atgcagattg atccactccc cattccgacc ctcagagcat ccactcctgc | 600 |
| gtcaatcagg ttttggcct gggctgcggt cacgacattg cctccgatga cctgcagatt | 660 |
| tgggtacttg tccttaatgt acttgatcat attaatctgg aagatgctgt ttccctggct | 720 |
| tgaatccagc acgaccacgt ccaccctgc ctgagccagc agatccaggc gatatttatc | 780 |
| gtcctcgtgt gtgccaatag cggctccaca cagcagctgt ttctttgcgt ccttactagc | 840 |
| cagagggtaa tctcgatttt tcttcaggtc ggtgcgggca atgattgcca ccagctcatc | 900 |
| gtcttcattc acgataggca gttttccttt cttagaccgc tgcagaatct cgttggcttc | 960 |
| cttcagtgtg atgccggcag gtgcgaccac cagatcttcg cgtttggtca taatctcttc | 1020 |
| cagaaaacag tcatgctctt cctccttcag gaaatcgatg tctcgactag aaatgattcc | 1080 |
| caccagtcgg ctgcccattc gtccagtatc tgtaatgggg atgccgcaaa atccgtgcct | 1140 |
| agctttggcc tcgaacacat cgcggaccct gtccttgggg tcaggacca ctgggtcggt | 1200 |
| gataaagccc tgttcgtatt tcttcacctt tctgacctca ttggcctgaa attctggagt | 1260 |
| gcagttatgg tgaatgaacc cgatcccgcc tgtcagtgcc atagcaatgg ccatgccagc | 1320 |
| ctcggtgaca gtgtccatag gggagctcac caggggtgtc ttcagggtga ttttcttggt | 1380 |
| cagggcagaa gtcagatcca cctggtctgc ggtaaaatca atatagccgg gcaggatcag | 1440 |

| | |
|---|---:|
| gaagtcgttg taagtcagcc cgtctccaca attaaacagc tgctgggcgg tcagtccatc | 1500 |
| atcagggaca taggaagtgc ctccagaaat caggtagtcg gccat | 1545 |

<210> SEQ ID NO 11
<211> LENGTH: 4405
<212> TYPE: DNA
<213> ORGANISM: Artificial Sequence
<220> FEATURE:
<223> OTHER INFORMATION: synthetic

<400> SEQUENCE: 11

| | |
|---|---:|
| gaattcgtcg acgccgccac catgcaaata gagctctcca cctgcttctt tctgtgcctt | 60 |
| ttgcgattct gctttagtgc caccagaaga tactacctgg gtgcagtgga actgtcatgg | 120 |
| gactatatgc aaagtgatct cggtgagctg cctgtggacg caagatttcc tcctagagtg | 180 |
| ccaaaatctt ttccattcaa cacctcagtc gtgtacaaaa agactctgtt tgtagaattc | 240 |
| acggatcacc ttttcaacat cgctaagcca aggccaccct ggatgggtct gctaggtcct | 300 |
| accatccagg ctgaggttta tgatacatgt gtcattacac ttaagaacat ggcttcccat | 360 |
| cctgtcagtc ttcatgctgt tggtgtatcc tactggaaag cttctgaggg agctgaatat | 420 |
| gatgatcaga ccagtcaaag ggagaaagaa gatgataaag tcttccctgg tggaagccat | 480 |
| acatatgtct ggcaggtcct gaaagagaat ggtccaatgg cctctgaccc actgtgcctt | 540 |
| acctactcat atctttctca gtggaccctg gtaaaagact tgaattcagg cctcattgga | 600 |
| gccctactag tatgtagaga agggagtctg gccaaggaaa agacacagac cttgcacaaa | 660 |
| tttatactac ttttgctgt atttgatgaa gggaaaagtt ggcactcaga aacaaagaac | 720 |
| tccttgatgc aggataggga tgctgcatct gctcgggcct ggcctaaaat gcacacagtc | 780 |
| aatggttatg taaacaggtc tctgccaggt ctgattggat gccacaggaa atcagtctat | 840 |
| tggcatgtga ttggaatggg caccactcct gaagtgcact caatattcct cgaaggtcac | 900 |
| acatttcttg tgaggaacca tcgccaggcg tccttggaaa tctcgccaat aactttcctt | 960 |
| actgctcaaa cactcttgat ggaccttgga cagtttctac tgttttgtca tatctcttcc | 1020 |
| caccaacatg atggcatgga agcttatgtc aaagtagaca gctgtccaga ggaaccccaa | 1080 |
| ctacgaatga aaaataatga agaagcggaa gactatgatg atgatcttac tgattctgaa | 1140 |
| atggatgtgg tcaggtttga tgatgacaac tctccttcct ttatccaaat tcgctcagtt | 1200 |
| gccaagaagc atcctaaaac ttgggtacat tacattgctg ctgaagagga ggactgggac | 1260 |
| tatgctccct tagtcctcgc ccccgatgac agaagttata aaagtcaata tttgaacaat | 1320 |
| ggccctcagc ggattggtag gaagtacaaa aaagtccgat ttatggcata cacagatgaa | 1380 |
| accttttaaga ctcgtgaagc tattcagcat gaatcaggaa tcttgggacc tttactttat | 1440 |
| ggggaagttg gagacacact gttgattata tttaagaatc aagcaagcag accatataac | 1500 |
| atctaccctc acggaatcac tgatgtccgt cctttgtatt caaggagatt accaaaaggt | 1560 |
| gtaaaacatt tgaaggattt tccaattctg ccaggagaaa tattcaaata taatggaca | 1620 |
| gtgactgtag aagatgggcc aactaaatca gatcctcggt gcctgacccg ctattactct | 1680 |
| agtttcgtta atatggagag agatctagct tcaggactca ttggccctct cctcatctgc | 1740 |
| tacaaagaat ctgtagatca agaggaaac cagataatgt cagacaagag gaatgtcatc | 1800 |
| ctgttttctg tatttgatga aaccgaagc tggtacctca cagagaatat acaacgcttt | 1860 |
| ctccccaatc cagctggagt gcagcttgag gatccagagt tccaagcctc caacatcatg | 1920 |
| cacagcatca atggctatgt ttttgatagt ttgcagttgt cagtttgttt gcatgaggtg | 1980 |

```
gcatactggt acattctaag cattggagca cagactgact tcctttctgt cttcttctct    2040
ggatatacct tcaaacacaa aatggtctat gaagacacac tcaccctatt cccattctca    2100
ggagaaactg tcttcatgtc gatggaaaac ccaggtctat ggattctggg gtgccacaac    2160
tcagactttc ggaacagagg catgaccgcc ttactgaagg tttctagttg tgacaagaac    2220
actggtgatt attacgagga cagttatgaa gatatttcag catacttgct gagtaaaaac    2280
aatgccattg aaccaagaag cttctctcaa aacccaccag tcttgaaacg ccatcaacgg    2340
gaaataactc gtactactct tcagtcagat caagaggaaa ttgactatga tgataccata    2400
tcagttgaaa tgaagaagga agattttgac atttatgatg aggatgaaaa tcagagcccc    2460
cgcagctttc aaagaaaac acgacactat tttattgctg cagtggagag gctctgggat    2520
tatgggatga gtagctcccc acatgttcta agaaacaggg ctcagagtgg cagtgtccct    2580
cagttcaaga aagttgtttt ccaggaattt actgatggct cctttactca gcccttatac    2640
cgtggagaac taaatgaaca tttgggactc ctggggccat atataagagc agaagttgaa    2700
gataatatca tggtaacttt cagaaatcag gcctctcgtc cctattcctt ctattctagc    2760
cttatttctt atgaggaaga tcagaggcaa ggagcagaac ctagaaaaaa ctttgtcaag    2820
cctaatgaaa ccaaaactta cttttggaaa gtgcaacatc atatggcacc cactaaagat    2880
gagtttgact gcaaagcctg ggcttatttc tctgatgttg acctggaaaa agatgtgcac    2940
tcaggcctga ttggacccct tctggtctgc cacactaaca cactgaaccc tgctcatggg    3000
agacaagtga cagtacagga atttgctctg tttttcacca tctttgatga gaccaaaagc    3060
tggtacttca ctgaaaatat ggaagaaaac tgcagggctc cctgcaatat ccagatggaa    3120
gatcccactt ttaaagagaa ttatcgcttc catgcaatca atggctacat aatggataca    3180
ctacctggct tagtaatggc tcaggatcaa aggattcgat ggtatctgct cagcatgggc    3240
agcaatgaaa acatccattc tattcatttc agtggacatg tgttcactgt acgaaaaaaa    3300
gaggagtata aaatggcact gtacaatctc tatccaggtg ттттгagac agtggaaatg    3360
ttaccatcca aagctggaat ttggcgggtg gaatgcctta ttggcgagca tctacatgct    3420
gggatgagca cactttttct ggtgtacagc aataagtgtc agactcccct gggaatggct    3480
tctggacaca ttagagattt tcagattaca gcttcaggac aatatggaca gtgggcccca    3540
aagctggcca gacttcatta ttccggatca atcaatgcct ggagcaccaa ggagcccttt    3600
tcttggatca aggtggatct gttggcacca atgattattc acggcatcaa gacccagggt    3660
gcccgtcaga agttctccag cctctacatc tctcagttta tcatcatgta tagtcttgat    3720
gggaagaagt ggcagactta tcgaggaaat tccactggaa ccttaatggt cttctttggc    3780
aatgtggatt catctgggat aaaacacaat atttttaacc ctccaattat tgctcgatac    3840
atccgtttgc acccaactca ттататagcatт cgcagcactc ttcgcatgga gttgatgggc    3900
tgtgatttaa atagttgcag catgccatt ggaатggaга gtaaagcaat atcagatgca    3960
cagattactg cttcatccta ctttaccaat atgtttgcca cctggtctcc ttcaaaagct    4020
cgacttcacc tccaagggag gagtaatgcc tggagacctc aggtgaataa tccaaaagag    4080
tggctgcaag tggacttcca aagacaatg aaaгтcacag gagtaactac tcagggagta    4140
aaatctctgc ttaccagcat gtatgtgaag gagttcctca tctccagcag tcaagatggc    4200
catcagtgga ctctctttt tcagaatggc aaagtaaagg ttttcaggg aaatcaagac    4260
tccttcacac ctgtggtgaa ctctctagac ccaccgttac tgactcgcta ccttcgaatt    4320
```

| cacccccaga gttgggtgca ccagattgcc ctgaggatgg aggttctggg ctgcgaggca | 4380 |
| caggacctct actgacccgg gatcc | 4405 |

<210> SEQ ID NO 12
<211> LENGTH: 14388
<212> TYPE: DNA
<213> ORGANISM: Artificial Sequence
<220> FEATURE:
<223> OTHER INFORMATION: synthetic

<400> SEQUENCE: 12

| gatccaagct tcaattgtgg tcactcgaca atcaacctct ggattacaaa atttgtgaaa | 60 |
| gattgactgg tattcttaac tatgttgctc cttttacgct atgtggatac gctgctttaa | 120 |
| tgcctttgta tcatgctatt gcttcccgta tggctttcat tttctcctcc ttgtataaat | 180 |
| cctggttgct gtctctttat gaggagttgt ggcccgttgt caggcaacgt ggcgtggtgt | 240 |
| gcactgtgtt tgctgacgca accccactg gttgggcat tgccaccacc tgtcagctcc | 300 |
| tttccgggac tttcgctttc cccctcccta ttgccacggc ggaactcatc gccgcctgcc | 360 |
| ttgcccgctg ctggacaggg gctcggctgt tgggcactga caattccgtg gtgttgtcgg | 420 |
| ggaagctgac gtccttttcca tggctgctcg cctgtgttgc cacctggatt ctgcgcggga | 480 |
| cgtccttctg ctacgtccct tcggccctca atccagcgga ccttccttcc cgcggcctgc | 540 |
| tgccggctct gcggcctctt ccgcgtcttc gccttcgccc tcagacgagt cggatctccc | 600 |
| tttgggccgc ctccccgcct gctcgagacc tagaaaaaca tggagcaatc acaagtagca | 660 |
| atacagcagc taccaatgct gattgtgcct ggctagaagc acaagaggag gaggaggtgg | 720 |
| gttttccagt cacacctcag gtaccttta accaatgac ttacaaggca gctgtagatc | 780 |
| ttagccactt tttaaaagaa aagggggac tggaagggc aattcactcc caacgaagac | 840 |
| aagatctgct ttttgcttgt actgggtctc tctggttaga ccagatctga gcctgggagc | 900 |
| tctctggcta actagggaac ccactgctta agcctcaata agcttgcct tgagtgcttc | 960 |
| aagtagtgtg tgcccgtctg ttgtgtgact ctggtaacta gagatccctc agacccttt | 1020 |
| agtcagtgtg gaaaatctct agcagtagta gttcatgtca tcttattatt cagtatttat | 1080 |
| aacttgcaaa gaaatgaata tcagagagtg agaggacgcg ttggatgcat agcttgagta | 1140 |
| ttctatagtg tcacctaaat agcttggcgt aatcatggtc atagctgttt cctgtgtgaa | 1200 |
| attgttatcc gctcacaatt ccacacaaca tacgagccgg aagcataaag tgtaaagcct | 1260 |
| ggggtgccta atgagtgagc taactcacat taattgcgtt gcgctcactg cccgctttcc | 1320 |
| agtcgggaaa cctgtcgtgc cagctgcatt aatgaatcgg ccaacgcgcg gggagaggcg | 1380 |
| gtttgcgtat tgggcgctct tccgcttcct cgctcactga ctcgctgcgc tcggtcgttc | 1440 |
| ggctgcggcg agcggtatca gctcactcaa aggcggtaat acggttatcc acagaatcag | 1500 |
| gggataacgc aggaaagaac atgtgagcaa aaggccagca aaaggccagg aaccgtaaaa | 1560 |
| aggccgcgtt gctggcgttt ttccataggc tccgcccccc tgacgagcat cacaaaaatc | 1620 |
| gacgctcaag tcagaggtgg cgaaacccga caggactata agataccag gcgtttcccc | 1680 |
| ctggaagctc cctcgtgcgc tctcctgttc cgaccctgcc gcttaccgga tacctgtccg | 1740 |
| cctttctccc ttcgggaagc gtggcgcttt ctcatagctc acgctgtagg tatctcagtt | 1800 |
| cggtgtaggt cgttcgctcc aagctgggct gtgtgcacga accccccgtt cagcccgacc | 1860 |
| gctgcgcctt atccggtaac tatcgtcttg agtccaaccc ggtaagacac gacttatcgc | 1920 |
| cactggcagc agccactggt aacaggatta gcagagcgag gtatgtaggc ggtgctacag | 1980 |

```
agttcttgaa gtggtggcct aactacggct acactagaag aacagtattt ggtatctgcg    2040
ctctgctgaa gccagttacc ttcggaaaaa gagttggtag ctcttgatcc ggcaaacaaa    2100
ccaccgctgg tagcggtggt ttttttgttt gcaagcagca gattacgcgc agaaaaaaag    2160
gatctcaaga agatcctttg atcttttcta cggggtctga cgctcagtgg aacgaaaact    2220
cacgttaagg gattttggtc atgagattat caaaaaggat cttcacctag atcctttaa     2280 attaaaaatg aagttttaaa tcaatctaaa gtatatatga gtaaacttgg tctgacagtt    2340
accaatgctt aatcagtgag gcacctatct cagcgatctg tctatttcgt tcatccatag    2400
ttgcctgact ccccgtcgtg tagataacta cgatacggga gggcttacca tctggcccca    2460
gtgctgcaat gataccgcga gacccacgct caccggctcc agatttatca gcaataaacc    2520
agccagccgg aagggccgag cgcagaagtg gtcctgcaac tttatccgcc tccatccagt    2580
ctattaattg ttgccgggaa gctagagtaa gtagttcgcc agttaatagt ttgcgcaacg    2640
ttgttgccat tgctacaggc atcgtggtgt cacgctcgtc gtttggtatg gcttcattca    2700
gctccggttc ccaacgatca aggcgagtta catgatcccc catgttgtgc aaaaaagcgg    2760
ttagctcctt cggtcctccg atcgttgtca gaagtaagtt ggccgcagtg ttatcactca    2820
tggttatggc agcactgcat aattctctta ctgtcatgcc atccgtaaga tgcttttctg    2880
tgactggtga gtactcaacc aagtcattct gagaatagtg tatgcggcga ccgagttgct    2940
cttgcccggc gtcaatacgg gataataccg cgccacatag cagaacttta aaagtgctca    3000
tcattggaaa acgttcttcg gggcgaaaac tctcaaggat cttaccgctg ttgagatcca    3060
gttcgatgta acccactcgt gcacccaact gatcttcagc atcttttact ttcaccagcg    3120
tttctgggtg agcaaaaaca ggaaggcaaa atgccgcaaa aaagggaata agggcgacac    3180
ggaaatgttg aatactcata ctcttccttt ttcaatatta ttgaagcatt tatcagggtt    3240
attgtctcat gagcggatac atatttgaat gtatttagaa aaataaacaa ataggggttc    3300
cgcgcacatt tccccgaaaa gtgccacctg atgcggtgtg aaataccgca cagatgcgta    3360
aggagaaaat accgcatcag gaaattgtaa gcgttaatat tttgttaaaa ttcgcgttaa    3420
atttttgtta aatcagctca ttttttaacc aataggccga atcggcaaaa tcccttata     3480 aatcaaaaga atagaccgag atagggttga gtgttgttcc agtttggaac aagagtccac    3540
tattaaagaa cgtggactcc aacgtcaaag ggcgaaaaac cgtctatcag ggcgatggcc    3600
cactacgtga accatcaccc taatcaagtt ttttggggtc gaggtgccgt aaagcactaa    3660
atcggaaccc taaagggagc ccccgattta gagcttgacg gggaaagccg gcgaacgtgg    3720
cgagaaagga agggaagaaa gcgaaaggag cgggcgctag ggcgctggca agtgtagcgg    3780
tcacgctgcg cgtaaccacc acacccgccg cgcttaatgc gccgctacag ggcgcgtcca    3840
ttcgccattc aggctgcgca actgttggga agggcgatcg gtgcgggcct cttcgctatt    3900
acgccagctg gcgaaagggg gatgtgctgc aaggcgatta agttgggtaa cgccagggtt    3960
ttcccagtca cgacgttgta aaacgacggc cagtgaattg taatacgact cactataggg    4020
cgaattgggc ccgacgtcgc atgcttggaa gggctaattc actcccaaag aagacaagat    4080
atccttgatc tgtggatcta ccacacacaa ggctacttcc ctgattagca gaactacaca    4140
ccagggccag gggtcagata tccactgacc tttggatggt gctacaagct agtaccagtt    4200
gagccagata aggtagaaga ggccaataaa ggagagaaca ccagcttgtt acaccctgtg    4260
agcctgcatg gaatggatga cccggagaga gaagtgttag agtggaggtt tgacagccgc    4320
ctagcatttc atcacgtggc ccgagagctg catccggagt acttcaagaa ctgctgatat    4380
```

```
cgagcttgct acaagggact ttccgctggg gactttccag ggaggcgtgg cctgggcggg    4440
actggggagt ggcgagccct cagatcctgc atataagcag ctgctttttg cctgtactgg    4500
gtctctctgg ttagaccaga tctgagcctg ggagctctct ggctaactag ggaacccact    4560
gcttaagcct caataaagct tgccttgagt gcttcaagta gtgtgtgccc gtctgttgtg    4620
tgactctggt aactagagat ccctcagacc cttttagtca gtgtggaaaa tctctagcag    4680
tggcgcccga cagggacttt gaaagcgaaa gggaaaccag aggagctctc tcgacgcagg    4740
actcggcttg ctgaagcgcg cacggcaaga ggcgaggggc ggcgactggt gagtacgcca    4800
aaaattttga ctagcggagg ctagaaggag agagatgggt gcgagagcgt cagtattaag    4860
cgggggagaa ttagatcgcg atgggaaaaa attcggttaa ggccagggg a aagaaaaaa    4920
tataaattaa acatatagt atgggcaagc agggagctag aacgattcgc agttaatcct    4980
ggcctgttag aaacatcaga aggctgtaga caaatactgg gacagctaca accatccctt    5040
cagacaggat cagaagaact tagatcatta tataatacag tagcaaccct ctattgtgtg    5100
catcaaagga tagagataaa agacaccaag gaagctttag acaagataga ggaagagcaa    5160
aacaaaagta agaccaccgc acagcaagcg ccgctgatc ttcagacctg gaggaggaga    5220
tatgagggac aattggagaa gtgaattata taaatataaa gtagtaaaaa ttgaaccatt    5280
aggagtagca cccaccaagg caaagagaag agtggtgcag agagaaaaaa gagcagtggg    5340
aataggagct ttgttccttg ggttctgggg agcagcagga agcactatgg gcgcagcgtc    5400
aatgacgctg acggtacagg ccagacaatt attgtctggt atagtgcagc agcagaacaa    5460
tttgctgagg gctattgagg cgcaacagca tctgttgcaa ctcacagtct ggggcatcaa    5520
gcagctccag gcaagaatcc tggctgtgga agatacccta aaggatcaac agctcctggg    5580
gatttggggt tgctctggaa aactcatttg caccactgct gtgccttgga atgctagttg    5640
gagtaataaa tctctggaac agatttggaa tcacacgacc tggatggagt gggacagaga    5700
aattaacaat tacacaagct taatacactc cttaattgaa gaatcgcaaa accagcaaga    5760
aaagaatgaa caagaattat tggaattaga taaatgggca agtttgtgga attggtttaa    5820
cataacaaat tggctgtggt atataaaatt attcataatg atagtaggag gcttggtagg    5880
tttaagaata gttttgctg tactttctat agtgaataga gttaggcagg gatattcacc    5940
attatcgttt cagacccacc tcccaacccc gaggggaccc gacaggcccg aaggaataga    6000
agaagaaggt ggagagagag acagagacag atccattcga ttagtgaacg gatctcgacg    6060
ggatcgattt taaagaaaa gggggg att g gg g gtacag tgcaggggaa agaatagtag    6120
acataatagc aacagacata caaactaaag aattacaaaa acaaattaca aaaattcaaa    6180
attttatcga taagctttgc aaagatggat aaagttttaa acagagagga atctttgcag    6240
ctaatggacc ttctaggtct gaccccgtac gcctcgagag atctgatcat aatcagccat    6300
accacatttg tagaggtttt acttgcttta aaaaacctcc cacacctccc cctgaacctg    6360
aaacataaaa tgaatgcaat tgttgttgtt aacttgttta ttgcagctta taatggttac    6420
aaataaggca atagcatcac aaatttcaca ataaggcat t ttttttcact gcattctagt    6480
tttggtttgt ccaaactcat caatgtatct tatcatgtct ggatctcaaa tcccctcggaa    6540
gctgcgcctg tcttaggttg gagtgataca ttttt atcac ttttacccgt ctttggatta    6600
ggcagtagct ctgacggccc tcctgtctta ggttagtgaa aaatgtcact ctcttacccg    6660
tcattggctg tccagcttag ctcgcagggg aggtggtctg cctgcaggtt agaacagtct    6720
cttttcgtat gagtgcagtg agtggacgcc gccttcgacc tgggctgaag aagttctttt    6780
```

```
ctcgaacttc agttcgccgg aatacatcat tgcccgcacc tgtgtcaggc tcttagcgcc    6840
gatatcctgg catgaatgct gaattccggc gatcaggtaa ggcacgaatt tgtgaatact    6900
gcccttatcc tggacagctc cagacacgcc ctgtgcgact ttgatcttgt ctgcctcgga    6960
aaaatacctg ttctgagagg acagatgctt atccatggcg tccagtgacc ccatgcccct    7020
atatttcttc agtctgaacc catcactaaa gaagtactcg ccgggggctt ctgtggttgc    7080
agccagcagg ctgcccatca tcactgtgct gcccccagaa gccagggctt ttgcgatgtg    7140
gcccacattc tgaattcccc cgtcagcgat cactgggact ccgaatctcc gggcatactc    7200
gtacaccttg tagacagcag ttgcctgagg tcgtccacag gccagcactt cctgaatgat    7260
gcagattgat ccactcccca ttccgaccct cagagcatcc actcctgcgt caatcaggtt    7320
tttggcctgg gctgcggtca cgacattgcc tccgatgacc tgcagatttg gtacttgtc     7380
cttaatgtac ttgatcatat taatctggaa gatgctgttt ccctggcttg aatccagcac    7440
gaccacgtcc acccctgcct gagccagcag atccaggcga tatttatcgt cctcgtgtgt    7500
gccaatagcg gctccacaca gcagctgttt ctttgcgtcc ttactagcca gagggtaatc    7560
tcgattttc ttcaggtcgg tgcgggcaat gattgccacc agctcatcgt cttcattcac     7620
gataggcagt tttcctttct tagaccgctg cagaatctcg ttggcttcct tcagtgtgat    7680
gccggcaggt gcgaccacca gatcttcgcg tttggtcata atctcttcca gaaacagtc     7740
atgctcttcc tccttcagga aatcgatgtc tcgactagaa atgattccca ccagtcggct    7800
gcccattcgt ccagtatctg taatggggat gccgcaaaat ccgtgcctag ctttggcctc    7860
gaacacatcg cggaccctgt ccttggggct caggaccact gggtcggtga taagccctg     7920
ttcgtatttc ttcacctttc tgacctcatt ggcctgaaat tctggagtgc agttatggtg    7980
aatgaacccg atcccgcctg tcagtgccat agcaatggcc atgccagcct cggtgacagt    8040
gtccataggg gagctcacca ggggtgtctt caggatgatt ttcttggtca gggcagaagt    8100
cagatccacc tggtctgcgg taaaatcaat atagccgggc aggatcagga agtcgttgta    8160
agtcagcccg tctccacaat taaacagctg ctgggcggtc agtccatcat cagggacata    8220
ggaagtgcct ccagaaatca ggtagtcggc catggtggcg ctagccctgg ggagagaggt    8280
cggtgattcg gtcaacgagg gagccgactg ccgacgtgcg ctccggaggc ttgcagaatg    8340
cggaacaccg cgcgggcagg aacagggccc acactaccgc cccacacccc gcctcccgca    8400
ccgcccttc ccggccgctg ctctcggcgc gccccgctga gcagccgcta ttggccacag    8460
cccatcgcgg tcgcgcgct gccattgctc cctggcgctg tccgtctgcg agggtactag     8520
tgagacgtgc ggcttccgtt tgtcacgtcc ggcacgccgc gaaccgcaag gaaccttccc    8580
gacttagggg cggagcagga agcgtcgccg ggggcccac aagggtagcg gcgaagatcc     8640
gggtgacgct gcgaacggac gtgaagaatg tgcgagaccc agggtcggcg ccgctgcgtt    8700
tcccggaacc acgcccagag cagccgcgtc cctgcgcaaa cccagggctg ccaaggaaaa    8760
ggcgcaaccc caaccccgtg gttaattaag gtgaaaggag tgggaattgg ctccggtgcc    8820
cgtcagtggg cagagcgcac atcgcccaca gtccccgaga gttgggggg aggggtcggc     8880
aattgaaccg gtgcctagag aaggtggcgc ggggtaaact gggaaagtga tgtcgtgtac    8940
tggctccgcc tttttcccga gggtgggga gaaccgtata aagtgcagt agtcgccgtg      9000
aacgttcttt ttcgcaacgg gtttgccgcc agaacacagg taagtgccgt gtgtggttcc    9060
cgcgggcctg gcctctttac gggttatggc ccttgcgtgc cttgaattac ttccacctgg    9120
ctgcagtacg tgattcttga tcccgagctt cgggttggaa gtgggtggga gagttcgagg    9180
```

```
ccttgcgctt aaggagcccc ttcgcctcgt gcttgagttg aggcctggcc tgggcgctgg    9240
ggccgccgcg tgcgaatctg gtggcacctt cgcgcctgtc tcgctgcttt cgataagtct    9300
ctagccattt aaaattttg atgacctgct gcgacgcttt ttttctggca agatagtctt     9360
gtaaatgcgg gccaagatct gcacactggt atttcggttt ttggggccgc gggcggcgac    9420
ggggcccgtg cgtcccagcg cacatgttcg gcgaggcggg gcctgcgagc gcggccaccg    9480
agaatcggac gggggtagtc tcaagctggc cggcctgctc tggtgcctgg cctcgcgccg    9540
ccgtgtatcg ccccgccctg gcggcaagg ctggcccggt cggcaccagt tgcgtgagcg     9600
gaaagatggc cgcttcccgg ccctgctgca gggagctcaa aatggaggac gcggcgctcg    9660
ggagagcggg cgggtgagtc acccacacaa aggaaaaggg cctttccgtc tcagccgtc    9720
gcttcatgtg actccacgga gtaccgggcg ccgtccaggc acctcgatta gttctcgagc    9780
ttttggagta cgtcgtcttt aggttggggg gaggggtttt atgcgatgga gtttccccac    9840
actgagtggg tggagactga agttaggcca gcttggcact tgatgtaatt ctccttggaa    9900
tttgcccttt ttgagtttgg atcttggttc attctcaagc ctcagacagt ggttcaaagt    9960
tttttcttc catttcaggt gtcgtgagga attcgtcgac gccgccacca tgcaaataga    10020
gctctccacc tgcttctttc tgtgcctttt gcgattctgc tttagtgcca ccagaagata    10080
ctacctgggt gcagtggaac tgtcatggga ctatatgcaa agtgatctcg gtgagctgcc    10140
tgtggacgca agatttcctc ctagagtgcc aaaatctttt ccattcaaca cctcagtcgt    10200
gtacaaaaag actctgtttg tagaatttac ggatcacctt ttcaacatcg ctaagccaag    10260
gccaccctgg atgggtctgc taggtcctac catccaggct gaggtttatg atacagtggt    10320
cattacactt aagaacatgg cttcccatcc tgtcagtctt catgctgttg gtgtatccta    10380
ctggaaagct tctgagggag ctgaatatga tgatcagacc agtcaaaggg agaaagaaga    10440
tgataaagtc ttccctggtg gaagccatac atatgtctgg caggtcctga agagaatgg    10500
tccaatggcc tctgacccac tgtgccttac ctactcatat ctttctcatg tggacctggt    10560
aaaagacttg aactcaggcc tcattggagc cctactagta tgtagagaag ggagtctggc    10620
caaggaaaag acacagacct tgcacaaatt tatactactt tttgctgtat ttgatgaagg    10680
gaaaagttgg cactcagaaa caaagaactc cttgatgcag gatagggatg ctgcatctgc    10740
tcggggcctgg cctaaaatgc acacagtcaa tggttatgta aacaggtctc tgccaggtct    10800
gattggatgc cacaggaaat cagtctattg gcatgtgatt ggaatgggca ccactcctga    10860
agtgcactca atattcctcg aaggtcacac atttcttgtg aggaaccatc gccaggcgtc    10920
cttggaaatc tcgccaataa ctttccttac tgctcaaaca ctcttgatgg accttggaca    10980
gtttctactg ttttgtcata tctcttccca ccaacatgat ggcatggaag cttatgtcaa    11040
agtagacagc tgtccagagg aaccccaact acgaatgaaa aataatgaag aagcggaaga    11100
ctatgatgat gatcttactg attctgaaat ggatgtggtc aggtttgatg atgacaactc    11160
tccttccttt atccaaattc gctcagttgc caagaagcat cctaaaactt gggtacatta    11220
cattgctgct gaagaggagg actgggacta tgctccctta gtcctcgccc ccgatgacag    11280
aagttataaa agtcaatatt tgaacaatgg ccctcagcgg attggtagga agtacaaaaa    11340
agtccgattt atggcataca cagatgaaac ctttaagact cgtgaagcta ttcagcatga    11400
atcaggaatc ttgggacctt tactttatgg ggaagttgga gacacactgt tgattatatt    11460
taagaatcaa gcaagcagac catataacat ctaccctcac ggaatcactg atgtccgtcc    11520
tttgtattca aggagattac caaaaggtgt aaaacatttg aaggattttc caattctgcc    11580
```

```
aggagaaata ttcaaatata aatggacagt gactgtagaa gatgggccaa ctaaatcaga    11640
tcctcggtgc ctgacccgct attactctag tttcgttaat atggagagag atctagcttc    11700
aggactcatt ggccctctcc tcatctgcta caaagaatct gtagatcaaa gaggaaacca    11760
gataatgtca gacaagagga atgtcatcct gttttctgta tttgatgaga accgaagctg    11820
gtacctcaca gagaatatac aacgctttct ccccaatcca gctggagtgc agcttgagga    11880
cccagagttc caagcctcca acatcatgca cagcatcaat ggctatgttt ttgatagttt    11940
gcagttgtca gtttgtttgc atgaggtggc atactggtac attctaagca ttggagcaca    12000
gactgacttc ctttctgtct tcttctctgg atataccttc aaacacaaaa tggtctatga    12060
agacacactc accctattcc cattctcagg agaaactgtc ttcatgtcga tggaaaaccc    12120
aggtctatgg attctggggt gccacaactc agactttcgg aacagaggca tgaccgcctt    12180
actgaaggtt tctagttgtg acaagaacac tggtgattat tacgaggaca gttatgaaga    12240
tatttcagca tacttgctga gtaaaaacaa tgccattgaa ccaagaagct tctctcaaaa    12300
cccaccagtc ttgaaacgcc atcaacggga ataactcgt  actactcttc agtcagatca    12360
agaggaaatt gactatgatg ataccatatc agttgaaatg aagaaggaag attttgacat    12420
ttatgatgag gatgaaaatc agagcccccg cagctttcaa aagaaaacac gacactattt    12480
tattgctgca gtggagaggc tctgggatta tgggatgagt agctccccac atgttctaag    12540
aaacagggct cagagtggca gtgtccctca gttcaagaaa gttgttttcc aggaatttac    12600
tgatggctcc tttactcagc ccttataccg tggagaacta atgaacatt  tgggactcct    12660 ggggccatat ataagagcag aagttgaaga taatatcatg gtaactttca gaaatcaggc    12720
ctctcgtccc tattccttct attctagcct tatttcttat gaggaagatc agaggcaagg    12780
agcagaacct agaaaaaact ttgtcaagcc taatgaaacc aaaacttact tttggaaagt    12840
gcaacatcat atggcaccca ctaaagatga gtttgactgc aaagcctggg cttatttctc    12900
tgatgttgac ctggaaaaag atgtgcactc aggcctgatt ggacccctc  tggtctgcca    12960 cactaacaca ctgaaccctg ctcatgggag acaagtgaca gtacaggaat tgctctgtt   13020 tttcaccatc tttgatgaga ccaaaagctg gtacttcact gaaaatatgg aaagaaactg    13080
cagggctccc tgcaatatcc agatggaaga tcccactttt aaagagaatt atcgcttcca    13140
tgcaatcaat ggctacataa tggatacact acctggctta gtaatggctc aggatcaaag    13200
gattcgatgg tatctgctca gcatgggcag caatgaaaac atccattcta ttcatttcag    13260
tggacatgtg ttcactgtac gaaaaaaaga ggagtataaa atggcactgt acaatctcta    13320
tccaggtgtt tttgagacag tggaaatgtt accatccaaa gctggaattt ggcgggtgga    13380
atgccttatt ggcgagcatc tacatgctgg gatgagcaca cttttctctgg tgtacagcaa    13440 taagtgtcag actccctgg gaatggcttc tggacacatt agagattttc agattacagc    13500
ttcaggacaa tatggacagt gggccccaaa gctggccaga cttcattatt ccggatcaat    13560
caatgcctgg agcaccaagg agccctttc  ttggatcaag gtggatctgt ggcaccaat    13620 gattattcac ggcatcaaga cccagggtgc ccgtcagaag ttctccagcc tctacatctc    13680
tcagtttatc atcatgtata gtcttgatgg gaagaagtgg cagacttatc gaggaaattc    13740
cactggaacc ttaatggtct ctttggcaa  tgtggattca tctgggataa aacacaatat    13800 ttttaacccct ccaattattg ctcgatacat ccgtttgcac ccaactcatt atagcattcg    13860
cagcactctt cgcatggagt tgatgggctg tgatttaaat agttgcagca tgccattggg    13920
aatggagagt aaagcaatat cagatgcaca gattactgct tcatcctact ttaccaatat    13980
```

-continued

```
gtttgccacc tggtctcctt caaaagctcg acttcacctc caagggagga gtaatgcctg    14040
gagacctcag gtgaataatc caaaagagtg gctgcaagtg gacttccaga agacaatgaa    14100
agtcacagga gtaactactc agggagtaaa atctctgctt accagcatgt atgtgaagga    14160
gttcctcatc tccagcagtc aagatggcca tcagtggact ctcttttttc agaatggcaa    14220
agtaaaggtt tttcagggaa atcaagactc cttcacacct gtggtgaact ctctagaccc    14280
accgttactg actcgctacc ttcgaatcca cccccagagt tgggtgcacc agattgccct    14340
gaggatggag gttctgggct gcgaggcaca ggacctctac tgacccgg                 14388
```

IN VITRO AND IN VIVO ENRICHMENT STRATEGY TARGETING LYMPHOCYTES DERIVED FROM VECTOR TRANSDUCED HSCS FOR THERAPY OF DISORDERS

CROSS-REFERENCE TO RELATED APPLICATIONS

This Application represents the national stage entry of PCT International Application No. PCT/US2018/036292 filed on Jun. 6, 2018 and claims priority to U.S. Provisional Application No. 62/515,022 filed on Jun. 6, 2017 and U.S. Provisional Application No. 62/664,671 filed on Apr. 30, 2018, the contents of which are incorporated by reference in their entireties.

STATEMENT REGARDING FEDERALLY SPONSORED RESEARCH

N/A.

BACKGROUND OF THE INVENTION

The field of the invention is related to treatment of diseases and disorders associated with a single altered protein or enzyme, in particular diseases that can be treated with engrafted hematopoietic cells, for example, lysosomal storage disorders such as Fabry disease and Gaucher disease which are associated with dysregulation or deficiency of a single protein or in some instances a single protein combined with a co-activator protein.
Lysosomal Storage Disorders Lysosomes are membrane-bound organelles in animal cells that contain more than 60 different enzymes capable of digesting nearly any biomolecule. They carry many critical biological functions, including acting as the cell's waste disposal system by digesting unwanted materials in the cytoplasm, both from outside of the cell and obsolete components inside the cell. Lysosomal Storage Disorders (LSDs, lysosomal storage diseases) are a group of more than 60 rare inherited metabolic disorders that result from lysosome dysfunction, usually as a consequence of a deficiency in a single enzyme required for the intracellular digestion of lipids, glycoproteins, or mucopolysaccharides. As a result of such deficiencies, the molecules that would normally be degraded accumulate inside the cell, leading to dysfunction or death of the cell.
Fabry Disease Fabry disease is a LSD resulting from a deficiency in the enzyme α-galactosidase A (α-gal A encoded by the AGA transgene), an enzyme that hydrolyses α-galactose from glycosphingolipids, in particular globotriaosylceramide ($Gb_3$). Sphingolipids play an important role in signal transmission and cell recognition, and sphingolipidoses can impact all tissues. Currently, enzyme replacement therapy (ERT) is used to treat Fabry disease, and with ERT, patients with Fabry disease may live well into adulthood. However, ERT requires lengthy intravenous infusions of α-gal A administered every few weeks, usually at an outpatient center. In addition, Fabry patients often require treatments for pain, gastrointestinal dysfunction, arrhythmias and other heart problems, as well as blood thinners and blood pressure medications to protect kidney function. Although Fabry disease is relatively rare—there are about 4000 patients in the US—treatment costs are on the order of $300,000/year/patient, or $1.2B/y for all US patients.

Genetic Modification of Hematopoietic Stem Cells from Fabry Patients

Prior work by the inventor related to the use of a cellular therapy for Fabry disease. The method is based on the use of hematopoietic stem cells (HSCs), which are "multipotent" cells present in bone marrow that can differentiate into all blood cell types. A method of genetically modifying HSCs taken from Fabry patients was developed by "transducing" the cells with a recombinant lentivirus vector carrying the transgene for the α-gal A enzyme. Upon re-introduction of the patient's modified cells back into the patient (an "autologous" graft), the genetically modified stem cells will populate all downstream lineages of the hematopoietic system and then circulate throughout the body. The modified cells secrete a form of α-gal A with a molecular "tag" (mannose 6-phosphate) which allows uncorrected "bystander" cells in the patient to take up and transport α-gal A intracellularly into their lysosomes, where it can compensate for the patient's α-gal A deficiency, and effectively degrade the accumulated sphingolipids. This method is undergoing clinical trials in Canada (ClinicalTrials.gov #NCT02800070).

However, systemic expression of α-gal A using this method is relatively low, in part because of a key step in the process. It is only possible to obtain a relatively small number of HSCs from patients as HSCs are relatively rare cells, and it is also difficult to get a high level of transduction in HSCs. These limitations may constrain ability of these cells to adequately increase the systemic levels of α-gal A within a subject. Increasing the number of cells producing α-gal A will in turn increase the systemic α-gal A levels. Thus, there is a need to develop methods of increasing the number of α-gal A-expressing cells after HSC engraftment to subsequently increase systemic levels of α-gal A for treatment of Fabry disease.
Gaucher Disease Gaucher disease is an autosomal recessive inherited disorder caused by mutations in the GBA transgene that leads to a reduction or elimination of activity of beta-glucocerebrosidase (GBA protein). This enzyme breaks down glucocerebroside into a sugar (glucose) and a simpler fat-like molecule (ceramide). Without enough of this enzyme, glucocerebroside and related substances can build up to toxic levels within cells, including the spleen, liver and bone tissue. Tissues and organs are damaged by the abnormal accumulation and storage of these substances, causing the characteristic features of Gaucher disease.

Traditional treatment for Gaucher disease is enzyme replacement therapy. However, better methods of treating such a disease are needed.

SUMMARY OF THE INVENTION

The present invention overcomes the aforementioned drawbacks by providing a method of enriching for hematopoietic cells in vitro, ex vivo and in vivo that express the desired transgene, for example, but not limited to, AGA transgene for Fabry Disease or GBA transgene for Gaucher disease.

The inventors in the present invention have engineered a "dual promoter" lentivirus vector for expression of a protein from a transgene of interest, for example, but not limited to, α-gal A or GBA protein, and an enzyme, IMPDH2(IY), that confers mycophenolic acid (MPA) resistance to transduced B- and T-cells in the white cell population. MPA, which is delivered in vivo as the FDA approved drug mycophenolate mofetil (MMF), inhibits an enzyme needed for the growth of T cells and B cells. MMF is used routinely in the clinic as an immunosuppressive agent for a variety of indications (e.g., to prevent organ transplant rejection) with a low incidence of adverse side-effects. The primary consequence of in vivo administration of MPA/MMF is on T and B cell depletion, but T and B cells that arise from the engrafted hematopoietic stem cells (HSCs) that are transduced with the dual promoter lentiviral vector are resistant to MPA and have a selective growth advantage. Treatment with low doses of MMF increases the number of therapeutic lymphocytes in vivo, without affecting the original engraftment, with minimal toxicity. This, in turn, increases the total number of circulating cells that are expressing the transgene of interest, and thus the cells are able to express and/or secrete the protein encoded by the transgene, for example, secreting α-gal A, GBA protein, or other protein expressed by other transgenes of interest, which can lead to treatment or correction of the disease associated with the transgene, e.g., the lysosomal storage disorder.

This platform technology is broadly applicable to hematopoietic cell-based treatment of many inherited disorders, including other lysosomal storage disorders or hematopoietic system diseases in which a selective growth advantage of altered hematopoietic cells allows for treatment of the disease.

In one aspect, a dual promoter lentivirus vector that expresses α-galactosidase A and IMPDH2(IY) when transduced into a host cell and confers resistance to mycophenolic acid (MPA) and/or mycophenolate mofetil (MMF) in vitro and/or in vivo is provided herein.

In another aspect, the invention provides a dual promoter lentivirus vector that expresses a protein of interest encoded by a transgene along with IMPDH2(IY) when transduced into a host cell and confers resistance to mycophenolic acid (MPA) and/or mycophenolate mofetil (MMF) in vitro and/or in vivo. Suitable, the transgene can encode for a protein or enzyme deficient or dysregulated in a disease or disorder.

In another aspect, the invention provides a method of treating a subject in need of treatment for Fabry disease. The method comprises the steps of i) obtaining hematopoietic stem cells (HSCs) from the patient and/or HSCs from a suitable donor, ii) transducing the HSCs ex vivo or in vitro with a dual promoter lentivirus vector that expresses α-gal A and IMPDH2(IY) in the transduced cells, iii) introducing the transduced HSCs into the subject, and iv) administering to the subject an amount of mycophenolate mofetil (MMF) sufficient to enrich the population of lentivirus vector transduced hematopoietic cells, e.g. T and B cells in the subject.

In another aspect, a method of treating a subject having a disease associated with a defect in a single protein are provided. The method comprising the steps of i) obtaining hematopoietic stem cells (HSCs) from the patient and/or HSCs from a suitable donor, ii) transducing the HSCs ex vivo or in vitro with a dual promoter lentivirus vector that expresses a functional form of the protein of interest encoded by a transgene, and IMPDH2(IY) in the transduced cells, iii) introducing the transduced HSCs into the subject, and iv) administering to the subject an amount of mycophenolate mofetil (MMF) sufficient to enrich for the population of hematopoietic cells (e.g. T cells and B cells) that are formed from the lentivirus vector transduced HSCs engrafted in the subject.

In a particular aspect, the disease is Gaucher disease and the single protein is beta-glucocerebrosidase (GBA protein) encoded by the GBA transgene.

In another particular aspect, the disease is Fabry disease and the single protein is alpha galactosidase. In one aspect, the dual promoter is SEQ ID NO:3 or a sequence that has at least 80% identity to SEQ ID NO:3.

In another aspect, the dual promoter lentivirus vector expresses GBA protein and IMPDH2(IY). A suitable vector is found in SEQ ID NO:4 or a sequence that has at least 80% identity to SEQ ID NO:4, alternatively a sequence that has at least 90% identity, alternatively a sequence that has about 95% identity, alternatively a sequence that has at least 98% identity, alternatively a sequence that has about 99% sequence identity.

In another aspect, the invention provides a method of treating a subject in need of treatment for Gaucher disease. The method comprises the steps of i) obtaining hematopoietic stem cells (HSCs) from the patient and/or HSCs from a suitable donor, ii) transducing the HSCs ex vivo or in vitro with a dual promoter lentivirus vector that expresses GBA protein and IMPDH2(IY) in the transduced cells, iii) introducing the transduced HSCs into the subject, and iv) administering to the subject an amount of mycophenolate mofetil (MMF) sufficient to enrich the population of lentivirus vector transduced hematopoietic cells, e.g. T and B cells in the subject. The method is able to treat or reduce one or more symptoms of Gaucher disease.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 4C depicts the results for vector copy number per genome for the different Jurkat cell populations.

FIG. 4D depicts the live vector copies calculated for cells on day 16.

FIG. 4E depicts α-galactosidase A (α-gal A) activity in the cell lysates.

FIG. 4F depicts α-gal A activity in the supernatants.

DETAILED DESCRIPTION OF THE INVENTION

Figure 1:
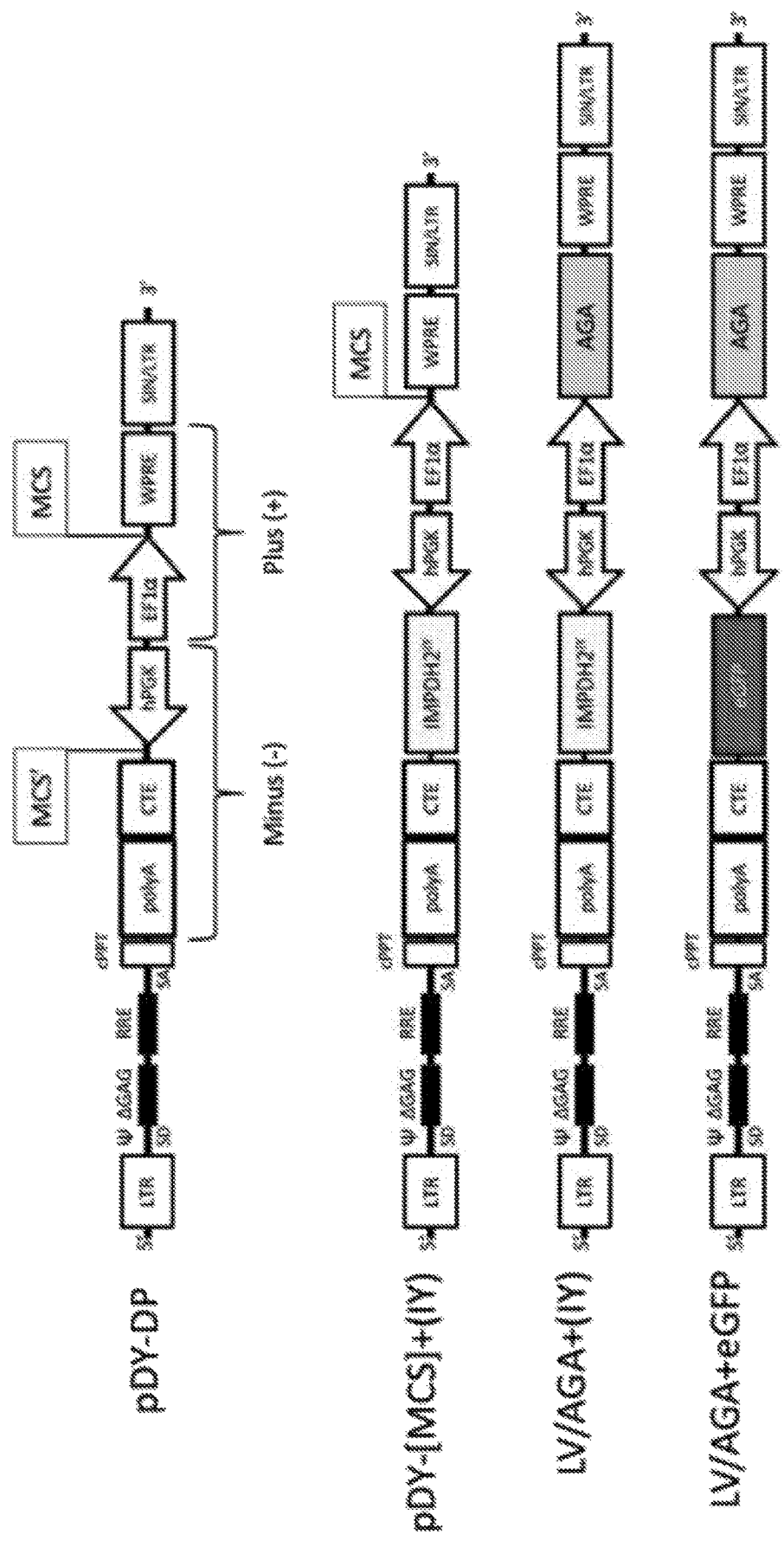
FIG. 1 is a schematic drawing depicting exemplary lentiviral vectors of the present invention.

The present invention has been described in terms of one or more preferred embodiments, and it should be appreciated that many equivalents, alternatives, variations, and modifications, aside from those expressly stated, are possible and within the scope of the invention.

The present invention provides dual promoter lentiviral vectors that can be used for the treatment of diseases and disorders that are the result of the dysregulation or dysfunction of a single protein or enzyme. Specifically, the present invention provides a dual promoter lentiviral vector that expresses a transgene of interest and a mutant form of inosine-5'-monophosphate dehydrogenase 2 (IMPDH2) that contains T333I and S351Y (IY) mutations within the gene (IMPDH2(IY)) which confers resistance to MPA in a transdominant manner. The vector confers resistance to mycophenolic acid (MPA) and/or mycophenolate mofetil (MMF) in vitro and in vivo when expressed within the host cell. As such the dual promoter lentiviral vectors may be used to transform hematopoietic stem cells that confers mycophenolic acid (MPA) resistance to transduced hematopoietic cells, including the derived B- and T-cells in the white cell population. MPA, which is delivered in vivo as the FDA approved drug mycophenolate mofetil (MMF), inhibits an enzyme needed for the growth of T cells and B cells. As discussed above, the primary consequence of in vivo administration of MPA/MMF is on T and B cell depletion, but in addition, the present invention shows that T and B cells that arise from the engrafted hematopoietic stem cells (HSCs) that are transduced with the dual promoter lentiviral vector are resistant to MPA and have a selective growth advantage. Treatment with low doses of MMF increases the number of therapeutic transduced lymphocytes in vivo with minimal toxicity. This, in turn, increases the total number of circulating cells that are expressing the transgene of interest, and thus the cells are able to express and/or secrete the protein encoded by the transgene of interest, which can lead to treatment or correction of the disease associated with the transgene, e.g., the lysosomal storage disorder.

This platform technology is broadly applicable to hematopoietic cell-based treatment of many inherited disorders, including other lysosomal storage disorders or hematopoietic system diseases in which a selective growth advantage of altered T cells or B cells allows for treatment of the disease. In some embodiments, this technology is applicable to hematopoeiteic cell-based treatment of inherited disorders, for example, clotting disorders, in which a The transgene may be any protein or enzyme that is associated with a disease or disorder. In some instances, the transgene is an enzyme or protein associated with a lysosomal storage disorder. In one embodiment, the lysosomal storage disorder is Fabry disease and the transgene is AGA which encodes the enzyme α-galactosidase A (α-gal A). As used herein, the term α-galactosidase A and α-gal A are used interchangeably to refer to α-galactosidase enzyme (protein). In suitable embodiments, the transgene is a human protein, for example, α-galactosidase A, for treatment of Fabry disease. Suitable transgenes include transgenes that are not immunogenic (e.g. are preferably from human), and/or (b) have no gross effect on the hematopoietic system. Another suitable embodiment, the transgene encodes for a human protein for beta-glucocerebrosidase or glucosylceramidase (GBA protein or GCase). In suitable embodiments, the vector encodes for and expresses a transgene lacking in the disease, particularly lysosomal storage diseases, for example, but not limited to, α-gal A for Fabry disease, beta-glucocerebrosidase (GBA) for Gaucher disease, acid ceramidase (ASAH1) for Farber disease, acid α-glucosidase (GAA, also known as acid maltase) for Pompe disease.

Suitable diseases and transgenes may relate to lysosomal storage disorders, including inherited metabolic disorders that result from defects in lysosomal function. Lysosomal storage disorders are caused by lysosomal dysfunction usually as a consequence of deficiency of a single enzyme required for the metabolism of lipids, glycoproteins (sugar containing proteins) or so-called mucopolysaccharides. Suitable lysosomal storage disorders and transgenes that are contemplated to be treated by this method include, but are not limited to, for example, mucolipidosis type II and IIIa (N-acetylglucosamine-1-phosphate transferase), galactosialidosis (cathepsinA), GM2-AP deficiency (GM2-AP), Niemann-Pick disease type C2 (NPC2), Niemann-Pick disease type C1 (NPC1), Salla disease (sialin), Krabbe disease (galactosylceramidase), GM1 gangliosidosis (beta-galactosidase), GM gangliosidoses (beta-hexosaminidases), Fabry disease (α-galactosidase A), Schindler disease (α-galactosidase B), Sandhoff disease (beta-hexosaminidase B), Tay-Sachs disease (beta-hexosaminidase A), Gaucher's disease (glucocerebrosidase), lysosomal acid lipase deficiency (lysosomal acid lipase (LAL) enzyme), sulfatidosis (sulfatase enzymes), Metachromatic leukodystrophy (MLD, also called arylsulfatase A deficiency, enzyme arylsulfatase A (ARSA)), multiple sulfatase deficiency or Austin disease (formylglycine-generating enzyme), mucopolysaccharidoses, Hurler syndrome (α-L iduronidase), Scheie and Hurler-Scheie syndrome (α-L iduronidase), Hunter syndrome (iduronate-2-sulfatase (I2S)), Sanfilippo syndrome (heparan N-sulfatase (MPS-IIIA)), N-acetyl-α-D-glucosaminidase (MPS-IIIB), acetyl-CoA:α-glucosaminidine acetyltransferase (MPS-III C), N-acetylglucosamine-G-sulfate sulfatase (MPS-IIID), Maroteaux-Lamy syndrome (arylsulfatase B), Sly syndrome (beta-glucuronidase), hyaluronidase deficiency (hyaluronidase), Sialidosis (α-N-acetyl neuraminidase (sialidase)), Inclusion-cell (I-cell) disease (phosphotransferase), Mucolipidin 1 deficiency (mucolipidin 1), neuronal ceroid lipofuscinosis (CLN) family (palmitoyl-protein thioesterase 1 (PPT-1), tripeptidyl peptidase I (TPP1), battenin (CLN3), Ceroid-lipofuscinosis neuronal protein 6 (CLN6 gene), Ceroid-lipofuscinosis neuronal protein 5, Ceroid-lipofuscinosis neuronal protein 8, Major facilitator superfamily domain containing 8, cathepsin D, among others), α-mannosidosis (α-mannosidase enzyme), beta-mannosidosis (beta-mannosidase), Aspartylglucosaminuria (AGU) (aspartylglucosaminidase), fucosidosis (α-L-fucosidase enzyme), cystinosis (cystinosin), pycnodysostosis (enzyme cathepsin K), infantile free sialic acid storage disease (solute carrier family 17), among other lysosomal storage disorders known in the art (protein/enzymes are within the brackets after the disease).

In one embodiment, the present invention employs a dual promoter vector that expresses α-galactosidase A (α-gal A) (for example, SEQ ID NO:5) and (IMPDH2(IY)) (SEQ ID NO:7). A suitable nucleic acid sequence encoding α-gal A includes, for example, but not limited to, SEQ ID NO:7 or a sequence that is about 80% sequence identity to SEQ ID NO:7, alternatively at least 85% identity to SEQ ID NO:7, alternatively at least 90% identity to SEQ ID NO:7, alternatively at least 95% sequence identity to SEQ ID NO:7, alternatively at least 98% identity to SEQ ID NO:7, alternatively at least 99% identity to SEQ ID NO:7. A suitable vector includes, for example, but not limited to, SEQ ID NO: 3 or a vector that is about 80% sequence identity to SEQ ID NO:3, alternatively at least 85% identity to SEQ ID NO:3, alternatively at least 90% identity to SEQ ID NO:3, alternatively at least 95% sequence identity to SEQ ID NO:3, alternatively at least 98% identity to SEQ ID NO:3.

In another embodiment, the present invention employs a dual promoter vector that expresses glucocerebrosidase (or beta-glucocerebrosidase, for example encoded by the transgene of SEQ ID NO:6) and IMPDH2(IY) (SEQ ID NO:7). A suitable nucleic acid sequence encoding beta-glucocerebrosidase includes, for example, but not limited to, SEQ ID NO:6 or a sequence that is about 80% sequence identity to SEQ ID NO:6, alternatively at least 85% identity to SEQ ID NO:6, alternatively at least 90% identity to SEQ ID NO:6, alternatively at least 95% sequence identity to SEQ ID NO:6, alternatively at least 98% identity to SEQ ID NO:6, alternatively at least 99% identity to SEQ ID NO:6. A suitable vector includes, for example, but not limited to, SEQ ID NO:4 or a vector that is about 80% sequence identity to SEQ ID NO:4, alternatively at least 85% identity to SEQ ID NO:4, alternatively at least 90% identity to SEQ ID NO:4, alternatively at least 95% sequence identity to SEQ ID NO:4, alternatively at least 98% identity to SEQ ID NO:4.

In another embodiment, the present invention employs a dual promoter vector that expresses acid ceramidase (ASAH1, for example encoded by the transgene of SEQ ID NO:8) and IMPDH2(IY) (SEQ ID NO:7). This vector may be used to transduce HSCs for treatment of Faber disease. A suitable nucleic acid sequence encoding ASAH1 includes, for example, but not limited to, SEQ ID NO:8 or a sequence that is about 80% sequence identity to SEQ ID NO:8, alternatively at least 85% identity to SEQ ID NO:8, alternatively at least 90% identity to SEQ ID NO:8, alternatively at least 95% identity to SEQ ID NO:8, alternatively at least 98% identity to SEQ ID NO:8, alternatively at least 99% identity to SEQ ID NO:8.

In another embodiment, the present invention employs a dual promoter vector that expresses GAA, for example encoded by the transgene of SEQ ID NO:9 and IMPDH2 (IY) (SEQ ID NO:7). This vector may be used for transducing HSCs for treatment of Pompe disease. A suitable nucleic acid sequence encoding GAA includes, for example, but not limited to, SEQ ID NO:9 or a sequence that is about 80% sequence identity to SEQ ID NO:9, alternatively at least 85% identity to SEQ ID NO:9, alternatively at least 90% identity to SEQ ID NO:9, alternatively at least 95% sequence identity to SEQ ID NO:9, alternatively at least 98% identity to SEQ ID NO:9, alternatively at least 99% identity to SEQ ID NO:9.

Figure 8:
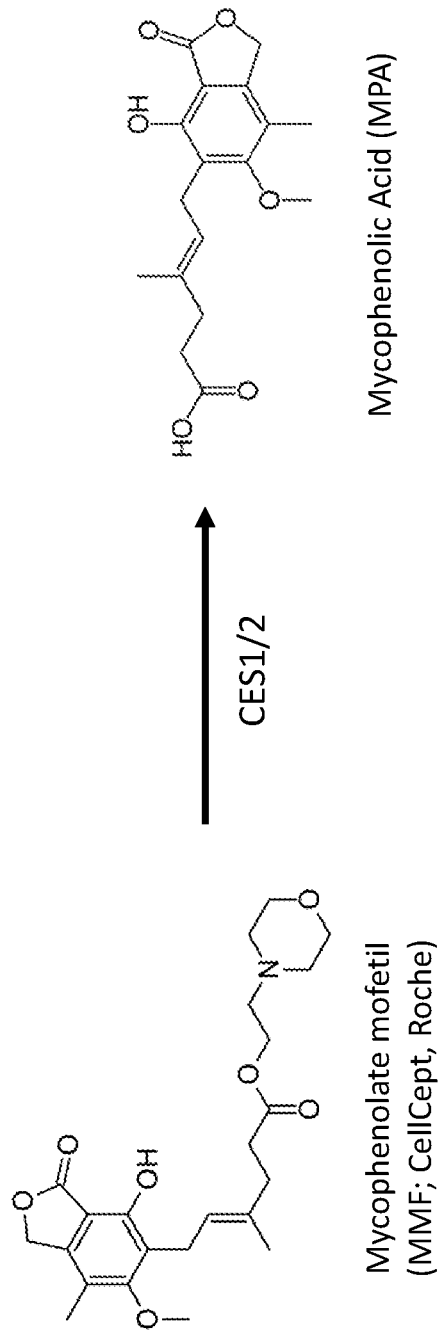
FIG. 8 shows the chemical MMF and its converted form of MPA.
Figure 9:
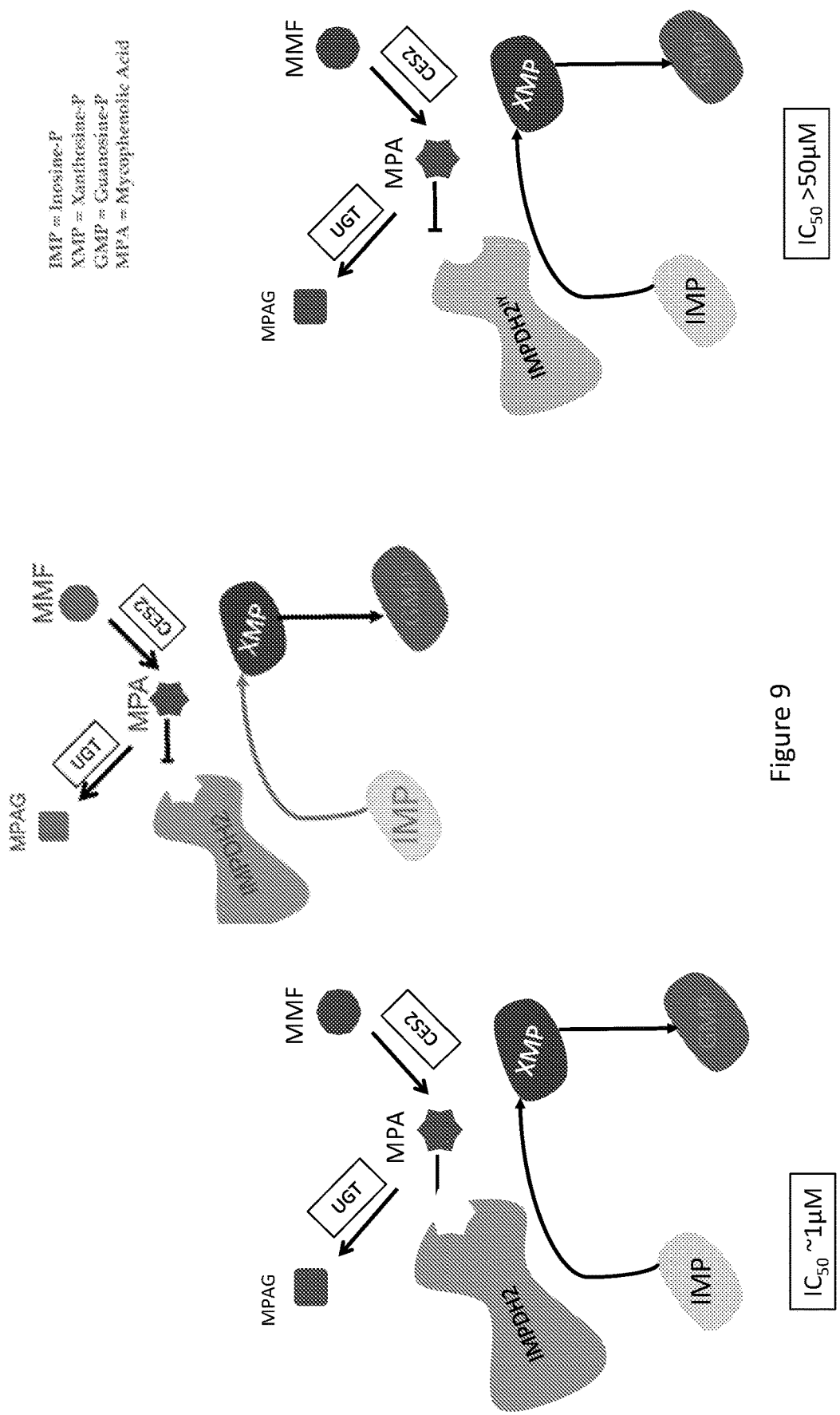
FIG. 9 is a schematic showing the pathway in which MMF works within cells and how the mutant form of IMPDH2 interacts with this pathway.
Figure 10:
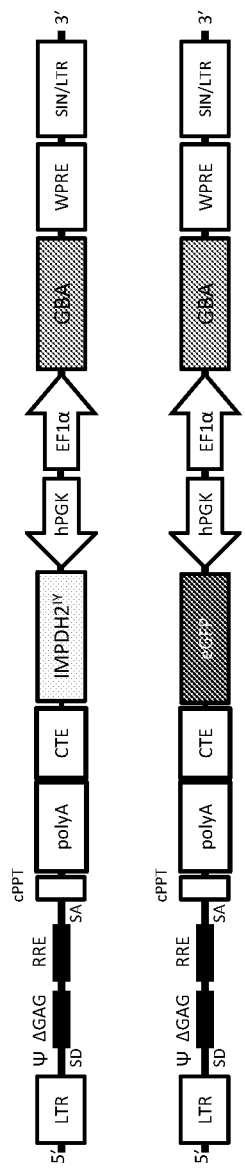
FIG. 10 is a schematic showing other exemplary dual promoter lentiviral vectors expressing GBA protein used in Examples.
Figure 11:
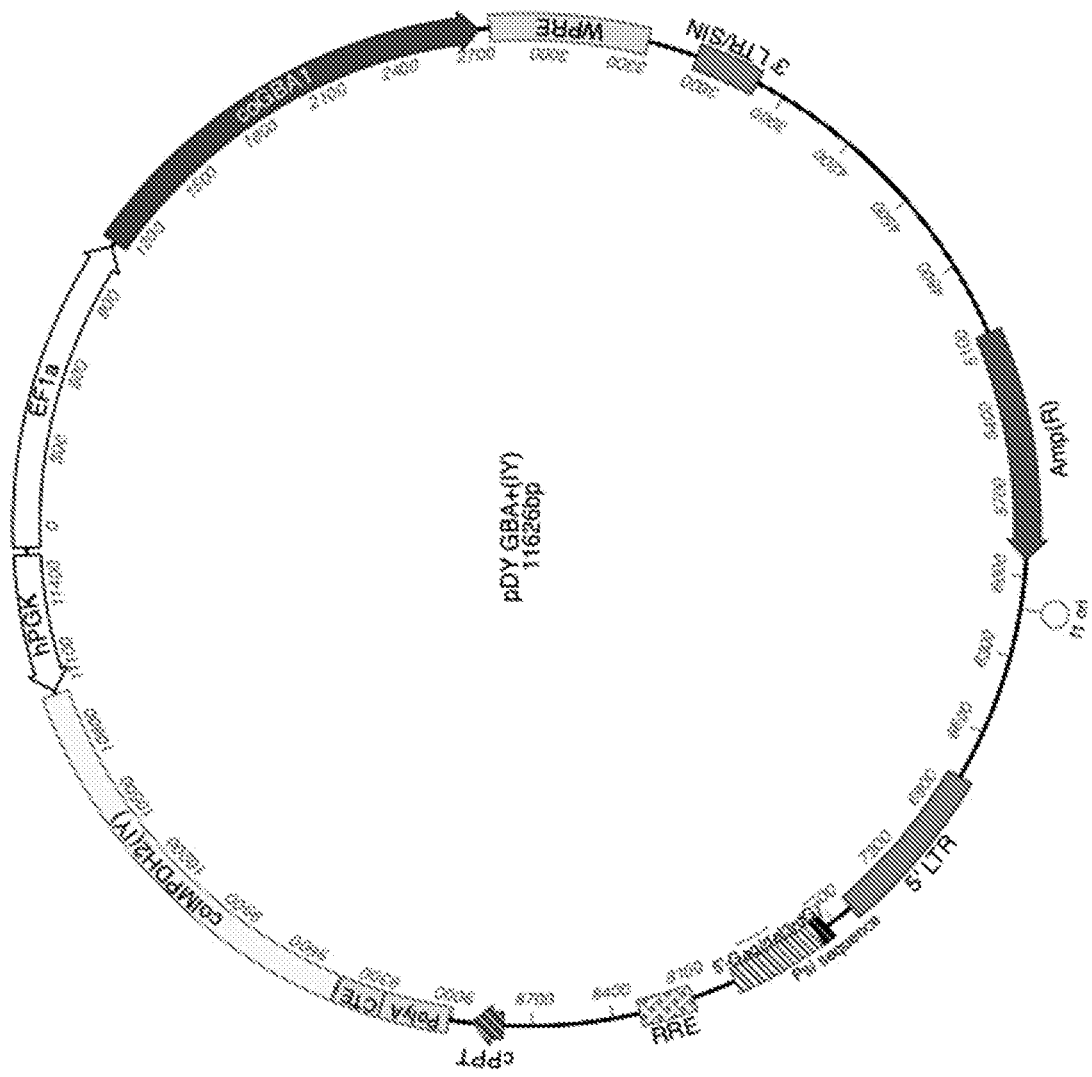
FIG. 11 is a vector map of the dual promoter lentiviral vector that expresses GBA protein and IMPDH2(IY) (SEQ ID NO:4) for use in the treatment of Gaucher disease.

IMPDH2(IY) is resistant to mycophenolic acid (MPA). Mycophenolate Mofetil (MMF) is the pro-drug for MPA and is used routinely in the clinic for a variety of indications, with low incidence of adverse side-effects. FIG. 8 shows the chemical structures of MMF and MPA and FIG. 9 shows the pathway that MMF and/or MPA disrupts through inhibition of IMPDH2(IY), that is, the MPA mechanism of action. MMF is a widely used and well-studied immunosuppressant given by oral administration, it is activated and absorbed by the gut epithelium and also by the liver. MMF has been shown to have minimal occurrence of adverse events at low doses. MMF targets activated lymphocytes and prevents activation induced proliferation of T cells and also prevents maturation of B cells. There is also some evidence that MMF inhibits cytotoxicity of NK cells. MPA is a reversible, non-competitive inhibitor of inosine-5'-monophosphate dehydrogenase (IMPDH). IMPDH is the rate-limiting enzyme in de novo GMP synthesis. T and B cells are highly dependent on IMPDH2, while other tissues can utilize a salvage pathway. Thus, a mutant form of IMPDH2, which has two mutations (T333I and S351Y (IY)) confer resistance to MPA (and thus MMF) in a trans-dominant manner.

The primary consequence of MPA administration is T and B cell depletion. By expressing IMPDH2(IY), T and B cells that arise from transduced and engrafted hematopoietic stem cells (HSCs) are resistant to MPA. Treatment with low doses of MMF can increase the number of therapeutic lymphocytes, without affecting the original engraftment, while causing minimal toxicity. This, in turn, increases the total number of circulating cells that are expressing and secreting the transgene, for example, α-galactosidase A, which can lead to better correction of the disease. Previous attempts at amplification of therapeutic cells have targeted the original HSC engraftment. These strategies either provide HSCs with resistance to cytotoxic agents, or with drug inducible growth modules. Administration of cytotoxic drugs is often associated with severe adverse events, and repeat-administration is also not ideal. Drugs used for inducible growth are not approved for use in patients, limiting their potential. High induction of growth in HSCs can also be associated with stem cell exhaustion, limiting the utility of the graft. Targeting the HSC compartment with a chemical compound is also difficult, due to their unique niche. The aforementioned concerns are ameliorated with the use of our enrichment strategy described herein, since it excludes the HSC compartment.

A suitable nucleic acid sequence encoding for IMPDH2 (IY) is found in SEQ ID NO:7. Suitably, the dual lentiviral vectors comprise SEQ ID NO:7 or a sequence that is about 80% sequence identity to SEQ ID NO:7, alternatively at least 85% identity to SEQ ID NO:7, alternatively at least 90% identity to SEQ ID NO:7, alternatively at least 95% sequence identity to SEQ ID NO:7, alternatively at least 98% identity to SEQ ID NO:7, alternatively at least 99% identity to SEQ ID NO:7. Suitable nucleic acid sequence allow for the expression of IMPDH2(IY) which confers resistance to MPA.

The Examples demonstrate the enrichment of lentiviral-transduced cells in vitro and that this enrichment leads to increased enzyme activity and secretion of enzyme from the cells. Further, we show that this enrichment can be carried out in vivo by administering MMF to the subject.

Current gene therapy involving hematopoietic cells targets correction of cells and engraftment into hosts. The cells are then left on their own to engraft and cure the host. Yet oftentimes the transduction or engraftment efficiency is low. The current method gives a way to enrich for transduced cells in vivo and allows some gating as to how selective and strong that enrichment is depending on the administration of the MMF. The present methods also allow for cells harboring this lentiviral vector to be enriched for even years down the road to renew the correcting cell population expressing the transgene of interest.

In some instances, the dual promoters are promoters known in the art. In one embodiment, the first promoter is hPGK promoter and the second promoter is EF1α promoter. Other promoters are able to be used in the practice of the present invention, as long as the promoters allow for expression of the downstream gene.

In another embodiment, a dual promoter lentiviral vector that expresses α-galactosidase A (encodes the AGA transgene) and IMPDH2(IY) when transduced into a host cell and as such confers resistance to mycophenolic acid (MPA) and/or mycophenolate mofetil (MMF) in vitro and/or in vivo is provided. A suitable dual promoter lentivirus vector that expresses α-galactosidase A and IMPDH2(IY) is depicted in FIG. 2B and the sequence is provided in SEQ ID NO: 3.

In another embodiment, a dual promoter lentiviral vector that expresses a transgene and IMPDH2(IY) when transduced into a host cell is provided. The vector confers resistance to mycophenolic acid (MPA) and/or mycophenolate mofetil (MMF) in vitro and/or in vivo in the host cell. A suitable dual promoter lentivirus vector contains a multiple cloning site to clone the transgene of interest and IMPDH2(IY) is provided in SEQ ID NO: 2.

In some embodiments, the vector comprises the SEQ ID NO:2 wherein the target gene of interest is cloned into the multiple cloning site. Suitable target gene of interests able to be cloned into the multiple cloning site of SEQ ID NO:2 include, but are not limited to, for example, AGA (SEQ ID NO:5), GBA (SEQ ID NO:6), ASAH1 (SEQ ID NO:7) and GAA (SEQ ID NO:9). One skilled in the art would be able to encode the target gene of interest into the vector of SEQ ID NO:2 without undue experimentation.

Methods of treating a patient using the dual promoter lentiviral vector described herein are provided. The method comprises, i) obtaining hematopoietic stem cells (HSCs) from the patient and/or HSCs from a suitable donor, ii) transducing the HSCs ex vivo with a dual promoter lentivirus vector containing IMPDH2(IY) and a transgene (e.g. AGA transgene), iii) introducing the transduced HSCs into the subject, and iv) administering to the subject an amount of mycophenolate mofetil (MMF) sufficient to enrich the population of lentivirus vector transduced hematopoietic cells, for example, T and B cells in the subject.

One embodiment provides a method of treating a subject having a disease associated with a defect in a single protein or enzyme, the method comprising the steps of i) obtaining hematopoietic stem cells (HSCs) from the patient and/or HSCs from a suitable donor, ii) transducing the HSCs ex vivo with a dual promoter lentivirus vector that expresses a suitable form of the protein or enzyme and IMPDH2(IY) in the transduced cells, iii) introducing the transduced HSCs into the subject, and iv) administering to the subject an amount of mycophenolate mofetil (MMF) sufficient to enrich the population hematopoietic cells arising from lentivirus vector transduced HSCs engrafted in the subject.

In some embodiments, the subject has a lysosomal storage disorder (LSD), and the transgene encodes an enzyme or protein associated with the LSD that is deficient in the subject. In some embodiments, the LSD is Fabry disease and the transgene is AGA, the LSD is Gaucher disease and the transgene of interest is GBA, the LSD is Faber disease and the transgene is ASAH1, or the LSD is Pompe and the transgene is GAA.

Another embodiment provides a method of treating Fabry disease patients by:

1) obtaining HSCs from the patient or a suitable donor;
2) transducing the HSCs ex vivo with a dual promoter lentivirus vector that expresses α-gal A and IMPDH2(IY) in the transduced cells;
3) introducing the transduced HSCs and/or hematopoietic cells back into the patient; and,
4) administering mycophenolate mofetil (MMF) to the patient in order to enrich the population of lentivirus vector transduced T and B cells engrafted in the patient, thereby increasing the amount of α-gal A produced in the body. The method treats one or more symptoms of Fabry disease.

In some embodiments, the lysosomal storage disorder is Farber disease (also known as Farber's lipogranulomatosis, ceramidase deficiency, "Fibrocytic dysmucopolysaccharidosis," and "Lipogranulomatosis") and the transgene expresses ASAH1. Farber disease is an extremely rare autosomal recessive lysosomal storage disorder marked by a deficiency in the enzyme acid ceramidase that causes an accumulation of a waxy class of lipids known as sphingolipids, in particular ceramide, leading to abnormalities in the joints, liver, throat, visceral tissues and central nervous system. Suitable embodiments provide T-Rapa cells expressing N-Acylsphingosine Amidohydrolase 1 (ASAH1) for the treatment of Farber disease. As used in the present invention, a suitable dual promoter lentiviral vector expresses ASAH1 and IMPDH2(IY) in the HSC cells. For example, a suitable vector can express ASAH1 using the ASAH1 transgene of SEQ ID NO:8 or a sequence having 80% similarity to SEQ ID NO:8. Suitably, the ASAH1 transgene will have at least 80% similarity to the SEQ ID NO:8, alternatively at least 85% sequence similarity to SEQ ID NO:8, alternatively at least 90% sequence similarity to SEQ ID NO:8, alternatively at least 95% sequence similarity to SEQ ID NO:8, alternatively at least 98% sequence similarity to SEQ ID NO:8, alternatively at least 99% sequence similarity to SEQ ID NO:8, alternatively at least 100% sequence similarity to SEQ ID NO:8.

Pompe disease is an inherited disorder resulting from the buildup of a complex sugar called glycogen in the body's cells resulting in accumulation of glycogen in certain organs and tissues, especially muscles, which impairs their ability to function normally. Mutations within the GAA gene cause Pompe disease as the GAA gene provides instructions for producing an enzyme called acid α-glucosidase (also known as acid maltase). This enzyme is active in lysosomes which serve as recycling centers within cells. The enzyme normally breaks down glycogen in lysosomes into a simpler sugar called glucose, which is the main energy source for most cells. In some embodiments, T-Rapa cells expressing GAA are used to treat a subject having Pompe disease. As described above, dual lentiviral vectors expressing GAA and IMPDH2(IY) transgene within transduced HSCs. In one embodiment, the dual promoter vectors, can express the GAA transgene of SEQ ID NO:9 or a sequence at least 80% similar to SEQ ID NO:9. Suitably, the GAA transgene will have at least 80% similarity to the SEQ ID NO:9, alternatively at least 85% sequence similarity to SEQ ID NO:9, alternatively at least 90% sequence similarity to SEQ ID NO:9, alternatively at least 95% sequence similarity to SEQ ID NO:9, alternatively at least 98% sequence similarity to SEQ ID NO:9, alternatively at least 99% sequence similarity to SEQ ID NO:9, alternatively at least 100% sequence similarity to SEQ ID NO:9.

"Treat" or "treating" includes reducing, inhibiting, or eliminating one or more symptom of the disease or management and care of a subject for the purpose of combating the disease. Treating includes the administration of the HSCs of present invention to prevent or reduce the onset of the symptoms or complications, alleviating the symptoms or complications, or eliminating the disease, condition, or disorder. The aim of treatment includes the alleviation or prevention of symptoms, slowing or stopping the progression or worsening of a disease, disorder, or condition and/or the remission of the disease, disorder or condition. In certain embodiments, the treatment comprises HSCs transduced with the dual promoter and treatment with MMF. The term "treatment" can be characterized by at least one of the following: reducing, ameliorating, slowing or inhibiting one or more symptom of the disease or disorder. In some embodiments, the optimum effective amount can be readily determined by one skilled in the art using routine experimentation.

Symptoms of Fabry disease are known in the art and include, but are not limited to, pain or burning in the hands and/or feet, rash, narrowing of blood vessels, cloudy vision, hearing loss, ringing in the ears, sweating less than normal, stomach pain, kidney problems, high blood pressure, heart failure, enlarged heart, osteoporosis, among others.

In another embodiment, the invention provides a method of treating Gaucher disease by: 1) obtaining HSCs from the patient or a suitable donor; 2) transducing the HSCs ex vivo with a dual promoter lentivirus vector that expresses GBA protein and IMPDH2(IY) in the transduced cells (for example the vector of SEQ ID NO:4); 3) introducing the transduced HSCs and/or hematopoietic cells back into the patient; and, 4) administering mycophenolate mofetil (MMF) to the patient in order to enrich the population of lentivirus vector transduced T and B cells engrafted in the patient, thereby increasing the amount of GBA protein/enzyme produced in the body. The method treats one or more symptoms of Gaucher disease.

Symptoms of Gaucher Disease include, for example, an abnormally enlarged liver and/or spleen (hepatosplenomegaly), low levels of circulating red blood cells (anemia), low levels of platelets (thrombocytopenia), and skeletal abnormalities, among others.

The term "subject" or "patient" are used interchangeably and refer to a mammalian subject, for example, a mouse, a rat, a monkey, a human, etc. In a preferred embodiment, the subject is a human. It is contemplated that the subject or patient may have already been treated with one or more therapies for the lysosomal storage disorder before undergoing the treatment contemplated herein.

The host cell is suitably a hematopoietic cell, for example hematopoietic stem cells (HSCs).

In suitable embodiments, the MMF is administered at an effective dosage. An "effective dosage" refers to a dosage that allows for selective enrichment for T and B cells that express the transgene via the lentiviral vector with minimal side effects. In one embodiment, the effective dosage is a low dosage. Suitable low dosages include, but are not limited to, for example, 0.1-5 mg/kg body weight given TIB (three times a day), alternatively include from about 0.1-3 mg/kg body weight given TIB. Alternatively, the effective dose may include higher doses of MMF. Suitable higher dosage of MMF for practice of this invention include MMF in an amount of about 5-10 mg/kg body weight TID (three times a day), alternatively 1000 mg given BID (two times a day). Suitably, an "effective amount" of MMF will result in a blood concentration within the subject of about 0.4 to about 2 µM free mycophenolic acid (MPA). Suitable dosages to obtain this blood concentration are readily determined by a physician treating the subject. MMF may also be substituted for MPA formulations (Myfortic, Novartis, or approved generic).

Methods of obtaining HSCs from a subject are known in the art. For example an agent may be used to stimulate mobilization of HSCs to the peripheral blood. Suitable agents are known in the art and include, but are not limited to, for example, G-CSF or plerixafor (Mozobil, Sanofi).

HSCs can be transduced ex vivo using a suitable amount of lentivirus, for example, using a MOI (multiplicity of infection) of 1-100, preferably a MOI of 1-30, alternatively a MOI of 1-20, alternatively a MOI of 1-10. The cells may be exposed to the lentivirus for from 10-24 hours, suitably for example for 12 hours. Cytokines may be added to the culture medium during transduction. After transduction, the cells can be either transferred back into the patient or cryopreserved for later transplantation, or a combination of both. In some instances, the transduced cells may be cultured for a number of days before being transferred or cryopreserved. Suitable methods of cryopreservation are known in the art.

Suitable methods of cryopreservation include, but are not limited to, suspending the cells in a cryopreservation medium and storing the cells at −80° C. to −196° C., preferably below −80° C. Suitable cryopreservation media are known in the art and may comprise some combination of base medium, cryopreservative (e.g., DMSO) and a protein source. For example, a suitable cryopreservation medium may comprise complete medium and 10% glycerol, complete medium containing 10% DMSO (dimethlysulfoxide), or 45% cell-conditioned medium with 45% fresh medium and 10% glycerol or DMSO. In alternative embodiments, the cryopreservation medium may be serum free, for example, comprises 46.25% cell-conditioned serum-free medium with 46.25% fresh serum-free medium and 7.5% DMSO.

Subjects may be conditioned before transfer of the hematopoietic cells. Suitable methods of conditioning the patient are known in the art, and include, for example, low-dose regimen (e.g. 30-50% of normal dose) of melphalan or another chemotherapeutic drug. For example, a patient may be treated for 1-3 days by administration once a day with melphalan, as determined by a physician. One skilled in the art of treating the subject will be able to provide an appropriate conditioning regimen. The purpose of conditioning is to reduce the number of endogenous bone marrow cells to provide an advantage to the newly transferred transduced HSCs to engraft and grow.

After conditioning, the patients may receive at least one administration of transduced cells, for example, from about $2\text{-}10\times10^6$ transduced cells/kg body weight intravenously. Suitably amounts of cells include, but are not limited to, e.g. $2\times10^6$ transduced cells/kg, $2.5\times10^6$ transduced cells/kg, $3\times10^6$ transduced cells/kg, $4\times10^6$ transduced cells/kg, $4.5\times10^6$ transduced cells/kg, $5\times10^6$ transduced cells/kg, and include amounts and ranges in between. In some embodiments, subjects may receive additional administration of cells after the first administration at later time points (e.g. hours, days, weeks or months after the first administration). In one embodiment, additional cells may be administered in the same week as the first treatment (e.g. day 2-7) or in the additional weeks post first administration (e.g. week 2-6). In some embodiments, the levels of transgene being expressed can be determined and if the levels become sufficiently low an additional conditioning and/or administration of transduced cells that were cryopreserved can be administered (e.g. weeks or months later).

Timing of MMF doses can be determined by one skilled in the art. In some embodiments, the MMF may be administered during conditioning regimen, depending on the source of the transferring cells. Suitable examples of MMF are described below and MMF can be administered continuously throughout the subject's lifetime or stopped for periods of time or when no longer necessary. In other embodiments, MMF is administered after transfer/engraftment of the transduced HSCs to the subject. Suitably, MMF may be administered for at least 0.5-2 years after engraftment. In some instances, MMF may be administered periodically over the subject's lifetime after transplantation to re-enrich for the transduced cells, e.g. may be administered 5 or 10 years after initial engraftments. MMF may be administered in low dosages continuously, or MMF may be administered non-continuously, for example, MMF may be administered after engraftment for a period of at least six months, followed by a period of time without MMF treatment (e.g. months or years), followed by a restarting of MMF treatment as a "booster" to re-enrich for transduced cells at later time points in the subject's life. Monitoring of transgene protein (e.g. α-gal A) levels within the subject may determine the length of time of administration and dose of MMF, or if additional booster treatment with MMF are needed at later time points after MMF treatment was stopped to re-enrich for more transduced cells to increase the systemic levels of the transgene (e.g. AGA transgene) expressed within the subject. In some embodiments, the transgene may reach suitable levels systemically within the subject where the subject may not need MMF treatment. However, if at later times the transgene systemic levels fall, then MMF treatment can be reinitiated to re-enrich for α-gal A expressing cells.

The methods contemplated herein can be adapted to other LSDs, because the dual promoter lentivirus vector can be modified to express the enzyme (transgene) that is deficient in other LSDs. In addition, there are other disorders, particularly hematopoietic disorders, that the method of the invention can be used to treat, specifically diseases that are related to a single gene defect. For example, hemaptopoeitic disorders that specifically relate to T or B cells may be treated by the methods described herein, including, but not limited to, for example, Wiskott-Aldrich Syndrome with the WAS protein, Leukodystrophies (X-linked and Metachromatic) (ABCD1 gene (adrenoleukodystrophy protein) andARSA gene (arylsufatase A) protein, and the like. Other inherited diseases that are associated with a single gene defect include, but are not limited to, for example, X-linked agammaglbulinemia (BTK gene which encodes the BTK protein), Specifically, in some embodiments, the methods can be used to treat hematopoietic disorders that are able to be treated with transduced hematopoietic stem cells that express a soluble protein encoded by a transgene of interest. For example, one type of suitable diseases are clotting factor deficiencies, for example, hemophilia A, a Factor VIII deficiency, hemphila B, a Factor IX deficiency, Von Willebrand's disease, a von Willebrand factor associated disease. A suitable transgene includes Factor VIII of SEQ ID NO:11, or a sequence that is at least 80% identity to SEQ ID NO:11, alternatively a sequence that has at least 85% identity, alternatively a sequence that has at least 90% identity, alternatively a sequence that has about 95% identity, alternatively a sequence that has at least 98% identity, alternatively a sequence that has about 99% sequence identity. A suitable vector encoding for Factor VIII is found in SEQ ID NO: 12, or a sequence that is at least 80% identity to SEQ ID NO:12, alternatively a sequence that has at least 85% identity, alternatively a sequence that has at least 90% identity, alternatively a sequence that has about 95% identity, alternatively a sequence that has at least 98% identity, alternatively a sequence that has about 99% sequence identity.

In addition, considering that HSCs have been used experimentally to treat a variety of non-hematopoietic diseases including spinal cord injuries, liver cirrhosis, and peripheral vascular disease, the inventors' dual promoter lentivirus vector and in vivo enrichment strategy can be used in the treatment of other diseases by enriching for transduced T and B cell populations that secrete therapeutic proteins targeting other diseases, for example, expression of therapeutic antibodies against tumor cells, or in the treatment of autoimmune diseases.

Current gene therapy involving hematopoietic cells targets correction of cells and engraftment into hosts. The cells are then left on their own to engraft and cure the host. However, the transduction or engraftment efficiency is often low. The current method provides a way to enrich for transduced cells in vivo and allows some degree of "gating" as to how selective and strong that enrichment is. In this regard, cells harboring the lentiviral vector could be enriched for even years down the road to renew the transduced cell population that express the desired transgene.

The invention overcomes the following problems associated with current HSC-based therapies:

Previous attempts at amplification of therapeutic cells have targeted the original HSC engraftment. Such inventions provide HSCs and their progeny with resistance to cytotoxic agents, or with drug inducible growth modules.

Administration of cytotoxic drugs is often associated with severe adverse events, and repeat-administration is also not ideal. MMF is used routinely in the clinic with a low incidence of adverse side-effects.

Drugs used for inducible growth are not approved for use in patients, limiting their potential. High induction of growth in HSCs can also be associated with stem cell exhaustion, limiting the utility of the graft. MMF is a commonly used, FDA approved drug that has no known effect on HSCs.

Targeting the HSC compartment with a chemical compound is also difficult, due to their unique niche. The enrichment strategy disclosed by the inventors would overcome this problem because it excludes the HSC compartment.

Many LSD patients may have been treated with standard of care, which is often enzyme replacement therapy. These therapies may lead to formation of an adaptive immune response against the therapeutic protein of interest, that is, the therapy is recognized as foreign material, for example against the enzyme replacement therapy. One such response is an adaptive immune response, for example formation of therapeutic-specific antibodies which occurs in most patients receiving enzyme replacement therapies, including, but not limited to, Fabry and Pompe disease, reduces the efficacy of the therapy dramatically and leads to clearance of the corrective protein. As such, patients that have pre-existing immune response against the corrective protein treated with gene therapy may have clearance of the therapeutic protein and therefore reduced efficacy. The inventors have observed this occurring in some patients that have been previously treated with enzyme therapy. The current methods described herein overcome the previous problems with standard enzyme replacement therapy in that the MMF used in the present methods not only provides a selective advantage to the transduced cells expressing the enzyme of interest, but also is able to prevent the proliferation of endogenous antibody producing B cells that may react with the therapeutic enzyme. The inventors therefore envision an additional benefit of their platform in that endogenous adaptive immune responses, for example B cells that produce antibodies against the therapeutic protein, can be suppressed in addition to enriching for vector positive B and T cells that should be tolerant and not react to the therapeutic protein. In this way, greater efficacy may be achieved especially in patients whose immune systems are not fully ablated.

Thus the methods of the present invention described herein may be used in patients that are fully ablated, partially ablated or have not undergone ablation prior to treatment with HSCs transduced with the dual promoter lentiviral vector.

"Percentage of sequence identity" or "sequence similarity" is determined by comparing two optimally aligned sequences over a comparison window, wherein the portion of the polynucleotide sequence in the comparison window may comprise substitutions, or additions or deletions (i.e., gaps) as compared to the reference sequence (which does not comprise substitutions, additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "similarity" of polynucleotide sequences means that a polynucleotide comprises a sequence that has at least 80% sequence identity. Suitable sequence similarity allows for small changes in the transgene that do not affect the function of the protein expressed by the transgene. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using programs such as BLAST using standard parameters. These values can be appropriately adjusted to determine corresponding identity of proteins encoded by two nucleotide sequences by taking into account codon degeneracy, amino acid similarity, reading frame positioning and the like.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The invention will be more fully understood upon consideration of the following non-limiting examples.

EXAMPLES

Example 1: Production of Dual Promoter Lentivirus Vectors

The present invention uses dual promoter lentivirus vectors to transfer a transgene and the resistance gene to mycophenolate mofetil (MMF) into the target cell. FIG. 1 shows the vector schematic for some suitable lentiviral vectors for use in the present invention. A dual promoter architecture (pDY-DP (SEQ ID NO:1) was designed and constructed using pDY as a backbone using standard molecular biology techniques. It is contemplated that righother dual promoter architectures and backbones may be used in the practice of the present invention without departing from the scope of the invention. Human-derived ubiquitous, constitutive promoters express transgenes of interest. For enrichment purposes, a vector with IMPDH2(IY) expressed from one promoter was constructed, with the ability to insert another transgene of interest from the other promoter (i.e. pDY-[MCS]+(IY), (SEQ ID NO:2)). A vector with AGA transgene was constructed for use in treating Fabry disease (SEQ ID NO:3) and a vector with GBA transgene was constructed for use in treating Gaucher disease (SEQ ID NO:4). The titer for these vectors are in the range of $1 \times 10^9$ infectious viral particles (IVP)/mL. Vectors with enhanced green fluorescent protein (eGFP) instead of IMPDH2(IY) were used to measure expression and for use as a non-enrichment control. FIGS. 2A-C and 11 show the vector maps of lentiviral vectors used in the present invention.

Figure 3:
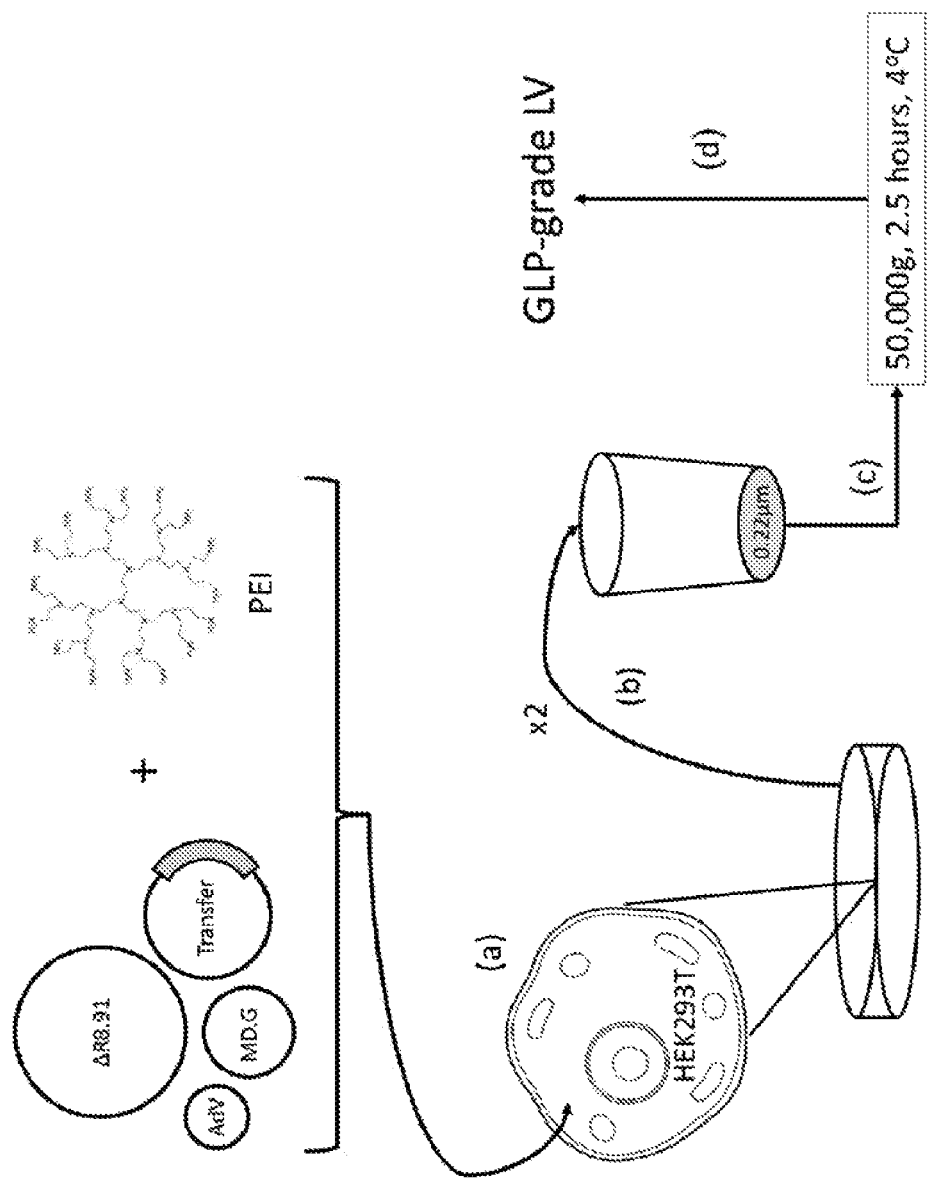
FIG. 3 is a schematic representation of methods of producing lentivirus encoding the transgene and IMPDH2(IY).

Suitable methods of producing lentiviral vectors are known in the art. A suitable protocol is shown in FIG. 3. Production of lentivirus includes the following steps: (a) Three packaging plasmids, pCMVΔR8.91 (Zufferey, et al. Nature Biotechnology 15:871-874, 1997, incorporated by reference), pMD.G (Naldini et al., Science 272:263-267, 1996, incorporated by reference) and pAdV (Promega, USA) are mixed in appropriate ratios with a plasmid encoding the transfer vector of interest. These are complexed with polyethylenimine (PEI) and transfected into HEK293T cells. Media is replaced after 16 hours. (b) Culture supernatant containing virus particles is harvested approximately 40 and 64 hours after transfection. The supernatant is filtered through 0.22 m membrane filters to remove contaminants. (c) Collected supernatant is subjected to ultracentrifugation as indicated to concentrate virus. (d) Viral pellets are resuspended in appropriate media in 2000-fold less volume than the original supernatant.

Figures 4A, 4B:
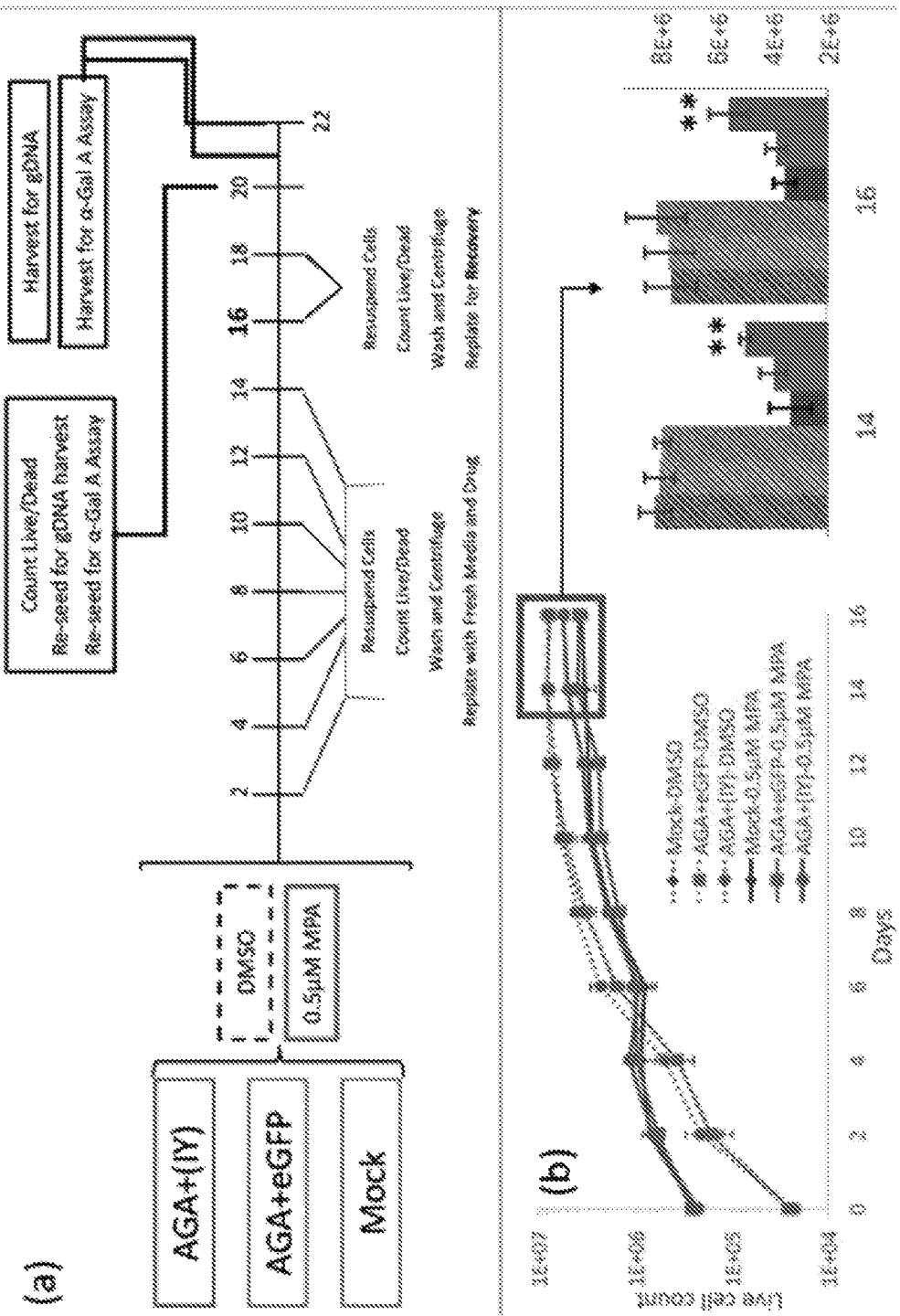
FIG. 4A depicts the schematic for the experiment used for testing the enrichment of cells transduced by the lentivirus in vitro using Jurkat cells.
FIG. 4B depicts the results of live cell count for the different Jurkat cell populations.

Example 2: In Vitro Enrichment of Jurkat Cells Using Dual Promoter Lentiviral Vector and MPA This Example demonstrates that cells expressing the dual promoter lentiviral vector of the present invention can be enriched by treatment of the cells with low doses of MPA in vitro. In this Example, Jurkat cells (immortalized T cells) are used. FIG. 4A shows a schematic for the experiment. 3 cell lines were generated by transducing Jurkat cells with the vectors described or with protamine sulphate only as a mock. VCN/genome was adjusted by dilution of the transduced cells with mock transduced cells. Each of these were seeded in 4 replicates and either treated with DMSO (vehicle) or 0.5 µM MPA. Fresh media with drug or vehicle was added after centrifuging the cells and discarding old media every two days. Samples were taken for cell counts. After 16 days of treatment, cells were reseeded for recovery in fresh media for a total of four days, after which they were counted and reseeded again for two days for α-gal A activity assay or one day for gDNA.

FIG. 4B shows cell counts for all groups. Dead cells were excluded using Trypan blue staining. The panel on the right shows an expanded view of days 14 and 16 ($p<0.01$, student's T Test compared to either negative control).

FIG. 4C shows results of vector copy number (VCN)/genome. VCN was determined by comparison to a standard curve using a qPCR based method and normalized to the number of beta actin (ACTB) copies to determine a per genome value. Patterned bars in the chart refer to samples treated with DMSO and solid bars refer to those treated with MPA. FIG. 4C shows about an 8-fold increase in the vector copy number of the total population per genome.

FIG. 4D demonstrates live vector copies after treatment. These were calculated by multiplying VCN/genome to live cell counts on Day 16. These values may be considered an approximation of vector positive cells after enrichment, assuming a majority of the transduced cells have one vector copy.

FIGS. 4E and 4F demonstrate α-gal A activity. α-gal A activity was determined using 4-MUG substrate and normalized to protein as determined by BCA assay for cell lysates (4E) or to volume for culture supernatants (4F). As shown, there was a corresponding increase in α-gal A activity that corresponded with the increase in vector copy number per genome.

Figure 5:
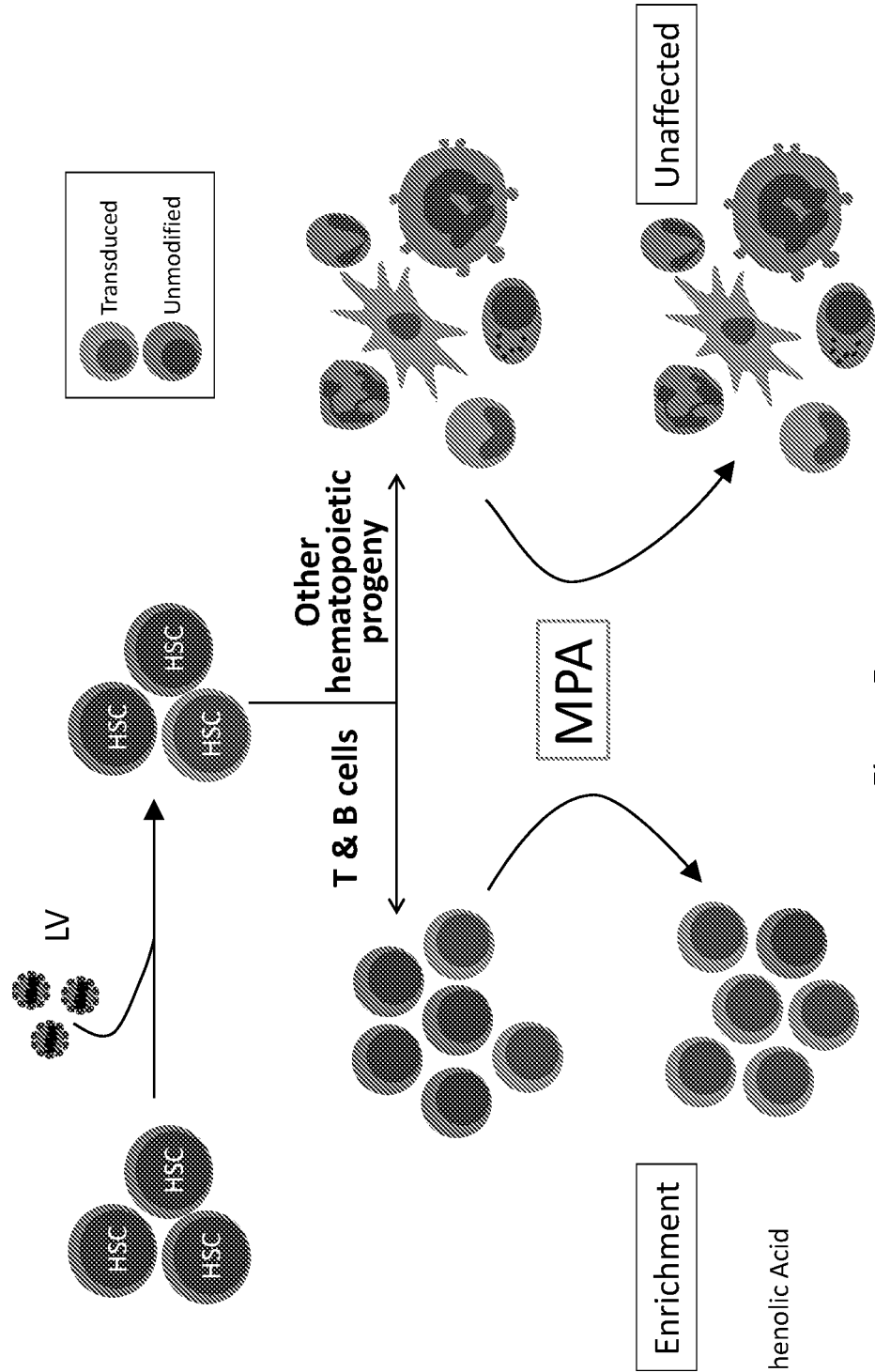
FIG. 5 is a schematic showing how IMPDH2(IY) transduced cells can be selectively enriched by treatment with MMF in vivo.

Thus, IMPDH2(IY) vector can be used to enrich for cells that express the transgene both in vitro and in vivo. FIG. 5 shows a schematic demonstrating how the IMPDH2(IY) enrichment would work using HSC cells.

Example 3: Cell Enrichment In Vivo

Figure 6A:
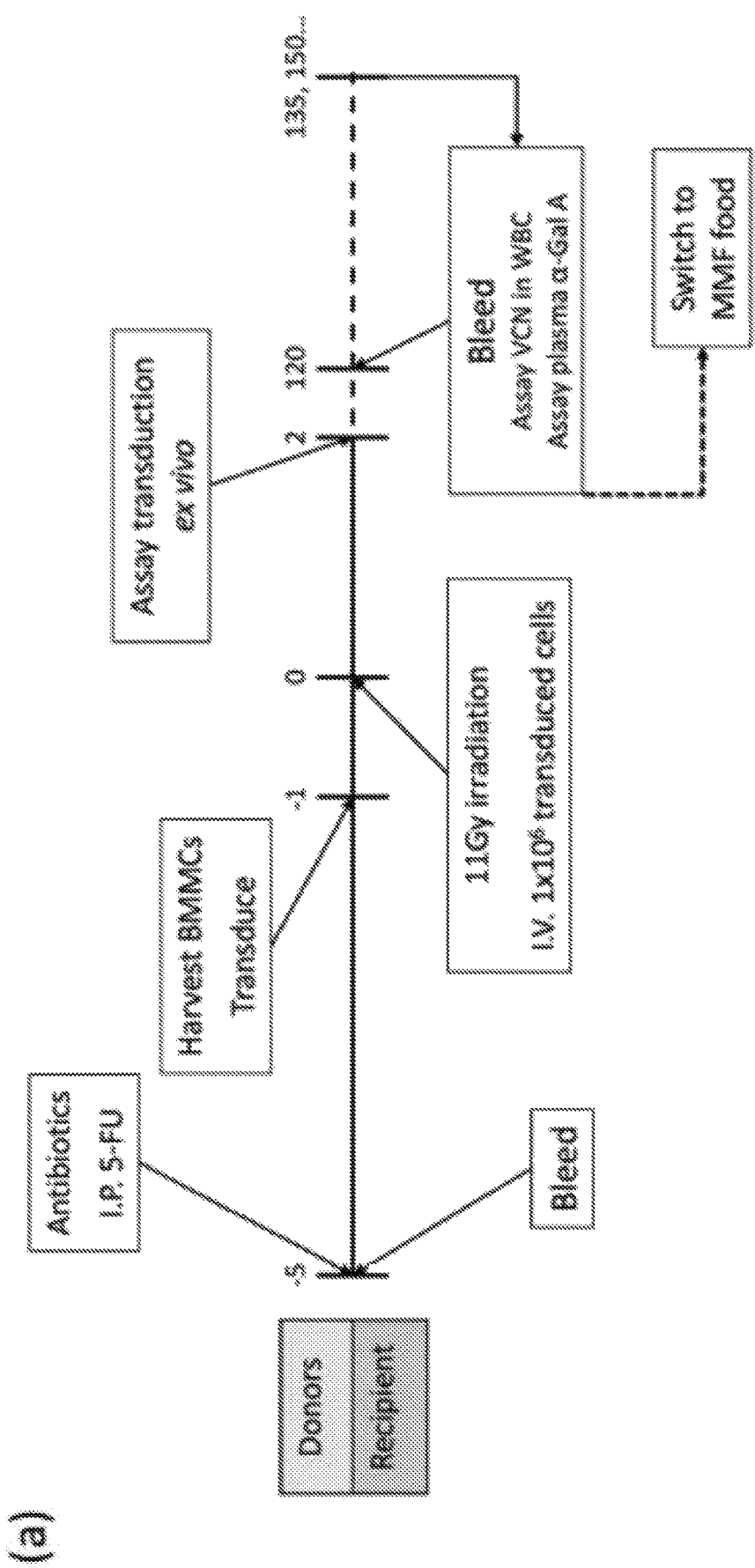
FIG. 6A is a schematic depicting the engraftment procedure for experiments to test enrichment in vivo in a mouse model.
Figure 6B:
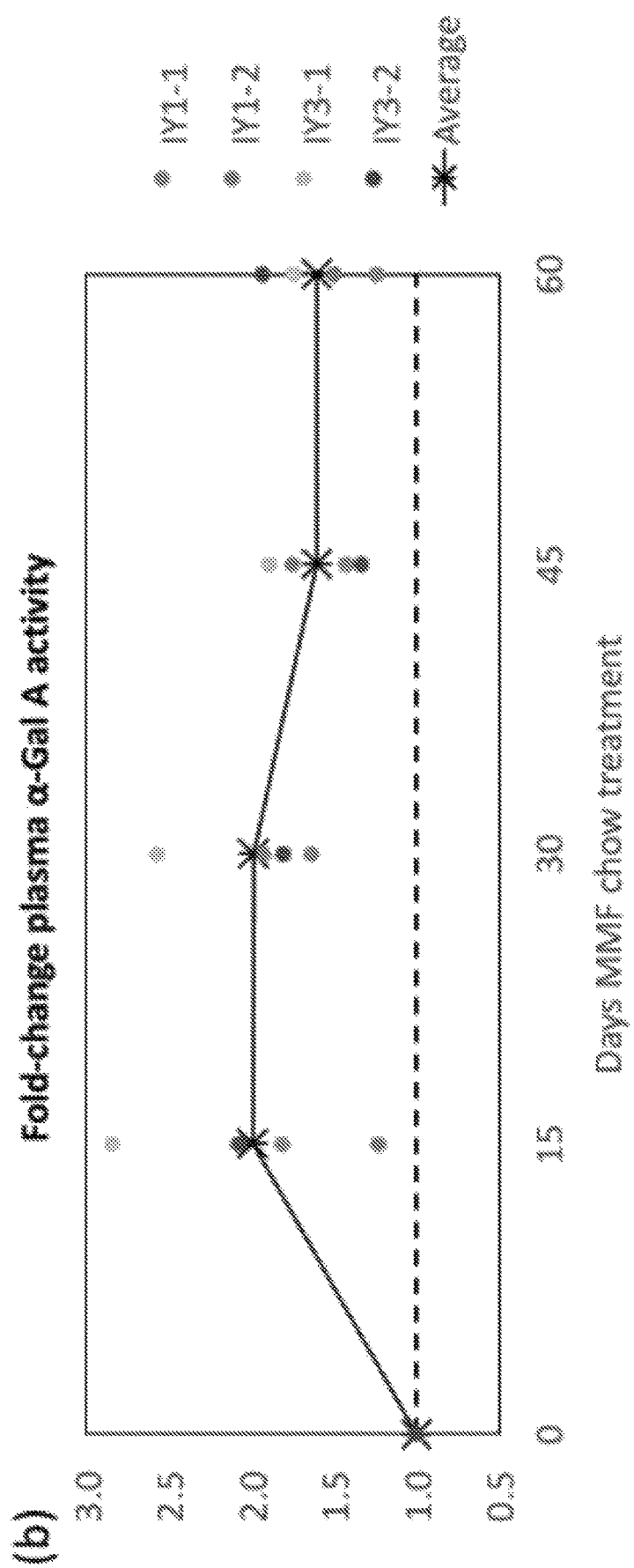
FIG. 6B shows the results of mice engrafted with HSPCs transduced with the dual promoter lentiviral vector after being fed chow containing MMF for 0-60 days.

FIG. 6 shows the experimental schematic for testing enrichment as shown in FIG. 5 in vivo in a mouse model. An experimental schematic for hematopoietic stem progenitor cell (HSPC) engraftment is shown in FIG. 6A. Briefly, male and female Fabry mice aged 2-5 months of age are treated with 5-fluorouracil (5-FU) to deplete bone marrow cells and enrich for HSPCs. Four days after treatment these mice are euthanized, and bone marrow is isolated from femurs and tibia, and processed for transduction. Cells are cultured in stem cell media and transduced using lentivirus described above for 12 hours at a multiplicity of infection (MOI) of 10. Transduced cells are then harvested and prepared for administration to recipient mice. Recipients are male Fabry mice aged approximately 2 months. These are irradiated prior to engrafting transduced cells to deplete their own hematopoietic system. Some cells are retained in culture for an extra 48 hours to assay transduction. Mice are kept on prophylactic antibiotics as support during immune recovery. Engraftment of transduced cells is assessed by measuring VCN/genome in circulation using a qPCR-based assay and comparing to a standard curve, and by measuring plasma α-gal A activity. MMF medicated chow may be started after stable engraftment has been achieved, typically after 4 months. FIG. 6B shows four mice engrafted with LV/AGA+ (IY) transduced cells. Engrafted mice were monitored for ~9 months after engraftment to determine any gross negative effects of IMPDH2(IY) overexpression in the hematopoietic system. No obvious toxicities were observed. A baseline bleed was done to confirm engraftment and the mice were given 0.15% MMF capsule (TEVA generics, Israel) medicated chow ad libitum, and bled every 15 days to observe changes in plasma α-gal A activity, which is a measure of enrichment. Activity was normalized to baseline and are represented as fold-change. No drug-related toxicities were observed in 2 months of treatment.

Example 4: Ex Vivo Gene Therapy for Fabry Disease

Figure 7:
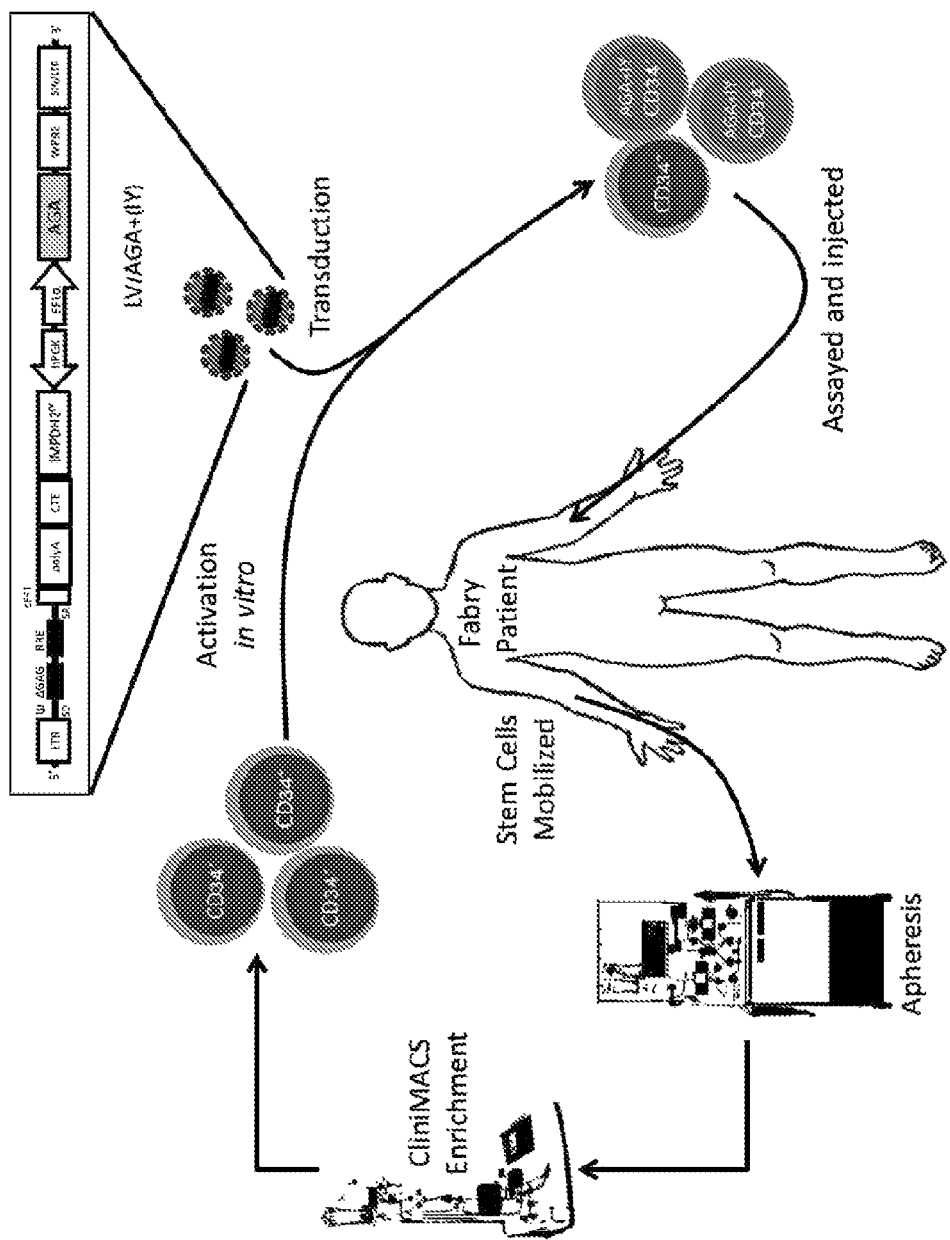
FIG. 7 is a schematic representation of the method of treating a disease using the hematopoietic stem cells transduced with the lentiviral vector of the present invention for Fabry disease.

FIG. 7 demonstrates the overall protocol for treatment of a disorder by the methods described herein, specifically shows the steps for treatment of a lysosomal storage disorder Fabry disease.

Patient hematopoietic stem cells (HSCs) are mobilized to the peripheral blood by appropriate agents, for example G-CSF or plerixafor by known methods in the art. The patient is then subjected to apheresis to collect cells. Cells are then enriched for CD34, a cell surface marker of hematopoietic progenitor cells, using clinical magnet-assisted cell sorting (CliniMACS). The CD34+ cells are then cultured in the presence of cytokines and transduced using lentivirus ex vivo at an MOI of 1-10 for 12 hours, after which they are processed for cryopreservation. The patient may be conditioned using a low-dose regimen (30-50% of normal dose) of melphalan or other chemotherapeutic drug, after which they receive $2-10 \times 10^6$ cells/kg intravenously. Patients are then monitored for hematopoietic reconstitution from transduced cells using plasma enzyme activity and vector copy number (VCN) per genome. Cell administration may be repeated after recovery from conditioning, as recommended by an appropriate physician.

Enrichment can be initiated if required by treatment with mycophenolate mofetil (MMF; CellCept, Roche, or approved generic); transduced T and B cells are resistant to the effects of this drug, providing them with a growth advantage. A low dose of oral MMF may be effective (0.1-5 mg/kg TID) but higher doses (5-10 mg/kg TID or 1000 mg BID) may also be tolerated, depending on the patient. As a general guideline, a blood concentration of 0.4-2 µM free mycophenolic acid (MPA) is desirable. MMF may be administered for the duration for which increased enzyme activity is desired, and doses adjusted to titrate the activity.

MMF may also be substituted for MPA formulations (Myfortic, Novartis, or approved generic).

Example 5: In Vitro Expression of GBA Protein in Transduced Cells

Figure 12:
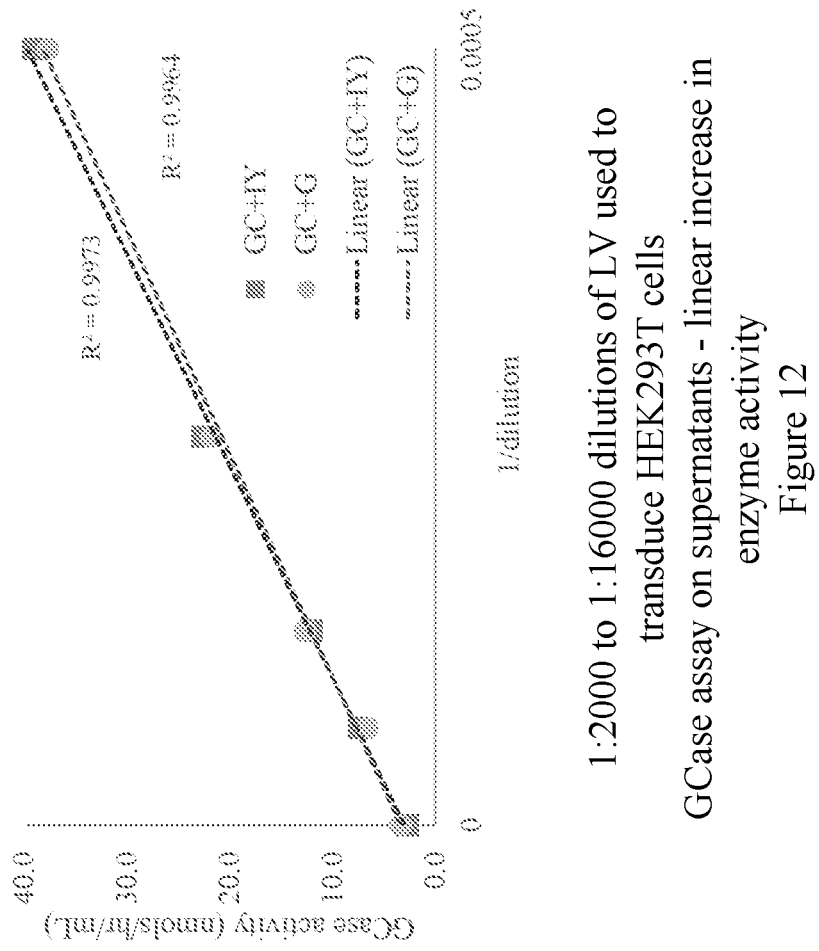
FIG. 12 is a representative graph showing the increase in GBA enzyme activity in culture supernatant of cells transduced with dilutions of LV using the GBA protein expressing lentiviral vectors in FIG. 10.

As demonstrated in FIG. 12, 1:2000 to 1:16000 dilutions of dual promoter lentivirus vector also described in Example 6 that is able to express GBA protein was used to transduce HEK293T cells. Cell supernatant were then monitored for enzyme activity. GCase (GBA protein) assay was performed on supernatants, demonstrating a linear increase in enzyme activity.

Example 6: Gaucher Disease

This Example demonstrates in vitro viral transduction followed by enrichment of Jurkat cells using the viral vectors for expression of GBA protein/enzyme, and increase in GBA enzyme activity in transduced cells.

A codon-optimized copy of the cDNA for GBA transgene was synthesized by GenScript. LV/GBA+(IY) was constructed by inserting the synthesized GBA transgene (SEQ ID NO:6) into the dual promoter backbone (SEQ ID NO:2) at the EF1a locus using standard recombinant technology methods. A control vector with eGFP in place of IMPDH2 (IY) was constructed using similar methods. Lentivirus was packaged as previously described in Example 1; briefly HEK293T were transiently transfected with packaging plasmids and the appropriate transfer vectors, and media replaced 16 hrs later. Supernatant containing viral particles were collected 40 and 64 hrs after transfection, filtered through a 0.22 um membrane and concentrated by centrifugation. Pellets were resuspended in complete culture medium for Jurkat cells (RPMI-1640+10% FBS+Pen/strep/L-glutamine).

Figure 13:
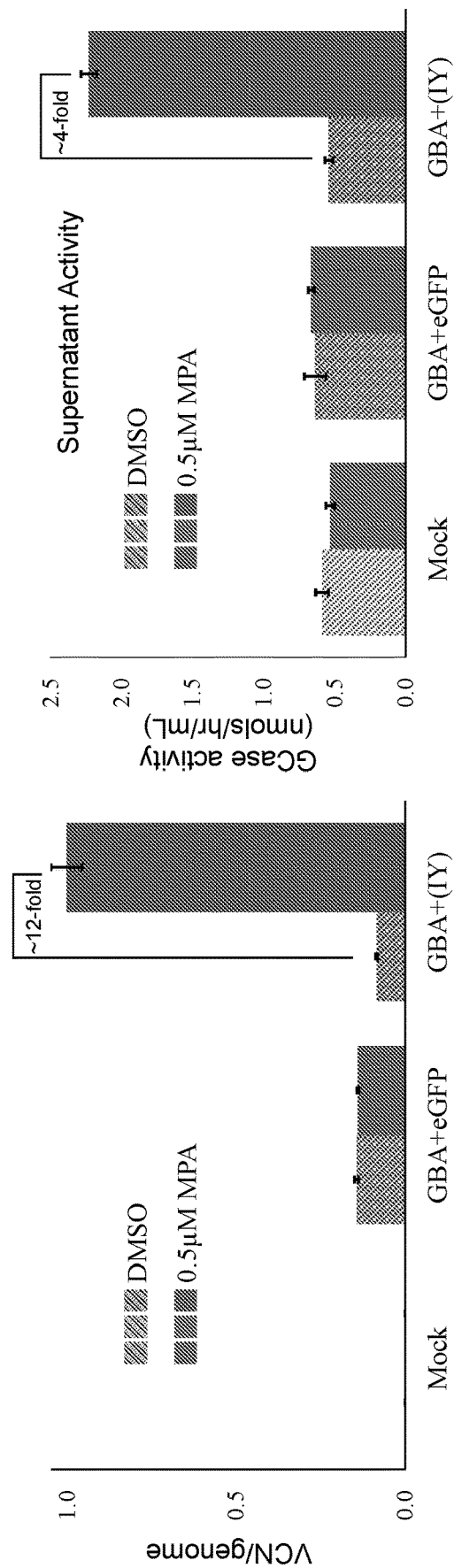
FIG. 13 shows representative experiments demonstrating increased enzyme activity in cell culture supernatant in cells transduced with the GBA+(IY) virus and treated with MPA.

Jurkat cells were transduced with lentivirus at an MOI of ~0.1-0.2. Cells were cultured for at least 2 weeks prior to measuring baseline vector copy number. Cell lines for each of LV/GBA+eGFP and LV/GBA+(IY), or non-transduced cells were produced in this way. To measure enrichment, testing was carried out as described in Example 2. Briefly, cells at known densities were seeded in quadruplicate for each cell line, and maintained in culture for 16 days with either vehicle (DMSO) or 0.5 μM MPA, with media being replaced every two days. After treatment, cells were diluted and recovered for 4-8 days. gDNA was extracted from cells sampled from each well, and vector copy number analyses were carried out using qPCR. Results are shown in FIG. 13. Cells from each well were also seeded at known and equal densities for 72 hours, after which supernatant was collected, cleared of cells and debris, and glucocerebrosidase activity measured using a fluorometric assay. Briefly, supernatants were incubated for 1 hour with substrate solution containing 4-methylumbelliferyl-beta-D-glucopyranoside (15 mM). The reaction was quenched with 0.1M glycine at pH 10 and fluorescence of the reaction product quantified against a calibration curve of the product. Results are shown in FIG. 13.

Each publication, patent, and patent publication cited in this disclosure is incorporated in reference herein in its entirety. The present invention is not intended to be limited to the foregoing examples but encompasses all such modifications and variations as come within the scope of the appended claims.

Figure 2A:
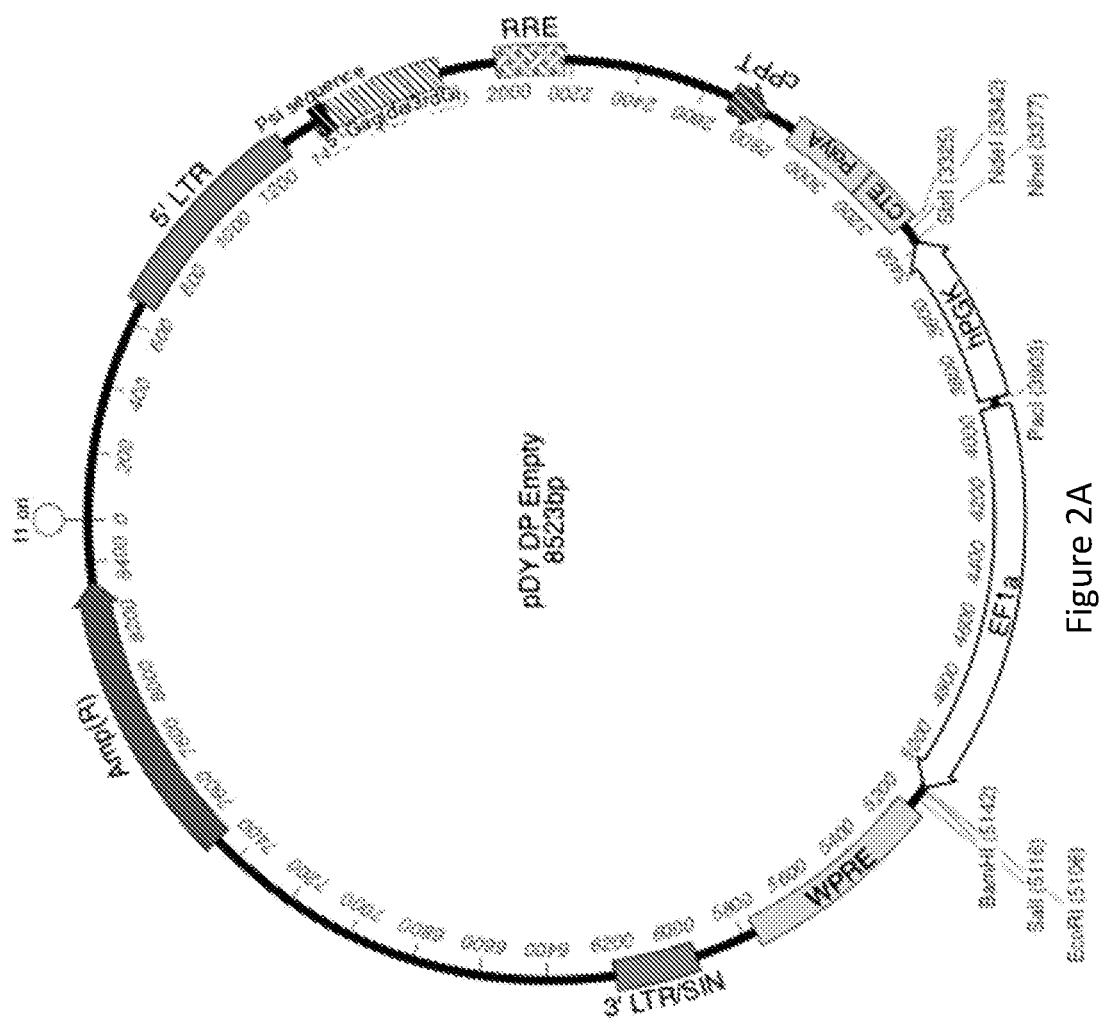
FIG. 2A is a plasmid map of the dual promoter lentiviral vector with two multiple cloning sites (MCS) for cloning of a transgene and a resistance gene.
Figure 2B:
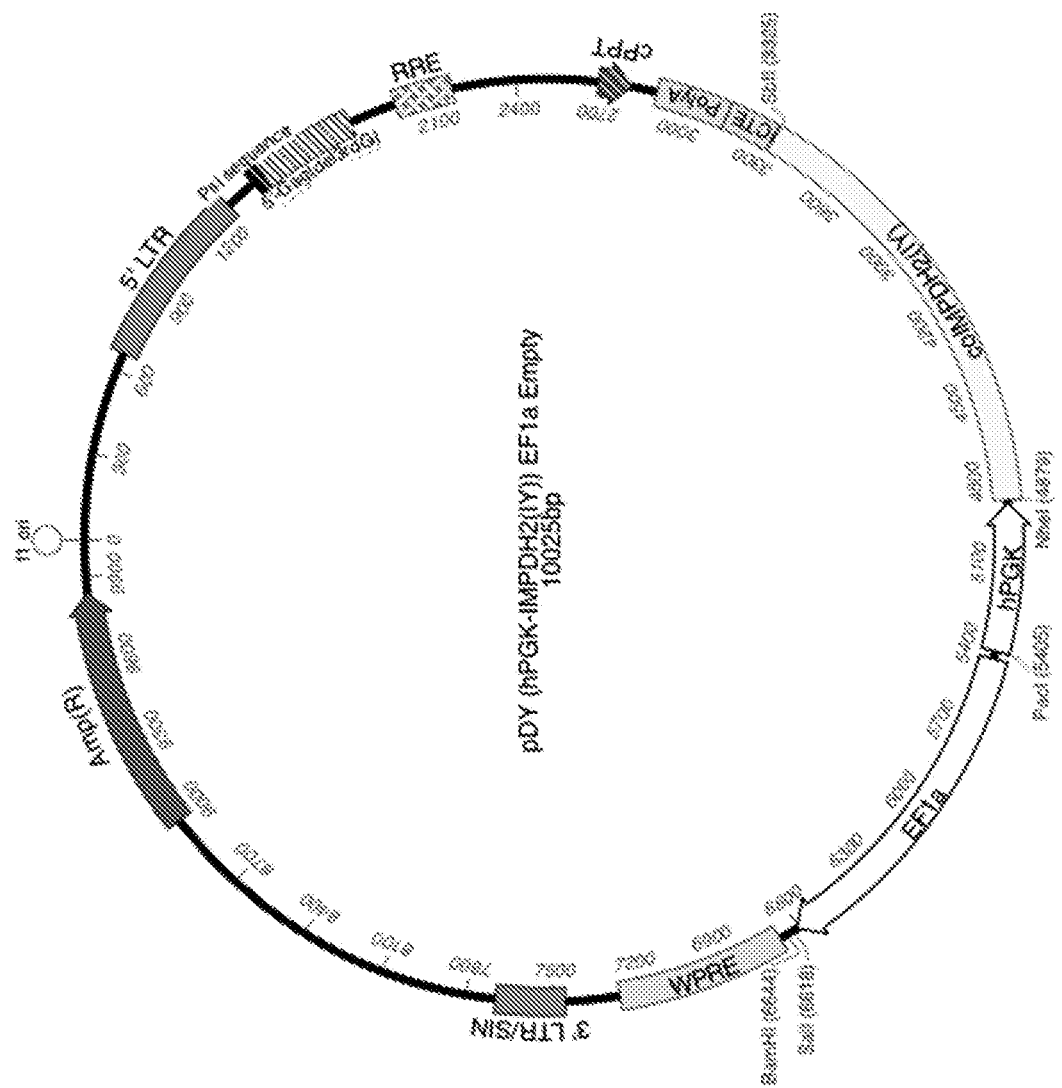
FIG. 2B is a plasmid map of the dual promoter lentiviral vector containing the mutant IMPDH2 gene (IMPDH2(IY)) and a multiple cloning site in which a transgene can be cloned and expressed.
Figure 2C:
FIG. 2C is the plasmid map of the dual promoter lentiviral vector containing the mutant IMPDH2 gene (IMPDH2(IY)) and AGA codon optimized transgene.

```
SEQUENCE LISTING
The following sequences correspond with the plasmid
maps in FIGS. 2A-2C.
Genetic elements of plasmids and lentivirus vectors
f1 ori: Origin of plasmid replication in bacteria
Amp(R): Ampicillin-resistance gene (beta-lactamase)
5' LTR: HIV1-derived 5' Long Terminal Repeat: Viral
element required for integration into host genome
3' LTR/SIN: HIV1-derived 3' Long Terminal Repeat
with a 133 bp deletion to inactivate the capacity
for any viral replication after retrotranscription
in the host cell
Psi sequence: Retroviral Psi packaging element
5'Gag(del3rdG): Viral element required in 2nd
generation lentivirus systems for proviral RNA
transcription
RRE: Viral REV response element, required for
nuclear export of proviral RNA
cPPT: central polypurine tract, a lentiviral
element that enhances nuclear import/export of
viral RNA, consequently enhancing viral titer and
transduction.
EF1a: Ubiquitous, constitutively expressing
promoter derived from the human elongation factor
1 alpha gene
WPRE: Woodchuck Hepatitis post-transcriptional
regulatory element; potently terminates
transcription and stabilizes mRNA.
hPGK: Ubiquitous, constitutively expressing
promoter derived from the human phosphoglycerate
kinase 1 gene
CTE and polyA: C-Terminal end and polyA signal
sequence for termination of transcription
coIMPDH2(IY): codon optimized transgene expressing
the T333I, S351Y mutant of human 5'-inosine
monophosphate dehydrogenase 2
AGA: Codon optimized transgene encoding human
α-galactosidase A
GBA-codon optimized transgene for
glucocerebrosidase (GBA protein)
>pDY DP Empty (SEQ ID NO: 1)
AAATTGTAAGCGTTAATATTTTGTTAAAATTCGCGTTAAATTTTTGTTAA

ATCAGCTCATTTTTTAACCAATAGGCCGAAATCGGCAAAATCCCTTATAA

ATCAAAAGAATAGACCGAGATAGGGTTGAGTGTTGTTCCAGTTTGGAACA

AGAGTCCACTATTAAAGAACGTGGACTCCAACGTCAAAGGGCGAAAAACC

GTCTATCAGGGCGATGGCCCACTACGTGAACCATCACCCTAATCAAGTTT

TTTGGGGTCGAGGTGCCGTAAAGCACTAAATCGGAACCCTAAAGGGAGCC

CCCGATTTAGAGCTTGACGGGGAAAGCCGGCGAACGTGGCGAGAAAGGAA

GGGAAGAAAGCGAAAGGAGCGGGCGCTAGGGCGCTGGCAAGTGTAGCGGT

CACGCTGCGCGTAACCACCACACCCGCCGCGCTTAATGCGCCGCTACAGG

GCGCGTCCATTCGCCATTCAGGCTGCGCAACTGTTGGGAAGGGCGATCGG

TGCGGGCCTCTTCGCTATTACGCCAGCTGGCGAAAGGGGGATGTGCTGCA

AGGCGATTAAGTTGGGTAACGCCAGGGTTTTCCCAGTCACGACGTTGTAA

AACGACGGCCAGTGAATTGTAATACGACTCACTATAGGGCGAATTGGGCC

CGACGTCGCATGCTTGGAAGGGCTAATTCACTCCCAAAGAAGACAAGATA

TCCTTGATCTGTGGATCTACCACACACAAGGCTACTTCCCTGATTAGCAG

AACTACACACCAGGGCCAGGGGTCAGATATCCACTGACCTTTGGATGGTG

CTACAAGCTAGTACCAGTTGAGCCAGATAAGGTAGAAGAGGCCAATAAAG

GAGAGAACACCAGCTTGTTACACCCTGTGAGCCTGCATGGGATGGATGAC

CCGGAGAGAGAAGTGTTAGAGTGGAGGTTTGACAGCCGCCTAGCATTTCA

TCACGTGGCCCGAGAGCTGCATCCGGAGTACTTCAAGAACTGCTGATATC
```

-continued

GAGCTTGCTACAAGGGACTTTCCGCTGGGACTTTCCAGGGAGGCGTGGC
CTGGGCGGGACTGGGGAGTGGCGAGCCCTCAGATCCTGCATATAAGCAGC
TGCTTTTTGCCTGTACTGGGTCTCTCTGGTTAGACCAGATCTGAGCCTGG
GAGCTCTCTGGCTAACTAGGGAACCCACTGCTTAAGCCTCAATAAAGCTT
GCCTTGAGTGCTTCAAGTAGTGTGTGCCCGTCTGTTGTGTGACTCTGGTA
ACTAGAGATCCCTCAGACCCTTTTAGTCAGTGTGGAAAATCTCTAGCAGT
GGCGCCCGAACAGGGACTTGAAAGCGAAAGGGAAACCAGAGGAGCTCTCT
CGACGCAGGACTCGGCTTGCTGAAGCGCGCACGGCAAGAGGCGAGGGGCG
GCGACTGGTGAGTACGCCAAAAATTTTGACTAGCGGAGGCTAGAAGGAGA
GAGATGGGTGCGAGAGCGTCAGTATTAAGCGGGGGAGAATTAGATCGCGA
TGGGAAAAAATTCGGTTAAGGCCAGGGGGAAAGAAAAAATATAAATTAAA
ACATATAGTATGGGCAAGCAGGGAGCTAGAACGATTCGCAGTTAATCCTG
GCCTGTTAGAAACATCAGAAGGCTGTAGACAAATACTGGGACAGCTACAA
CCATCCCTTCAGACAGGATCAGAAGAACTTAGATCATTATATAATACAGT
AGCAACCCTCTATTGTGTGCATCAAAGGATAGAGATAAAAGACACCAAGG
AAGCTTTAGACAAGATAGAGGAAGAGCAAAACAAAAGTAAGACCACCGCA
CAGCAAGCGGCCGCTGATCTTCAGACCTGGAGGAGGAGATATGAGGGACA
ATTGGAGAAGTGAATTATATAAATATAAAGTAGTAAAAATTGAACCATTA
GGAGTAGCACCCACCAAGGCAAAGAGAAGAGTGGTGCAGAGAGAAAAAAG
AGCAGTGGGAATAGGAGCTTTGTTCCTTGGGTTCTTGGGAGCAGCAGGAA
GCACTATGGGCGCAGCGTCAATGACGCTGACGGTACAGGCCAGACAATTA
TTGTCTGGTATAGTGCAGCAGCAGAACAATTTGCTGAGGGCTATTGAGGC
GCAACAGCATCTGTTGCAACTCACAGTCTGGGGCATCAAGCAGCTCCAGG
CAAGAATCCTGGCTGTGGAAAGATACCTAAAGGATCAACAGCTCCTGGGG
ATTTGGGGTTGCTCTGGAAAACTCATTTGCACCACTGCTGTGCCTTGAA
TGCTAGTTGGAGTAATAAATCTCTGGAACAGATTTGGAATCACACGACCT
GGATGGAGTGGGACAGAGAAATTAACAATTACACAAGCTTAATACACTCC
TTAATTGAAGAATCGCAAAACCAGCAAGAAAAGAATGAACAAGAATTATT
GGAATTAGATAAATGGGCAAGTTTGTGGAATTGGTTTAACATAACAAATT
GGCTGTGGTATATAAAATTATTCATAATGATAGTAGGAGGCTTGGTAGGT
TTAAGAATAGTTTTTGCTGTACTTTCTATAGTGAATAGAGTTAGGCAGGG
ATATTCACCATTATCGTTTCAGACCCACCTCCCAACCCCGAGGGGACCCG
ACAGGCCCGAAGGAATAGAAGAAGAAGGTGGAGAGAGAGACAGAGACAGA
TCCATTCGATTAGTGAACGGATCTCGACGGGATCGATTTTAAAAGAAAAG
GGGGGATTGGGGGGTACAGTGCAGGGGAAAGAATAGTAGACATAATAGCA
ACAGACATACAAACTAAAGAATTACAAAAACAAATTACAAAAATTCAAAA
TTTTATCGATAAGCTTTGCAAAGATGGATAAAGTTTTAAACAGAGAGGAA
TCTTTGCAGCTAATGGACCTTCTAGGTCTGACCCCGTACGCCTCGAGAGA
TCTGATCATAATCAGCCATACCACATTTGTAGAGGTTTTACTTGCTTTAA
AAAACCTCCCACACCTCCCCCTGAACCTGAAACATAAAATGAATGCAATT
GTTGTTGTTAACTTGTTTATTGCAGCTTATAATGGTTACAAATAAGGCAA

-continued

TAGCATCACAAATTTCACAAATAAGGCATTTTTTTCACTGCATTCTAGTT
TTGGTTTGTCCAAACTCATCAATGTATCTTATCATGTCTGGATCTCAAAT
CCCTCGGAAGCTGCGCCTGTCTTAGGTTGGAGTGATACATTTTTATCACT
TTTACCCGTCTTTGGATTAGGCAGTAGCTCTGACGGCCCTCCTGTCTTAG
GTTAGTGAAAAATGTCACTCTCTTACCCGTCATTGGCTGTCCAGCTTAGC
TCGCAGGGGAGGTGGTCTGCCTGCAGGCGGATGGCGTTAACATATGACAA
CTTTCTCCCGGGTAATCTGACCGTTCGCTAGCCCTGGGGAGAGAGGTCGG
TGATTCGGTCAACGAGGGAGCCGACTGCCGACGTGCGCTCCGGAGGCTTG
CAGAATGCGGAACACCGCGCGGGCAGGAACAGGGCCCACACTACCGCCCC
ACACCCCGCCTCCCGCACCGCCCCTTCCCGGCCGCTGCTCTCGGCGCGCC
CCGCTGAGCAGCCGCTATTGGCCACAGCCCATCGCGGTCGGCGCGCTGCC
ATTGCTCCCTGGCGCTGTCCGTCTGCGAGGGTACTAGTGAGACGTGCGGC
TTCCGTTTGTCACGTCCGGCACGCCGCGAACCGCAAGGAACCTTCCCGAC
TTAGGGGCGGAGCAGGAAGCGTCGCCGGGGGGCCCACAAGGGTAGCGGCG
AAGATCCGGGTGACGCTGCGAACGGACGTGAAGAATGTGCGAGACCCAGG
GTCGGCGCCGCTGCGTTTCCCGGAACCACGCCCAGAGCAGCCGCGTCCCT
GCGCAAACCCAGGGCTGCCAAGGAAAAGGCGCAACCCCAACCCCGTGGTT
AATTAAGGTGAAAGGAGTGGGAATTGGCTCCGGTGCCCGTCAGTGGGCAG
AGCGCACATCGCCCACAGTCCCCGAGAAGTTGGGGGGAGGGGTCGGCAAT
TGAACCGGTGCCTAGAGAAGGTGGCGCGGGGTAAACTGGGAAAGTGATGT
CGTGTACTGGCTCCGCCTTTTTCCCGAGGGTGGGGGAGAACCGTATATAA
GTGCAGTAGTCGCCGTGAACGTTCTTTTTCGCAACGGGTTTGCCGCCAGA
ACACAGGTAAGTGCCGTGTGTGGTTCCCGCGGGCCTGGCCTCTTTACGGG
TTATGGCCCTTGCGTGCCTTGAATTACTTCCACCTGGCTGCAGTACGTGA
TTCTTGATCCCGAGCTTCGGGTTGGAAGTGGGTGGGAGAGTTCGAGGCCT
TGCGCTTAAGGAGCCCCTTCGCCTCGTGCTTGAGTTGAGGCCTGGCCTGG
GCGCTGGGGCCGCCGCGTGCGAATCTGGTGGCACCTTCGCGCCTGTCTCG
CTGCTTTCGATAAGTCTCTAGCCATTTAAAATTTTTGATGACCTGCTGCG
ACGCTTTTTTTCTGGCAAGATAGTCTTGTAAATGCGGGCCAAGATCTGCA
CACTGGTATTTCGGTTTTTGGGGCCGCGGGCGGCGACGGGGCCCGTGCGT
CCCAGCGCACATGTTCGGCGAGGCGGGGCCTGCGAGCGCGGCCACCGAGA
ATCGGACGGGGTAGTCTCAAGCTGGCCGGCCTGCTCTGGTGCCTGGCCT
CGCGCCGCCGTGTATCGCCCCGCCCTGGGCGGCAAGGCTGGCCCGGTCGG
CACCAGTTGCGTGAGCGGAAAGATGGCCGCTTCCCGGCCCTGCTGCAGGG
AGCTCAAAATGGAGGACGCGGCGCTCGGGAGAGCGGGCGGGTGAGTCACC
CACACAAAGGAAAAGGGCCTTTCCGTCCTCAGCCGTCGCTTCATGTGACT
CCACGGAGTACCGGGCGCCGTCCAGGCACCTCGATTAGTTCTCGAGCTTT
TGGAGTACGTCGTCTTTAGGTTGGGGGGAGGGGTTTTATGCGATGGAGTT
TCCCCACACTGAGTGGGTGGAGACTGAAGTTAGGCCAGCTTGGCACTTGA
TGTAATTCTCCTTGGAATTTGCCCTTTTTGAGTTTGGATCTTGGTTCATT
CTCAAGCCTCAGACAGTGGTTCAAAGTTTTTTTCTTCCATTTCAGGTGTC

-continued

```
GTGAGGAATTCTGCAGTCGACGGTACCGCGGGCGCGCCCCGGGATCCAAG
CTTCAATTGTGGTCACTCGACAATCAACCTCTGGATTACAAAATTTGTGA
AAGATTGACTGGTATTCTTAACTATGTTGCTCCTTTTACGCTATGTGGAT
ACGCTGCTTTAATGCCTTTGTATCATGCTATTGCTTCCCGTATGGCTTTC
ATTTTCTCCTCCTTGTATAAATCCTGGTTGCTGTCTCTTTATGAGGAGTT
GTGGCCCGTTGTCAGGCAACGTGGCGTGGTGTGCACTGTGTTTGCTGACG
CAACCCCCACTGGTTGGGGCATTGCCACCACCTGTCAGCTCCTTTCCGGG
ACTTTCGCTTTCCCCCTCCCTATTGCCACGGCGGAACTCATCGCCGCCTG
CCTTGCCCGCTGCTGGACAGGGGCTCGGCTGTTGGGCACTGACAATTCCG
TGGTGTTGTCGGGGAAGCTGACGTCCTTTCCATGGCTGCTCGCCTGTGTT
GCCACCTGGATTCTGCGCGGGACGTCCTTCTGCTACGTCCCTTCGGCCCT
CAATCCAGCGGACCTTCCTTCCCGCGGCCTGCTGCCGGCTCTGCGGCCTC
TTCCGCGTCTTCGCCTTCGCCCTCAGACGAGTCGGATCTCCCTTTGGGCC
GCCTCCCCGCCTGCTCGAGACCTAGAAAAACATGGAGCAATCACAAGTAG
CAATACAGCAGCTACCAATGCTGATTGTGCCTGGCTAGAAGCACAAGAGG
AGGAGGAGGTGGGTTTTCCAGTCACACCTCAGGTACCTTTAAGACCAATG
ACTTACAAGGCAGCTGTAGATCTTAGCCACTTTTTAAAAGAAAAGGGGGG
ACTGGAAGGGCTAATTCACTCCCAACGAAGACAAGATCTGCTTTTTGCTT
GTACTGGGTCTCTCTGGTTAGACCAGATCTGAGCCTGGGAGCTCTCTGGC
TAACTAGGGAACCCACTGCTTAAGCCTCAATAAAGCTTGCCTTGAGTGCT
TCAAGTAGTGTGTGCCCGTCTGTTGTGTGACTCTGGTAACTAGAGATCCC
TCAGACCCTTTTAGTCAGTGTGGAAAATCTCTAGCAGTAGTAGTTCATGT
CATCTTATTATTCAGTATTTATAACTTGCAAAGAAATGAATATCAGAGAG
TGAGAGGACGCGTTGGATGCATAGCTTGAGTATTCTATAGTGTCACCTAA
ATAGCTTGGCGTAATCATGGTCATAGCTGTTTCCTGTGTGAAATTGTTAT
CCGCTCACAATTCCACACAACATACGAGCCGGAAGCATAAAGTGTAAAGC
CTGGGGTGCCTAATGAGTGAGCTAACTCACATTAATTGCGTTGCGCTCAC
TGCCCGCTTTCCAGTCGGGAAACCTGTCGTGCCAGCTGCATTAATGAATC
GGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTAT
CAGCTCACTCAAAGGCGGTAATACGGTTATCCACAGAATCAGGGGATAAC
GCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGAC
ACGACTTATCGCCACTGGCAGCAGCCACTGGTAACAGGATTAGCAGAGCG
AGGTATGTAGGCGGTGCTACAGAGTTCTTGAAGTGGTGGCCTAACTACGG
CTACACTAGAAGAACAGTATTTGGTATCTGCGCTCTGCTGAAGCCAGTTA
CCTTCGGAAAAGAGTTGGTAGCTCTTGATCCGGCAAACAAACCACCGCT
GGTAGCGGTGGTTTTTTTGTTTGCAAGCAGCAGATTACGCGCAGAAAAAA
AGGATCTCAAGAAGATCCTTTGATCTTTTCTACGGGGTCTGACGCTCAGT
GGAACGAAAACTCACGTTAAGGGATTTTGGTCATGAGATTATCAAAAAGG
ATCTTCACCTAGATCCTTTTAAATTAAAAATGAAGTTTTAAATCAATCTA
AAGTATATATGAGTAAACTTGGTCTGACAGTTACCAATGCTTAATCAGTG
AGGCACCTATCTCAGCGATCTGTCTATTTCGTTCATCCATAGTTGCCTGA
CTCCCCGTCGTGTAGATAACTACGATACGGGAGGGCTTACCATCTGGCCC
CAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCA
ACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGT
TCCCAACGATCAAGGCGAGTTACATGATCCCCCATGTTGTGCAAAAAAGC
GGTTAGCTCCTTCGGTCCTCCGATCGTTGTCAGAAGTAAGTTGGCCGCAG
TGTTATCACTCATGGTTATGGCAGCACTGCATAATTCTCTTACTGTCATG
CCATCCGTAAGATGCTTTTCTGTGACTGGTGAGTACTCAACCAAGTCATT
CTGAGAATAGTGTATGCGGCGACCGAGTTGCTCTTGCCCGGCGTCAATAC
GGGATAATACCGCGCCACATAGCAGAACTTTAAAAGTGCTCATCATTGGA
AAACGTTCTTCGGGGCGAAAACTCTCAAGGATCTTACCGCTGTTGAGATC
CAGTTCGATGTAACCCACTCGTGCACCCAACTGATCTTCAGCATCTTTTA
CTTTCACCAGCGTTTCTGGGTGAGCAAAAACAGGAAGGCAAAATGCCGCA
AAAAAGGGAATAAGGGCGACACGGAAATGTTGAATACTCATACTCTTCCT
TTTTCAATATTATTGAAGCATTTATCAGGGTTATTGTCTCATGAGCGGAT
ACATATTTGAATGTATTTAGAAAAATAAACAATAGGGGTTCCGCGCACA
TTTCCCCGAAAAGTGCCACCTGATGCGGTGTGAAATACCGCACAGATGCG
TAAGGAGAAAATACCGCATCAGG
```

>pDY (hPGK-IMPDH2(IY)) EF1a EV (SEQ ID NO: 2)
(BOLD: complementary sequence to IMPDH2(IY)
transgene) (SEQ ID NO: 10)

```
AAATTGTAAGCGTTAATATTTTGTTAAAATTCGCGTTAAATTTTTGTTAA
ATCAGCTCATTTTTTAACCAATAGGCCGAAATCGGCAAAATCCCTTATAA
ATCAAAAGAATAGACCGAGATAGGGTTGAGTGTTGTTCCAGTTTGGAACA
AGAGTCCACTATTAAAGAACGTGGACTCCAACGTCAAAGGGCGAAAAACC
GTCTATCAGGGCGATGGCCCACTACGTGAACCATCACCCTAATCAAGTTT
TTTGGGGTCGAGGTGCCGTAAAGCACTAAATCGGAACCCTAAAGGGAGCC
CCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGT
CACGCTGCGCGTAACCACCACACCCGCCGCGCTTAATGCGCCGCTACAGG
GCGCGTCCATTCGCCATTCAGGCTGCGCAACTGTTGGGAAGGGCGATCGG
TGCGGGCCTCTTCGCTATTACGCCAGCTGGCGAAAGGGGGATGTGCTGCA
```

```
AGGCGATTAAGTTGGGTAACGCCAGGGTTTTCCCAGTCACGACGTTGTAA
AACGACGGCCAGTGAATTGTAATACGACTCACTATAGGGCGAATTGGGCC
CGACGTCGCATGCTTGGAAGGGCTAATTCACTCCCAAAGAAGACAAGATA
TCCTTGATCTGTGGATCTACCACACACAAGGCTACTTCCCTGATTAGCAG
AACTACACACCAGGGCCAGGGGTCAGATATCCACTGACCTTTGGATGGTG
CTACAAGCTAGTACCAGTTGAGCCAGATAAGGTAGAAGAGGCCAATAAAG
GAGAGAACACCAGCTTGTTACACCCTGTGAGCCTGCATGGGATGGATGAC
CCGGAGAGAGAAGTGTTAGAGTGGAGGTTTGACAGCCGCCTAGCATTTCA
TCACGTGGCCCGAGAGCTGCATCCGGAGTACTTCAAGAACTGCTGATATC
GAGCTTGCTACAAGGGACTTTCCGCTGGGGACTTTCCAGGGAGGCGTGGC
CTGGGCGGGACTGGGGAGTGGCGAGCCCTCAGATCCTGCATATAAGCAGC
TGCTTTTTGCCTGTACTGGGTCTCTCTGGTTAGACCAGATCTGAGCCTGG
GAGCTCTCTGGCTAACTAGGGAACCCACTGCTTAAGCCTCAATAAAGCTT
GCCTTGAGTGCTTCAAGTAGTGTGTGCCCGTCTGTTGTGTGACTCTGGTA
ACTAGAGATCCCTCAGACCCTTTTAGTCAGTGTGGAAAATCTCTAGCAGT
GGCGCCCGAACAGGGACTTGAAAGCGAAAGGGAAACCAGAGGAGCTCTCT
CGACGCAGGACTCGGCTTGCTGAAGCGCGCACGGCAAGAGGCGAGGGGCG
GCGACTGGTGAGTACGCCAAAAATTTTGACTAGCGGAGGCTAGAAGGAGA
GAGATGGGTGCGAGAGCGTCAGTATTAAGCGGGGAGAATTAGATCGCGA
TGGGAAAAAATTCGGTTAAGGCCAGGGGGAAAGAAAAAATATAAATTAAA
ACATATAGTATGGGCAAGCAGGGAGCTAGAACGATTCGCAGTTAATCCTG
GCCTGTTAGAAACATCAGAAGGCTGTAGACAAATACTGGGACAGCTACAA
CCATCCCTTCAGACAGGATCAGAAGAACTTAGATCATTATATAATACAGT
AGCAACCCTCTATTGTGTGCATCAAAGGATAGAGATAAAAGACACCAAGG
AAGCTTTAGACAAGATAGAGGAAGAGCAAAACAAAAGTAAGACCACCGCA
CAGCAAGCGGCCGCTGATCTTCAGACCTGGAGGAGGAGATATGAGGGACA
ATTGGAGAAGTGAATTATATAAATATAAAGTAGTAAAAATTGAACCATTA
GGAGTAGCACCCACCAAGGCAAAGAGAAGAGTGGTGCAGAGAGAAAAAG
AGCAGTGGGAATAGGAGCTTTGTTCCTTGGGTTCTTGGGAGCAGCAGGAA
GCACTATGGGCGCAGCGTCAATGACGCTGACGGTACAGGCCAGACAATTA
TTGTCTGGTATAGTGCAGCAGCAGAACAATTTGCTGAGGGCTATTGAGGC
GCAACAGCATCTGTTGCAACTCACAGTCTGGGGCATCAAGCAGCTCCAGG
CAAGAATCCTGGCTGTGGAAAGATACCTAAAGGATCAACAGCTCCTGGGG
ATTTGGGGTTGCTCTGGAAAACTCATTTGCACCACTGCTGTGCCTTGGAA
TGCTAGTTGGAGTAATAAATCTCTGGAACAGATTTGGAATCACACGACCT
GGATGGAGTGGGACAGAGAATTAACAATTACACAAGCTTAATACACTCC
TTAATTGAAGAATCGCAAACCAGCAAGAAAAGAATGAACAAGAATTATT
GGAATTAGATAAATGGGCAAGTTTGTGGAATTGGTTTAACATAACAAATT
GGCTGTGGTATATAAAATTATTCATAATGATAGTAGGAGGCTTGGTAGGT
TTAAGAATAGTTTTTGCTGTACTTTCTATAGTGAATAGAGTTAGGCAGGG
ATATTCACCATTATCGTTTCAGACCCACCTCCCAACCCCGAGGGGACCCG
ACAGGCCCGAAGGAATAGAAGAAGAAGGTGGAGAGAGAGACAGAGACAGA
TCCATTCGATTAGTGAACGGATCTCGACGGGATCGATTTTAAAAGAAAAG
GGGGGATTGGGGGGTACAGTGCAGGGGAAAGAATAGTAGACATAATAGCA
ACAGACATACAAACTAAAGAATTACAAAAACAAATTACAAAAATTCAAAA
TTTTATCGATAAGCTTTGCAAAGATGGATAAAGTTTTAAACAGAGAGGAA
TCTTTGCAGCTAATGGACCTTCTAGGTCTGACCCCGTACGCCTCGAGAGA
TCTGATCATAATCAGCCATACCACATTTGTAGAGGTTTTACTTGCTTTAA
AAAACCTCCCACACCTCCCCCTGAACCTGAAACATAAAATGAATGCAATT
GTTGTTGTTAACTTGTTTATTGCAGCTTATAATGGTTACAAATAAGGCAA
TAGCATCACAAATTTCACAAATAAGGCATTTTTTTCACTGCATTCTAGTT
TTGGTTTGTCCAAACTCATCAATGTATCTTATCATGTCTGGATCTCAAAT
CCCTCGGAAGCTGCGCCTGTCTTAGGTTGGAGTGATACATTTTTATCACT
TTTACCCGTCTTTGGATTAGGCAGTAGCTCTGACGGCCCTCCTGTCTTAG
GTTAGTGAAAAATGTCACTCTCTTACCCGTCATTGGCTGTCCAGCTTAGC
TCGCAGGGGAGGTGGTCTGCCTGCAGGTTAGAACAGTCTCTTTTCGTATG
AGTGCAGTGAGTGGACGCCGCCTTCGACCTGGGCTGAAGAAGTTCTTTTC
TCGAACTTCAGTTCGCCGGAATACATCATTGCCCGCACCTGTGTCAGGCT
CTTAGCGCCGATATCCTGGCATGAATGCTGAATTCCGGCGATCAGGTAAG
GCACGAATTTGTGAATACTGCCCTTATCCTGGACAGCTCCAGACACGCCC
TGTGCGACTTTGATCTTGTCTGCCTCGGAAAAATACCTGTTCTGAGAGGA
CAGATGCTTATCCATGGCGTCCAGTGACCCCATGCCCCTATATTTCTTCA
GTCTGAACCCATCACTAAAGAAGTACTCGCCGGGGGCTTCTGTGGTTGCA
GCCAGCAGGCTGCCCATCATCACTGTGCTTGCCCCCAGAGCCAGGGCTTT
TGCGATGTGGCCCACATTCTGAATTCCCCCGTCAGCGATCACTGGGACTC
CGAATCTCCGGGCATACTCGTACACCTTGTAGACAGCAGTTGCCTGAGGT
CGTCCACAGGCCAGCACTTCCTGAATGATGCAGATTGATCCACTCCCCAT
TCCGACCCTCAGAGCATCCACTCCTGCGTCAATCAGGTTTTTGGCCTGGG
CTGCGGTCACGACATTGCCTCCGATGACCTGCAGATTTGGGTACTTGTCC
TTAATGTACTTGATCATATTAATCTGGAAGATGCTGTTTCCCTGGCTTGA
ATCCAGCACGACCACGTCCACCCCTGCCTGAGCCAGCAGATCCAGGCGAT
ATTTATCGTCCTCGTGTGTGCCAATAGCGGCTCCACACAGCAGCTGTTTC
TTTGCGTCCTTACTAGCCAGAGGGTAATCTCGATTTTTCTTCAGGTCGGT
GCGGGCAATGATTGCCACCAGCTCATCGTCTTCATTCACGATAGGCAGTT
TTCCTTTCTTAGACCGCTGCAGAATCTCGTTGGCTTCCTTCAGTGTGATG
CCGGCAGGTGCGACCACCAGATCTTCGCGTTTGGTCATAATCTCTTCCAG
AAAACAGTCATGCTCTTCCTCCTTCAGGAAATCGATGTCTCGACTAGAAA
TGATTCCCACCAGTCGGCTGCCCATTCGTCCAGTATCTGTAATGGGGATG
CCGCAAAATCCGTGCCTAGCTTTGGCCTCGAACACATCGCGGACCCTGTC
CTTGGGCTCAGGACCACTGGGTCGGTGATAAAGCCCTGTTCGTATTTCT
TCACCTTTCTGACCTCATTGGCCTGAAATTCGGAGTGCAGTTATGGTGA
ATGAACCCGATCCCGCCTGTCAGTGCCATAGCAATGGCCATGCCAGCCTC
```

-continued

GGTGACAGTGTCCATAGGGGAGCTCACCAGGGGTGTCTTCAGGGTGATTT

TCTTGGTCAGGGCAGAAGTCAGATCCACCTGGTCTGCGGTAAAATCAATA

TAGCCGGGCAGGATCAGGAAGTCGTTGTAAGTCAGCCCGTCTCCACAATT

AAACAGCTGCTGGGCGGTCAGTCCATCATCAGGGACATAGGAAGTGCCTC

CAGAAATCAGGTAGTCGGCCATGGTGGCGCTAGCCCTGGGGAGAGAGGTC

GGTGATTCGGTCAACGAGGGAGCCGACTGCCGACGTGCGCTCCGGAGGCT

TGCAGAATGCGGAACACCGCGCGGGCAGGAACAGGGCCCACACTACCGCC

CCACACCCCGCCTCCCGCACCGCCCCTTCCCGGCCGCTGCTCTCGGCGCG

CCCCGCTGAGCAGCCGCTATTGGCCACAGCCCATCGCGGTCGGCGCGCTG

CCATTGCTCCCTGGCGCTGTCCGTCTGCGAGGGTACTAGTGAGACGTGCG

GCTTCCGTTTGTCACGTCCGGCACGCCGCGAACCGCAAGGAACCTTCCCG

ACTTAGGGGCGGAGCAGGAAGCGTCGCCGGGGGGCCCACAAGGGTAGCGG

CGAAGATCCGGGTGACGCTGCGAACGGACGTGAAGAATGTGCGAGACCCA

GGGTCGGCGCCGCTGCGTTTCCCGGAACCACGCCCAGAGCAGCCGCGTCC

CTGCGCAAACCCAGGGCTGCCAAGGAAAAGGCGCAACCCCAACCCCGTGG

TTAATTAAGGTGAAAGGAGTGGGAATTGGCTCCGGTGCCCGTCAGTGGGC

AGAGCGCACATCGCCCACAGTCCCCGAGAAGTTGGGGGGAGGGGTCGGCA

ATTGAACCGGTGCCTAGAGAAGGTGGCGCGGGGTAAACTGGGAAAGTGAT

GTCGTGTACTGGCTCCGCCTTTTTCCCGAGGGTGGGGGAGAACCGTATAT

AAGTGCAGTAGTCGCCGTGAACGTTCTTTTTCGCAACGGGTTTGCCGCCA

GAACACAGGTAAGTGCCGTGTGTGGTTCCCGCGGGCCTGGCCTCTTTACG

GGTTATGGCCCTTGCGTGCCTTGAATTACTTCCACCTGGCTGCAGTACGT

GATTCTTGATCCCGAGCTTCGGGTTGGAAGTGGGTGGGAGAGTTCGAGGC

CTTGCGCTTAAGGAGCCCCTTCGCCTCGTGCTTGAGTTGAGGCCTGGCCT

GGGCGCTGGGGCCGCCGCGTGCGAATCTGGTGGCACCTTCGCGCCTGTCT

CGCTGCTTTCGATAAGTCTCTAGCCATTTAAAATTTTTGATGACCTGCTG

CGACGCTTTTTTCTGGCAAGATAGTCTTGTAAATGCGGGCCAAGATCTG

CACACTGGTATTTCGGTTTTTGGGGCCGCGGGCGGCGACGGGCCCGTGC

GTCCCAGCGCACATGTTCGGCGAGGCGGGGCCTGCGAGCGCGGCCACCGA

GAATCGGACGGGGGTAGTCTCAAGCTGGCCGGCCTGCTCTGGTGCCTGGC

CTCGCGCCGCCGTGTATCGCCCCGCCCTGGGCGGCAAGGCTGGCCCGGTC

GGCACCAGTTGCGTGAGCGGAAAGATGGCCGCTTCCCGGCCCTGCTGCAG

GGAGCTCAAAATGGAGGACGCGGCGCTCGGGAGAGCGGGCGGGTGAGTCA

CCCACACAAAGGAAAAGGGCCTTTCCGTCCTCAGCCGTCGCTTCATGTGA

CTCCACGGAGTACCGGGCGCCGTCCAGGCACCTCGATTAGTTCTCGAGCT

TTTGGAGTACGTCGTCTTTAGGTTGGGGGGAGGGGTTTTATGCGATGGAG

TTTCCCCACACTGAGTGGGTGGAGACTGAAGTTAGGCCAGCTTGGCACTT

GATGTAATTCTCCTTGGAATTTGCCCTTTTTGAGTTTGGATCTTGGTTCA

TTCTCAAGCCTCAGACAGTGGTTCAAAGTTTTTTTCTTCCATTTCAGGTG

TCGTGAGGAATTCTGCAGTCGACGGTACCGCGGGCGCGCCCCGGGATCCA

AGCTTCAATTGTGGTCACTCGACAATCAACCTCTGGATTACAAAATTTGT

-continued

GAAAGATTGACTGGTATTCTTAACTATGTTGCTCCTTTTACGCTATGTGG

ATACGCTGCTTTAATGCCTTTGTATCATGCTATTGCTTCCCGTATGGCTT

TCATTTTCTCCTCCTTGTATAAATCCTGGTTGCTGTCTCTTTATGAGGAG

TTGTGGCCCGTTGTCAGGCAACGTGGCGTGGTGTGCACTGTGTTTGCTGA

CGCAACCCCCACTGGTTGGGCATTGCCACCACCTGTCAGCTCCTTTCCG

GGACTTTCGCTTTCCCCCTCCCTATTGCCACGGCGGAACTCATCGCCGCC

TGCCTTGCCCGCTGCTGGACAGGGGCTCGGCTGTTGGGCACTGACAATTC

CGTGGTGTTGTCGGGGAAGCTGACGTCCTTTCCATGGCTGCTCGCCTGTG

TTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCC

TCTTCCGCGTCTTCGCCTTCGCCCTCAGACGAGTCGGATCTCCCTTTGGG

CCGCCTCCCCGCCTGCTCGAGACCTAGAAAAACATGGAGCAATCACAAGT

AGCAATACAGCAGCTACCAATGCTGATTGTGCCTGGCTAGAAGCACAAGA

GGAGGAGGAGGTGGGTTTTCCAGTCACACCTCAGGTACCTTTAAGACCAA

TGACTTACAAGGCAGCTGTAGATCTTAGCCACTTTTTAAAAGAAAAGGGG

GGACTGGAAGGGCTAATTCACTCCCAACGAAGACAAGATCTGCTTTTTGC

TTGTACTGGGTCTCTCTGGTTAGACCAGATCTGAGCCTGGGAGCTCTCTG

GCTAACTAGGGAACCCACTGCTTAAGCCTCAATAAAGCTTGCCTTGAGTG

CTTCAAGTAGTGTGTGCCCGTCTGTTGTGTGACTCTGGTAACTAGAGATC

CCTCAGACCCTTTTAGTCAGTGTGGAAAATCTCTAGCAGTAGTAGTTCAT

GTCATCTTATTATTCAGTATTTATAACTTGCAAAGAAATGAATATCAGAG

AGTGAGAGGACGCGTTGGATGCATAGCTTGAGTATTCTATAGTGTCACCT

AAATAGCTTGGCGTAATCATGGTCATAGCTGTTTCCTGTGTGAAATTGTT

ATCCGCTCACAATTCCACACAACATACGAGCCGGAAGCATAAAGTGTAAA

GCCTGGGGTGCCTAATGAGTGAGCTAACTCACATTAATTGCGTTGCGCTC

ACTGCCCGCTTTCCAGTCGGGAAACCTGTCGTGCCAGCTGCATTAATGAA

TCGGCCAACGCGCGGGGAGAGGCGGTTTGCGTATTGGGCGCTCTTCCGCT

TCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATA

ACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCT

GTTCCGACCCTGCCGCTTACCGGATACCTGTCCGCCTTTCTCCCTTCGGG

AAGCGTGGCGCTTTCTCATAGCTCACGCTGTAGGTATCTCAGTTCGGTGT

AGGTCGTTCGCTCCAAGCTGGGCTGTGTGCACGAACCCCCCGTTCAGCCC

GACCGCTGCGCCTTATCCGGTAACTATCGTCTTGAGTCCAACCCGGTAAG

ACACGACTTATCGCCACTGGCAGCAGCCACTGGTAACAGGATTAGCAGAG

CGAGGTATGTAGGCGGTGCTACAGAGTTCTTGAAGTGGTGGCCTAACTAC

GGCTACACTAGAAGAACAGTATTTGGTATCTGCGCTCTGCTGAAGCCAGT

TACCTTCGGAAAAAGAGTTGGTAGCTCTTGATCCGGCAAACAAACCACCG

-continued

```
CTGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTCA
GTGGAACGAAAACTCACGTTAAGGGATTTTGGTCATGAGATTATCAAAAA
GGATCTTCACCTAGATCCTTTTAAATTAAAAATGAAGTTTTAAATCAATC
TAAAGTATATATGAGTAAACTTGGTCTGACAGTTACCAATGCTTAATCAG
TGAGGCACCTATCTCAGCGATCTGTCTATTTCGTTCATCCATAGTTGCCT
GACTCCCCGTCGTGTAGATAACTACGATACGGGAGGGCTTACCATCTGGC
CCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGA
GTAAGTAGTTCGCCAGTTAATAGTTTGCGCAACGTTGTTGCCATTGCTAC
AGGCATCGTGGTGTCACGCTCGTCGTTTGGTATGGCTTCATTCAGCTCCG
GTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCA
TGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAAT
ACGGGATAATACCGCGCCACATAGCAGAACTTTAAAAGTGCTCATCATTG
GAAAACGTTCTTCGGGGCGAAAACTCTCAAGGATCTTACCGCTGTTGAGA
TCCAGTTCGATGTAACCCACTCGTGCACCCAACTGATCTTCAGCATCTTT
TACTTTCACCAGCGTTTCTGGGTGAGCAAAAACAGGAAGGCAAAATGCCG
CAAAAAAGGGAATAAGGGCGACACGGAAATGTTGAATACTCATACTCTTC
CTTTTTCAATATTATTGAAGCATTTATCAGGGTTATTGTCTCATGAGCGG
ATACATATTTGAATGTATTTAGAAAAATAAACAAATAGGGGTTCCGCGCA
CATTTCCCCGAAAAGTGCCACCTGATGCGGTGTGAAATACCGCACAGATG
CGTAAGGAGAAAATACCGCATCAGG
```

```
>pDY AGA+(IY) (SEQ ID NO: 3)
BOLD: complementary sequence to IMPDH2(IY)
(SEQ ID NO: 10)
Italics: AGA transgene
AAATTGTAAGCGTTAATATTTTGTTAAAATTCGCGTTAAATTTTTGTTAA
ATCAGCTCATTTTTTAACCAATAGGCCGAAATCGGCAAAATCCCTTATAA
ATCAAAAGAATAGACCGAGATAGGGTTGAGTGTTGTTCCAGTTTGGAACA
AGAGTCCACTATTAAAGAACGTGGACTCCAACGTCAAAGGGCGAAAAACC
GTCTATCAGGGCGATGGCCCACTACGTGAACCATCACCCTAATCAAGTTT
TTTGGGGTCGAGGTGCCGTAAAGCACTAAATCGGAACCCTAAAGGGAGCC
CCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGT
CACGCTGCGCGTAACCACCACACCCGCCGCGCTTAATGCGCCGCTACAGG
GCGCGTCCATTCGCCATTCAGGCTGCGCAACTGTTGGGAAGGGCGATCGG
TGCGGGCCTCTTCGCTATTACGCCAGCTGGCGAAAGGGGGATGTGCTGCA
AGGCGATTAAGTTGGGTAACGCCAGGGTTTTCCCAGTCACGACGTTGTAA
AACGACGGCCAGTGAATTGTAATACGACTCACTATAGGGCGAATTGGGCC
```

```
CGACGTCGCATGCTTGGAAGGGCTAATTCACTCCCAAAGAAGACAAGATA
TCCTTGATCTGTGGATCTACCACACACAAGGCTACTTCCCTGATTAGCAG
AACTACACACCAGGGCCAGGGGTCAGATATCCACTGACCTTTGGATGGTG
CTACAAGCTAGTACCAGTTGAGCCAGATAAGGTAGAAGAGGCCAATAAAG
GAGAGAACACCAGCTTGTTACACCCTGTGAGCCTGCATGGGATGGATGAC
CCGGAGAGAGAAGTGTTAGAGTGGAGGTTTGACAGCCGCCTAGCATTTCA
TCACGTGGCCCGAGAGCTGCATCCGGAGTACTTCAAGAACTGCTGATATC
GAGCTTGCTACAAGGGACTTTCCGCTGGGGACTTTCCAGGGAGGCGTGGC
CTGGGCGGGACTGGGGAGTGGCGAGCCCTCAGATCCTGCATATAAGCAGC
TGCTTTTTGCCTGTACTGGGTCTCTCTGGTTAGACCAGATCTGAGCCTGG
GAGCTCTCTGGCTAACTAGGGAACCCACTGCTTAAGCCTCAATAAAGCTT
GCCTTGAGTGCTTCAAGTAGTGTGTGCCCGTCTGTTGTGTGACTCTGGTA
ACTAGAGATCCCTCAGACCCTTTTAGTCAGTGTGGAAAATCTCTAGCAGT
GGCGCCCGAACAGGGACTTGAAAGCGAAAGGGAAACCAGAGGAGCTCTCT
CGACGCAGGACTCGGCTTGCTGAAGCGCGCACGGCAAGAGGCGAGGGGCG
GCGACTGGTGAGTACGCCAAAAATTTTGACTAGCGGAGGCTAGAAGGAGA
GAGATGGGTGCGAGAGCGTCAGTATTAAGCGGGGGAGAATTAGATCGCGA
TGGGAAAAAATTCGGTTAAGGCCAGGGGGAAAGAAAAAATATAAATTAAA
ACATATAGTATGGGCAAGCAGGGAGCTAGAACGATTCGCAGTTAATCCTG
GCCTGTTAGAAACATCAGAAGGCTGTAGACAAATACTGGGACAGCTACAA
CCATCCCTTCAGACAGGATCAGAAGAACTTAGTCATTATATAATACAGT
AGCAACCCTCTATTGTGTGCATCAAAGGATAGAGATAAAAGACACCAAGG
AAGCTTTAGACAAGATAGAGGAAGAGCAAAACAAAAGTAAGACCACCGCA
CAGCAAGCGGCCGCTGATCTTCAGACCTGGAGGAGGAGATATGAGGGACA
ATTGGAGAAGTGAATTATATAAATATAAAGTAGTAAAAATTGAACCATTA
GGAGTAGCACCCACCAAGGCAAAGAGAAGAGTGGTGCAGAGAGAAAAAAG
AGCAGTGGGAATAGGAGCTTTGTTCCTTGGGTTCTTGGGAGCAGCAGGAA
GCACTATGGGCGCAGCGTCAATGACGCTGACGGTACAGGCCAGACAATTA
TTGTCTGGTATAGTGCAGCAGCAGAACAATTTGCTGAGGGCTATTGAGGC
GCAACAGCATCTGTTGCAACTCACAGTCTGGGGCATCAAGCAGCTCCAGG
CAAGAATCCTGGCTGTGGAAAGATACCTAAAGGATCAACAGCTCCTGGGG
ATTTGGGGTTGCTCTGGAAAACTCATTTGCACCACTGCTGTGCCTTGGAA
TGCTAGTTGGAGTAATAAATCTCTGGAACAGATTTGGAATCACACGACCT
GGATGGAGTGGGACAGAGAAATTAACAATTACACAAGCTTAATACACTCC
TTAATTGAAGAATCGCAAAACCAGCAAGAAAAGAATGAACAAGAATTATT
GGAATTAGATAAATGGGCAAGTTTGTGGAATTGGTTTAACATAACAAATT
GGCTGTGGTATATAAAATTATTCATAATGATAGTAGGAGGCTTGGTAGGT
TTAAGAATAGTTTTTGCTGTACTTTCTATAGTGAATAGAGTTAGGCAGGG
ATATTCACCATTATCGTTTCAGACCCACCTCCCAACCCCGAGGGGACCCG
ACAGGCCCGAAGGAATAGAAGAAGAAGGTGGAGAGAGAGACAGAGACAGA
TCCATTCGATTAGTGAACGGATCTCGACGGGATCGATTTTAAAAGAAAG
```

GGGGGATTGGGGGGTACAGTGCAGGGGAAAGAATAGTAGACATAATAGCA
ACAGACATACAAACTAAAGAATTACAAAAACAAATTACAAAAATTCAAAA
TTTTATCGATAAGCTTTGCAAAGATGGATAAAGTTTTAAACAGAGAGGAA
TCTTTGCAGCTAATGGACCTTCTAGGTCTGACCCCGTACGCCTCGAGAGA
TCTGATCATAATCAGCCATACCACATTTGTAGAGGTTTTACTTGCTTTAA
AAAACCTCCCACACCTCCCCCTGAACCTGAAACATAAAATGAATGCAATT
GTTGTTGTTAACTTGTTTATTGCAGCTTATAATGGTTACAAATAAGGCAA
TAGCATCACAAATTTCACAAATAAGGCATTTTTTTCACTGCATTCTAGTT
TTGGTTTGTCCAAACTCATCAATGTATCTTATCATGTCTGGATCTCAAAT
CCCTCGGAAGCTGCGCCTGTCTTAGGTTGGAGTGATACATTTTTATCACT
TTTACCCGTCTTTGGATTAGGCAGTAGCTCTGACGGCCCTCCTGTCTTAG
GTTAGTGAAAAATGTCACTCTCTTACCCGTCATTGGCTGTCCAGCTTAGC
TCGCAGGGGAGGTGGTCTGCCTGCAGGTTAGAACAGTCTCTTTTCGTATG
AGTGCAGTGAGTGGACGCCGCCTTCGACCTGGGCTGAAGAAGTTCTTTTC
TCGAACTTCAGTTCGCCGGAATACATCATTGCCCGCACCTGTGTCAGGCT
CTTAGCGCCGATATCCTGGCATGAATGCTGAATTCCGGCGATCAGGTAAG
GCACGAATTTGTGAATACTGCCCTTATCCTGGACAGCTCCAGACACGCCC
TGTGCGACTTTGATCTTGTCTGCCTCGGAAAAATACCTGTTCTGAGAGGA
CAGATGCTTATCCATGGCGTCCAGTGACCCCATGCCCCTATATTTCTTCA
GTCTGAACCCATCACTAAAGAAGTACTCGCCGGGGGCTTCTGTGGTTGCA
GCCAGCAGGCTGCCCATCATCACTGTGCTTGCCCCCAGAGCCAGGGCTTT
TGCGATGTGGCCCACATTCTGAATTCCCCCGTCAGCGATCACTGGGACTC
CGAATCTCCGGGCATACTCGTACACCTTGTAGACAGCAGTTGCCTGAGGT
CGTCCACAGGCCAGCACTTCCTGAATGATGCAGATTGATCCACTCCCCAT
TCCGACCCTCAGAGCATCCACTCCTGCGTCAATCAGGTTTTTGGCCTGGG
CTGCGGTCACGACATTGCCTCCGATGACCTGCAGATTTGGGTACTTGTCC
TTAATGTACTTGATCATATTAATCTGGAAGATGCTGTTTCCTGGCTTGA
ATCCAGCACGACCACGTCCACCCCTGCCTGAGCCAGCAGATCCAGGCGAT
ATTTATCGTCCTCGTGTGTGCCAATAGCGGCTCCACACAGCAGCTGTTTC
TTTGCGTCCTTACTAGCCAGAGGGTAATCTCGATTTTTCTTCAGGTCGGT
GCGGGCAATGATTGCCACCAGCTCATCGTCTTCATTCACGATAGGCAGTT
TTCCTTTCTTAGACCGCTGCAGAATCTCGTTGGCTTCCTTCAGTGTGATG
CCGGCAGGTGCGACCACCAGATCTTCGCGTTTGGTCATAATCTCTTCCAG
AAAACAGTCATGCTCTTCCTCCTTCAGGAAATCGATGTCTCGACTAGAAA
TGATTCCCACCAGTCGGCTGCCCATTCGTCCAGTATCTGTAATGGGGATG
CCGCAAAATCCGTGCCTAGCTTTGGCCTCGAACACATCGCGGACCCTGTC
CTTGGGGCTCAGGACCACTGGGTCGGTGATAAAGCCCTGTTCGTATTTCT
TCACCTTTCTGACCTCATTGGCCTGAAATTCTGGAGTGCAGTTATGGTGA
ATGAACCCGATCCCGCCTGTCAGTGCCATAGCAATGGCCATGCCAGCCTC
GGTGACAGTGTCCATAGGGGAGCTCACCAGGGGTGTCTTCAGGGTGATTT
TCTTGGTCAGGGCAGAAGTCAGATCCACCTGGTCTGCGGTAAAATCAATA

TAGCCGGGCAGGATCAGGAAGTCGTTGTAAGTCAGCCCGTCTCCACAATT
AAACAGCTGCTGGGCGGTCAGTCCATCATCAGGGACATAGGAAGTGCCTC
CAGAAATCAGGTAGTCGGCCATGGTGGCGCTAGCCCTGGGGAGAGAGGTC
GGTGATTCGGTCAACGAGGGAGCCGACTGCCGACGTGCGCTCCGGAGGCT
TGCAGAATGCGGAACACCGCGCGGGCAGGAACAGGGCCCACACTACCGCC
CCACACCCCGCCTCCCGCACCGCCCCTTCCCGGCCGCTGCTCTCGGCGCG
CCCCGCTGAGCAGCCGCTATTGGCCACAGCCCATCGCGGTCGGCGCGCTG
CCATTGCTCCCTGGCGCTGTCCGTCTGCGAGGGTACTAGTGAGACGTGCG
GCTTCCGTTTGTCACGTCCGGCACGCCGCGAACCGCAAGGAACCTTCCCG
ACTTAGGGGCGGAGCAGGAAGCGTCGCCGGGGGGCCCACAAGGGTAGCGG
CGAAGATCCGGGTGACGCTGCGAACGGACGTGAAGAATGTGCGAGACCCA
GGGTCGGCGCCGCTGCGTTTCCCGGAACCACGCCCAGAGCAGCCGCGTCC
CTGCGCAAACCCAGGGCTGCCAAGGAAAAGGCGCAACCCCAACCCCGTGG
TTAATTAAGGTGAAAGGAGTGGGAATTGGCTCCGGTGCCCGTCAGTGGGC
AGAGCGCACATCGCCCACAGTCCCCGAGAAGTTGGGGGGAGGGGTCGGCA
ATTGAACCGGTGCCTAGAGAAGGTGGCGCGGGGTAAACTGGGAAAGTGAT
GTCGTGTACTGGCTCCGCCTTTTTCCCGAGGGTGGGGGAGAACCGTATAT
AAGTGCAGTAGTCGCCGTGAACGTTCTTTTTCGCAACGGGTTTGCCGCCA
GAACACAGGTAAGTGCCGTGTGTGGTTCCCGCGGGCCTGGCCTCTTTACG
GGTTATGGCCCTTGCGTGCCTTGAATTACTTCCACCTGGCTGCAGTACGT
GATTCTTGATCCCGAGCTTCGGGTTGGAAGTGGGTGGGAGAGTTCGAGGC
CTTGCGCTTAAGGAGCCCCTTCGCCTCGTGCTTGAGTTGAGGCCTGGCCT
GGGCGCTGGGGCCGCCGCGTGCGAATCTGGTGGCACCTTCGCGCCTGTCT
CGCTGCTTTCGATAAGTCTCTAGCCATTTAAAATTTTTGATGACCTGCTG
CGACGCTTTTTTTCTGGCAAGATAGTCTTGTAAATGCGGGCCAAGATCTG
CACACTGGTATTTCGGTTTTTGGGGCGCGGGCGGCGACGGGGCCCGTGC
GTCCCAGCGCACATGTTCGGCGAGGCGGGGCCTGCGAGCGCGGCCACCGA
GAATCGGACGGGGGTAGTCTCAAGCTGGCCGGCCTGCTCTGGTGCCTGGC
CTCGCGCCGCCGTGTATCGCCCCGCCCTGGGCGGCAAGGCTGGCCCGGTC
GGCACCAGTTGCGTGAGCGGAAAGATGGCCGCTTCCCGGCCCTGCTGCAG
GGAGCTCAAAATGGAGGACGCGGCGCTCGGGAGAGCGGGCGGGTGAGTCA
CCCACACAAAGGAAAAGGGCCTTTCCGTCCTCAGCCGTCGCTTCATGTGA
CTCCACGGAGTACCGGGCGCCGTCCAGGCACCTCGATTAGTTCTCGAGCT
TTTGGAGTACGTCGTCTTTAGGTTGGGGGGAGGGGTTTTATGCGATGGAG
TTTCCCCACACTGAGTGGGTGGAGACTGAAGTTAGGCCAGCTTGGCACTT
GATGTAATTCTCCTTGGAATTTGCCCTTTTTGAGTTTGGATCTTGGTTCA
TTCTCAAGCCTCAGACAGTGGTTCAAAGTTTTTTCTTCCATTTCAGGTG
TCGTGAGGAATTCGCCACCATGCAACTTCGAAACCCAGAGCTCCACCTCG
*GATGTGCCCTTGCTCTGAGGTTCCTGGCGCTGGTGTCTTGGGATATACCC*
*GGAGCACGCGCTCTGGACAACGGGCTGGCCCGGACTCCAACCATGGGTTG*
*GCTCCATTGGGAAAGGTTTATGTGCAACTTGGACTGCCAGGAAGAACCCG*

```
ACTCCTGTATTTCCGAGAAACTCTTCATGGAGATGGCCGAGCTGATGGTT
AGCGAAGGCTGGAAGGATGCCGGTTATGAATACTTGTGTATCGACGATTG
TTGGATGGCTCCCCAGCGGGACAGTGAAGGACGACTCCAGGCAGATCCGC
AACGGTTCCCTCATGGCATACGGCAGCTCGCCAATTACGTGCACAGCAAG
GGTTTGAAGCTGGGGATATATGCTGACGTGGGCAACAAAACCTGTGCTGG
TTTCCCCGGCAGCTTCGGCTACTATGATATAGATGCACAAACCTTCGCTG
ATTGGGGCGTGGACCTGCTTAAATTTGACGGCTGTTACTGCGACAGCTTG
GAAAACCTCGCCGATGGATATAAACACATGAGCCTTGCACTCAATCGGAC
TGGCCGGAGCATTGTCTACTCTTGCGAGTGGCCATTGTACATGTGGCCTT
TCCAGAAGCCTAACTATACGGAGATTAGACAGTATTGTAATCACTGGAGA
AACTTTGCAGATATCGACGACTCATGGAAGTCCATCAAATCTATTCTGGA
CTGGACTTCATTCAATCAGGAGCGCATCGTCGATGTTGCCGGTCCAGGTG
GATGGAACGACCCTGACATGCTCGTAATTGGGAATTTCGGACTGTCCTGG
AATCAGCAGGTCACACAGATGGCTTTGTGGGCTATCATGGCAGCCCCACT
CTTTATGTCTAACGATTTGCGGCATATTTCACCACAGGCCAAAGCCCTGC
TGCAAGATAAGGACGTCATAGCGATTAACCAGGACCCACTGGGAAAGCAG
GGCTACCAGCTGAGACAGGGCGACAATTTTGAGGTCTGGGAAAGACCTCT
TAGCGGGCTGGCGTGGGCCGTAGCCATGATTAATCGCCAGGAAATTGGCG
GCCCTCGCTCTTACACTATCGCGGTCGCCAGTCTGGGCAAGGGAGTCGCT
TGTAACCCCGCCTGCTTCATAACTCAGTTGCTGCCCGTGAAACGGAAGCT
GGGCTTCTATGAATGGACTAGCAGACTCCGCAGTCATATTAATCCGACTG
GTACGGTGCTGCTGCAACTGGAGAATACCATGCAGATGTCACTTAAGGAT
CTTCTGTGAGAACCCGGGATCCAAGCTTCAATTGTGGTCACTCGACAATC
AACCTCTGGATTACAAAATTTGTGAAAGATTGACTGGTATTCTTAACTAT
GTTGCTCCTTTTACGCTATGTGGATACGCTGCTTTAATGCCTTTGTATCA
TGCTATTGCTTCCCGTATGGCTTTCATTTTCTCCTCCTTGTATAAATCCT
GGTTGCTGTCTCTTTATGAGGAGTTGTGGCCCGTTGTCAGGCAACGTGGC
GTGGTGTGCACTGTGTTTGCTGACGCAACCCCCACTGGTTGGGGCATTGC
CACCACCTGTCAGCTCCTTTCCGGGACTTTCGCTTTCCCCCTCCCTATTG
CCACGGCGGAACTCATCGCCGCCTGCCTTGCCCGCTGCTGGACAGGGGCT
CGGCTGTTGGGCACTGACAATTCCGTGGTGTTGTCGGGGAAGCTGACGTC
CTTTCCATGGCTGCTCGCCTGTGTTGCCACCTGGATTCTGCGCGGGACGT
CCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCA
GACGAGTCGGATCTCCCTTTGGGCCGCCTCCCCGCCTGCTCGAGACCTAG
AAAAACATGGAGCAATCACAAGTAGCAATACAGCAGCTACCAATGCTGAT
TGTGCCTGGCTAGAAGCACAAGAGGAGGAGGAGGTGGGTTTTCCAGTCAC
ACCTCAGGTACCTTTAAGACCAATGACTTACAAGGCAGCTGTAGATCTTA
GCCACTTTTTAAAAGAAAGGGGGGACTGGAAGGGCTAATTCACTCCCAA
CGAAGACAAGATCTGCTTTTTGCTTGTACTGGGTCTCTCTGGTTAGACCA
GATCTGAGCCTGGGAGCTCTCTGGCTAACTAGGGAACCCACTGCTTAAGC
```

```
CTCAATAAAGCTTGCCTTGAGTGCTTCAAGTAGTGTGTGCCCGTCTGTTG
TGTGACTCTGGTAACTAGAGATCCCTCAGACCCTTTTAGTCAGTGTGGAA
AATCTCTAGCAGTAGTAGTTCATGTCATCTTATTATTCAGTATTTATAAC
TTGCAAAGAAATGAATATCAGAGAGTGAGAGGACGCGTTGGATGCATAGC
TTGAGTATTCTATAGTGTCACCTAAATAGCTTGGCGTAATCATGGTCATA
GCTGTTTCCTGTGTGAAATTGTTATCCGCTCACAATTCCACACAACATAC
GAGCCGGAAGCATAAAGTGTAAAGCCTGGGGTGCCTAATGAGTGAGCTAA
CTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACG
GTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCA
GAGGTGGCGAAACCCGACAGGACTATAAAGATACCAGGCGTTTCCCCCTG
GAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTAT
CGTCTTGAGTCCAACCCGGTAAGACACGACTTATCGCCACTGGCAGCAGC
CACTGGTAACAGGATTAGCAGAGCGAGGTATGTAGGCGGTGCTACAGAGT
TCTTGAAGTGGTGGCCTAACTACGGCTACACTAGAAGAACAGTATTTGGT
ATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAAATT
AAAAATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTACGA
TACGGGAGGGCTTACCATCTGGCCCCAGTGCTGCAATGATACCGCGAGAC
CCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTT
TGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGC
ACTGCATAATTCTCTTACTGTCATGCCATCCGTAAGATGCTTTTCTGTGA
CTGGTGAGTACTCAACCAAGTCATTCTGAGAATAGTGTATGCGGCGACCG
AGTTGCTCTTGCCCGGCGTCAATACGGGATAATACCGCGCCACATAGCAG
```

AACTTTAAAAGTGCTCATCATTGGAAAACGTTCTTCGGGGCGAAAACTCT

CAAGGATCTTACCGCTGTTGAGATCCAGTTCGATGTAACCCACTCGTGCA

CCCAACTGATCTTCAGCATCTTTTACTTTCACCAGCGTTTCTGGGTGAGC

AAAAACAGGAAGGCAAAATGCCGCAAAAAAGGGAATAAGGGCGACACGGA

AATGTTGAATACTCATACTCTTCCTTTTTCAATATTATTGAAGCATTTAT

CAGGGTTATTGTCTCATGAGCGGATACATATTTGAATGTATTTAGAAAAA

TAAACAAATAGGGGTTCCGCGCACATTTCCCCGAAAAGTGCCACCTGATG

CGGTGTGAAATACCGCACAGATGCGTAAGGAGAAAATACCGCATCAGG

Plasmid expressing GBA+IY (SEQ ID NO: 4)
Italics: co:hGBA transgene
BOLD: reverse complement of IMPDH2(IY) transgene
(SEQ ID NO: 10)
CCGGTGCCTAGAGAAGGTGGCGCGGGGTAAACTGGGAAAGTGATGTCGTG

TACTGGCTCCGCCTTTTTCCCGAGGGTGGGGGAGAACCGTATATAAGTGC

AGTAGTCGCCGTGAACGTTCTTTTTCGCAACGGGTTTGCCGCCAGAACAC

AGGTAAGTGCCGTGTGTGGTTCCCGCGGGCCTGGCCTCTTTACGGGTTAT

GGCCCTTGCGTGCCTTGAATTACTTCCACCTGGCTGCAGTACGTGATTCT

TGATCCCGAGCTTCGGGTTGGAAGTGGGTGGGAGAGTTCGAGGCCTTGCG

CTTAAGGAGCCCCTTCGCCTCGTGCTTGAGTTGAGGCCTGGCCTGGGCGC

TGGGGCCGCCGCGTGCGAATCTGGTGGCACCTTCGCGCCTGTCTCGCTGC

TTTCGATAAGTCTCTAGCCATTTAAAATTTTTGATGACCTGCTGCGACGC

TTTTTTTTCTGGCAAGATAGTCTTGTAAATGCGGGCCAAGATCTGCACACT

GGTATTTCGGTTTTTGGGGCCGCGGGCGGCGACGGGGCCCGTGCGTCCCA

GCGCACATGTTCGGCGAGGCGGGGCCTGCGAGCGCGGCCACCGAGAATCG

GACGGGGGTAGTCTCAAGCTGGCCGGCCTGCTCTGGTGCCTGGCCTCGCG

CCGCCGTGTATCGCCCCGCCCTGGGCGGCAAGGCTGGCCCGGTCGGCACC

AGTTGCGTGAGCGGAAAGATGGCCGCTTCCCGGCCCTGCTGCAGGGAGCT

CAAAATGGAGGACGCGGCGCTCGGGAGAGCGGGCGGGTGAGTCACCCACA

CAAAGGAAAAGGGCCTTTCCGTCCTCAGCCGTCGCTTCATGTGACTCCAC

GGAGTACCGGGCGCCGTCCAGGCACCTCGATTAGTTCTCGAGCTTTTGGA

GTACGTCGTCTTTAGGTTGGGGGGAGGGGTTTTATGCGATGGAGTTTCCC

CACACTGAGTGGGTGGAGACTGAAGTTAGGCCAGCTTGGCACTTGATGTA

ATTCTCTTGGAATTTGCCCTTTTTGAGTTTGGATCTTGGTTCATTCTCA

AGCCTCAGACAGTGGTTCAAAGTTTTTTTCTTCCATTTCAGGTGTCGTGA

GGAATTCGCTAGCGCCACCATGGAGTTCTCAAGCCCCTCTCGGGAAGAAT

*GCCCAAAACCTCTGTCACGGGTGTCTATCATGGCTGGATCACTGACTGGC*

*CTGCTGCTGCTGCAGGCCGTGAGCTGGGCCTCCGGAGCCCGGCCTTGCAT*

*CCCAAAGTCTTTCGGCTACAGCTCCGTGGTGTGCGTGTGCAACGCCACCT*

*ATTGTGACTCCTTCGATCCCCTACCTTTCCCGCCCTGGGCACATTTTCT*

*CGGTACGAGTCTACACGCAGCGGCAGGAGAATGGAGCTGAGCATGGGCC*

*TATCCAGGCCAATCACACCGGAACAGGCCTGCTGCTGACCCTGCAGCCAG*

*AGCAGAAGTTCCAGAAGGTGAAGGGCTTTGGAGGAGCAATGACAGACGCA*

*GCCGCCCTGAACATCCTGGCCCTGTCCCCACCCGCCCAGAATCTGCTGCT*

*GAAGTCCTACTTCTCTGAGGAGGGCATCGGCTATAACATCATCAGGGTGC*

*CCATGGCCAGCTGCGACTTTTCCATCAGAACCTACACATATGCCGATACC*

*CCTGACGATTTCCAGCTGCACAATTTTTCCCTGCCAGAGGAGGATACAAA*

*GCTGAAGATCCCACTGATCCACAGGGCCCTGCAGCTGGCCCAGAGGCCCG*

*TGAGCCTGCTGGCCAGCCCCTGGACCTCCCCTACATGGCTGAAGACCAAC*

*GGCGCCGTGAATGGCAAGGGCTCTCTGAAGGGACAGCCAGGCGACATCTA*

*CCACCAGACATGGGCCCGCTATTTCGTGAAGTTTCTGGATGCCTACGCCG*

*AGCACAAGCTGCAGTTCTGGGCCGTGACCGCAGAGAACGAGCCTTCTGCC*

*GGCCTGCTGAGCGGCTATCCCTTCCAGTGCCTGGGCTTTACACCTGAGCA*

*CCAGAGGGACTTTATCGCCAGAGATCTGGGCCCAACCCTGGCCAACTCCA*

*CACACCACAATGTGCGGCTGCTGATGCTGGACGATCAGCGCCTGCTGCTG*

*CCTCACTGGGCCAAGGTGGTGCTGACCGACCCAGAGGCCGCCAAGTACGT*

*GCACGGCATCGCCGTGCACTGGTATCTGGATTTCCTGGCACCAGCAAAGG*

*CCACCCTGGGAGAGACACACAGGCTGTTCCCTAACACCATGCTGTTTGCC*

*AGCGAGGCCTGCGTGGGCTCCAAGTTTTGGGAGCAGTCCGTGCGGCTGGG*

*CTCTTGGGACAGGGGCATGCAGTACTCCCACTCTATCATCACCAATCTGC*

*TGTATCACGTGGTGGGCTGGACAGACTGGAACCTGGCCCTGAATCCAGAG*

*GGCGGCCCCAACTGGGTGAGAAATTTCGTGGATAGCCCCATCATCGTGGA*

*CATCACCAAGGATACATTCTACAAGCAGCCAATGTTTTATCACCTGGGCC*

*ACTTCTCTAAGTTTATCCCAGAGGGCAGCCAGAGGGTGGGCCTGGTGGCC*

*AGCCAGAAGAACGACCTGGATGCAGTGGCCCTGATGCACCCTGACGGCTC*

*CGCCGTGGTGGTGGTGCTGAATCGCTCTAGCAAGGACGTGCCTCTGACCA*

*TCAAGGACCCCGCCGTGGGCTTTCTGGAGACCATTTCACCCGGCTATTCT*

*ATTCATACCTATCTGTGGAGGAGGCAGTAACCTGCAGGGGATCCAAGCTT*

CAATTGTGGTCACTCGACAATCAACCTCTGGATTACAAAATTTGTGAAAG

ATTGACTGGTATTCTTAACTATGTTGCTCCTTTTACGCTATGTGGATACG

CTGCTTTAATGCCTTTGTATCATGCTATTGCTTCCCGTATGGCTTTCATT

TTCTCCTCCTTGTATAAATCCTGGTTGCTGTCTCTTTATGAGGAGTTGTG

GCCCGTTGTCAGGCAACGTGGCGTGGTGTGCACTGTGTTTGCTGACGCAA

CCCCCACTGGTTGGGGCATTGCCACCACCTGTCAGCTCCTTTCCGGGACT

TTCGCTTTCCCCCTCCCTATTGCCACGGCGGAACTCATCGCCGCCTGCCT

TGCCCGCTGCTGGACAGGGGCTCGGCTGTTGGGCACTGACAATTCCGTGG

TGTTGTCGGGGAAGCTGACGTCCTTTCCATGGCTGCTCGCCTGTGTTGCC

ACCTGGATTCTGCGCGGGACGTCCTTCTGCTACGTCCCTTCGGCCCTCAA

TCCAGCGGACCTTCCTTCCCGCGGCCTGCTGCCGGCTCTGCGGCCTCTTC

CGCGTCTTCGCCTTCGCCCTCAGACGAGTCGGATCTCCCTTTGGGCCGCC

TCCCCGCCTGCTCGAGACCTAGAAAAACATGGAGCAATCACAAGTAGCAA

TACAGCAGCTACCAATGCTGATTGTGCCTGGCTAGAAGCACAAGAGGAGG

AGGAGGTGGGTTTTCCAGTCACACCTCAGGTACCTTTAAGACCAATGACT

TACAAGGCAGCTGTAGATCTTAGCCACTTTTTAAAAGAAAAGGGGGGACT

GGAAGGGCTAATTCACTCCCAACGAAGACAAGATCTGCTTTTTGCTTGTA

-continued

CTGGGTCTCTCTGGTTAGACCAGATCTGAGCCTGGGAGCTCTCTGGCTAA
CTAGGGAACCCACTGCTTAAGCCTCAATAAAGCTTGCCTTGAGTGCTTCA
AGTAGTGTGTGCCCGTCTGTTGTGTGACTCTGGTAACTAGAGATCCCTCA
GACCCTTTTAGTCAGTGTGGAAAATCTCTAGCAGTAGTAGTTCATGTCAT
CTTATTATTCAGTATTTATAACTTGCAAAGAAATGAATATCAGAGAGTGA
GAGGACGCGTTGGATGCATAGCTTGAGTATTCTATAGTGTCACCTAAATA
GCTTGGCGTAATCATGGTCATAGCTGTTTCCTGTGTGAAATTGTTATCCG
CTCACAATTCCACACAACATACGAGCCGGAAGCATAAAGTGTAAAGCCTG
GGGTGCCTAATGAGTGAGCTAACTCACATTAATTGCGTTGCGCTCACTGC
CCGCTTTCCAGTCGGGAAACCTGTCGTGCCAGCTGCATTAATGAATCGGC
CAACGCGCGGGGAGAGGCGGTTTGCGTATTGGGCGCTCTTCCGCTTCCTC
GCTCACTGACTCGCTGCGCTCGGTCGTTCGGCTGCGGCGAGCGGTATCAG
CTCACTCAAAGGCGGTAATACGGTTATCCACAGAATCAGGGGATAACGCA
GGAAAGAACATGTGAGCAAAAGGCCAGCAAAAGGCCAGGAACCGTAAAAA
GGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACG
ACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCT
TCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGG
ATCTCAAGAAGATCCTTTGATCTTTTCTACGGGGTCTGACGCTCAGTGGA
ACGAAAACTCACGTTAAGGGATTTTGGTCATGAGATTATCAAAAAGGATC
TTCACCTAGATCCTTTTAAATTAAAAATGAAGTTTTAAATCAATCTAAAG
TATATATGAGTAAACTTGGTCTGACAGTTACCAATGCTTAATCAGTGAGG
CACCTATCTCAGCGATCTGTCTATTTCGTTCATCCATAGTTGCCTGACTC
CCCGTCGTGTAGATAACTACGATACGGGAGGGCTTACCATCTGGCCCCAG
TGCTGCAATGATACCGCGAGACCCACGCTCACCGGCTCCAGATTTATCAG
CAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGT
TATCACTCATGGTTATGGCAGCACTGCATAATTCTCTTACTGTCATGCCA
TCCGTAAGATGCTTTTCTGTGACTGGTGAGTACTCAACCAAGTCATTCTG

-continued

AGAATAGTGTATGCGGCGACCGAGTTGCTCTTGCCCGGCGTCAATACGGG
ATAATACCGCGCCACATAGCAGAACTTTAAAAGTGCTCATCATTGGAAAA
CGTTCTTCGGGGCGAAAACTCTCAAGGATCTTACCGCTGTTGAGATCCAG
TTCGATGTAACCCACTCGTGCACCCAACTGATCTTCAGCATCTTTTACTT
TCACCAGCGTTTCTGGGTGAGCAAAAACAGGAAGGCAAAATGCCGCAAAA
AAGGGAATAAGGGCGACACGGAAATGTTGAATACTCATACTCTTCCTTTT
TCAATATTATTGAAGCATTTATCAGGGTTATTGTCTCATGAGCGGATACA
TATTTGAATGTATTTAGAAAAATAAACAAATAGGGGTTCCGCGCACATTT
CCCCGAAAAGTGCCACCTGATGCGGTGTGAAATACCGCACAGATGCGTAA
GGAGAAAATACCGCATCAGGAAATTGTAAGCGTTAATATTTTGTTAAAAT
TCGCGTTAAATTTTTGTTAAATCAGCTCATTTTTTAACCAATAGGCCGAA
ATCGGCAAAATCCCTTATAAATCAAAAGAATAGACCGAGATAGGGTTGAG
TGTTGTTCCAGTTTGGAACAAGAGTCCACTATTAAAGAACGTGGACTCCA
ACGTCAAAGGGCGAAAAACCGTCTATCAGGGCGATGGCCCACTACGTGAA
CCATCACCCTAATCAAGTTTTTTGGGGTCGAGGTGCCGTAAAGCACTAAA
TCGGAACCCTAAAGGGAGCCCCCGATTTAGAGCTTGACGGGGAAAGCCGG
CGAACGTGGCGAGAAAGGAAGGGAAGAAAGCGAAAGGAGCGGGCGCTAGG
GCGCTGGCAAGTGTAGCGGTCACGCTGCGCGTAACCACCACACCCGCCGC
GCTTAATGCGCCGCTACAGGGCGCGTCCATTCGCCATTCAGGCTGCGCAA
CTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTT
TCCCAGTCACGACGTTGTAAAACGACGGCCAGTGAATTGTAATACGACTC
ACTATAGGGCGAATTGGGCCCGACGTCGCATGCTTGGAAGGGCTAATTCA
CTCCCAAAGAAGACAAGATATCCTTGATCTGTGGATCTACCACACACAAG
GCTACTTCCCTGATTAGCAGAACTACACACCAGGGCCAGGGGTCAGATAT
CCACTGACCTTTGGATGGTGCTACAAGCTAGTACCAGTTGAGCCAGATAA
GGTAGAAGAGGCCAATAAAGGAGAGAACACCAGCTTGTTACACCCTGTGA
GCCTGCATGGGATGGATGACCCGGAGAGAGAAGTGTTAGAGTGGAGGTTT
GACAGCCGCCTAGCATTTCATCACGTGGCCCGAGAGCTGCATCCGGAGTA
CTTCAAGAACTGCTGATATCGAGCTTGCTACAAGGGACTTTCCGCTGGGG
ACTTTCCAGGGAGGCGTGGCCTGGGCGGGACTGGGGAGTGGCGAGCCCTC
AGATCCTGCATATAAGCAGCTGCTTTTTGCCTGTACTGGGTCTCTCTGGT
TAGACCAGATCTGAGCCTGGGAGCTCTCTGGCTAACTAGGGAACCCACTG
CTTAAGCCTCAATAAAGCTTGCCTTGAGTGCTTCAAGTAGTGTGTGCCCG
TCTGTTGTGTGACTCTGGTAACTAGAGATCCCTCAGACCCTTTTAGTCAG
TGTGGAAAATCTCTAGCAGTGGCGCCCGAACAGGGACTTGAAAGCGAAAG
GAAACCAGAGGAGCTCTCTCGACGCAGGACTCGGCTTGCTGAAGCGCGC
ACGGCAAGAGGCGAGGGGCGGCGACTGGTGAGTACGCCAAAATTTTGAC
TAGCGGAGGCTAGAAGGAGAGAGATGGGTGCGAGAGCGTCAGTATTAAGC
GGGGGAGAATTAGATCGCGATGGGAAAAAATTCGGTTAAGGCCAGGGGGA
AAGAAAAAATATAAATTAAAACATATAGTATGGGCAAGCAGGGAGCTAGA

-continued

ACGATTCGCAGTTAATCCTGGCCTGTTAGAAACATCAGAAGGCTGTAGAC
AAATACTGGGACAGCTACAACCATCCCTTCAGACAGGATCAGAAGAACTT
AGATCATTATATAATACAGTAGCAACCCTCTATTGTGTGCATCAAAGGAT
AGAGATAAAAGACACCAAGGAAGCTTTAGACAAGATAGAGGAAGAGCAAA
ACAAAAGTAAGACCACCGCACAGCAAGCGGCCGCTGATCTTCAGACCTGG
AGGAGGAGATATGAGGGACAATTGGAGAAGTGAATTATATAAATATAAAG
TAGTAAAAATTGAACCATTAGGAGTAGCACCCACCAAGGCAAAGAGAAGA
GTGGTGCAGAGAGAAAAAGAGCAGTGGGAATAGGAGCTTTGTTCCTTGG
GTTCTTGGGAGCAGCAGGAAGCACTATGGGCGCAGCGTCAATGACGCTGA
CGGTACAGGCCAGACAATTATTGTCTGGTATAGTGCAGCAGCAGAACAAT
TTGCTGAGGGCTATTGAGGCGCAACAGCATCTGTTGCAACTCACAGTCTG
GGGCATCAAGCAGCTCCAGGCAAGAATCCTGGCTGTGGAAAGATACCTAA
AGGATCAACAGCTCCTGGGGATTTGGGGTTGCTCTGGAAAACTCATTTGC
ACCACTGCTGTGCCTTGGAATGCTAGTTGGAGTAATAAATCTCTGGAACA
GATTTGGAATCACACGACCTGGATGGAGTGGGACAGAGAAATTAACAATT
ACACAAGCTTAATACACTCCTTAATTGAAGAATCGCAAAACCAGCAAGAA
AAGAATGAACAAGAATTATTGGAATTAGATAAATGGGCAAGTTTGTGGAA
TTGGTTTAACATAACAAATTGGCTGTGGTATATAAAATTATTCATAATGA
TAGTAGGAGGCTTGGTAGGTTTAAGAATAGTTTTTGCTGTACTTTCTATA
GTGAATAGAGTTAGGCAGGGATATTCACCATTATCGTTTCAGACCCACCT
CCCAACCCCGAGGGGACCCGACAGGCCCGAAGGAATAGAAGAAGAAGGTG
GAGAGAGAGACAGAGACAGATCCATTCGATTAGTGAACGGATCTCGACGG
GATCGATTTTAAAAGAAAAGGGGGGATTGGGGGGTACAGTGCAGGGGAAA
GAATAGTAGACATAATAGCAACAGACATACAAACTAAAGAATTACAAAAA
CAAATTACAAAAATTCAAAATTTTATCGATAAGCTTTGCAAAGATGGATA
AAGTTTTAAACAGAGAGGAATCTTTGCAGCTAATGGACCTTCTAGGTCTG
ACCCCGTACGCCTGAGAGATCTGATCATAATCAGCCATACCACATTTGT
AGAGGTTTTACTTGCTTTAAAAAACCTCCCACACCTCCCCCTGAACCTGA
AACATAAAATGAATGCAATTGTTGTTGTTAACTTGTTTATTGCAGCTTAT
AATGGTTACAAATAAGGCAATAGCATCACAAATTTCACAAATAAGGCATT
TTTTTCACTGCATTCTAGTTTTGGTTTGTCCAAACTCATCAATGTATCTT
ATCATGTCTGGATCTCAAATCCCTCGGAAGCTGCGCCTGTCTTAGGTTGG
AGTGATACATTTTTATCACTTTTACCCGTCTTTGGATTAGGCAGTAGCTC
TGACGGCCCTCCTGTCTTAGGTTAGTGAAAAATGTCACTCTCTTACCCGT
CATTGGCTGTCCAGCTTAGCTCGCAGGGGAGGTGGTCTGCCTGCAGG**TTA
GAACAGTCTCTTTTCGTATGAGTGCAGTGAGTGGACGCCGCCTTCGACCT
GGGCTGAAGAAGTTCTTTTCTCGAACTTCAGTTCGCGGAATACATCATT
GCCCGCACCTGTGTCAGGCTCTTAGCGCCGATATCCTGGCATGAATGCTG
AATTCCGGCGATCAGGTAAGGCACGAAATTTGTGAATACTGCCCTTATCCT
GGACAGCTCCAGACACGCCCTGTGCGACTTTGATCTTGTCTGCCTCGGAA
AAATACCTGTTCTGAGAGGACAGATGCTTATCCATGGCGTCCAGTGACCC**

**CATGCCCCTATATTTCTTCAGTCTGAACCCATCACTAAAGAAGTACTCGC
CGGGGGCTTCTGTGGTTGCAGCCAGCAGGCTGCCCATCATCACTGTGCTT
GCCCCCAGAGCCAGGGCTTTTGCGATGTGGCCCACATTCTGAATTCCCCC
GTCAGCGATCACTGGGACTCCGAATCTCCGGGCATACTCGTACACCTTGT
AGACAGCAGTTGCCTGAGGTCGTCCACAGGCCAGCACTTCCTGAATGATG
CAGATTGATCCACTCCCCATTCCGACCCTCAGAGCATCCACTCCTGCGTC
AATCAGGTTTTTGGCCTGGGCTGCGGTCACGACATTGCCTCCGATGACCT
GCAGATTTGGGTACTTGTCCTTAATGTACTTGATCATATTAATCTGGAAG
ATGCTGTTTCCCTGGCTTGAATCCAGCACGACCACGTCCACCCCTGCCTG
AGCCAGCAGATCCAGGCGATATTTATCGTCCTCGTGTGTGCCAATAGCGG
CTCCACACAGCAGCTGTTTCTTTGCGTCCTTACTAGCCAGAGGGTAATCT
CGATTTTTCTTCAGGTCGGTGCGGGCAATGATTGCCACCAGCTCATCGTC
TTCATTCACGATAGGCAGTTTTCCTTTCTTAGACCGCTGCAGAATCTCGT
TGGCTTCCTTCAGTGTGATGCCGGCAGGTGCGACCACCAGATCTTCGCGT
TTGGTCATAATCTCTTCCAGAAAACAGTCATGCTCTTCCTCCTTCAGGAA
ATCGATGTCTCGACTAGAAATGATTCCCACCAGTCGGCTGCCCATTCGTC
CAGTATCTGTAATGGGGATGCCGCAAAATCCGTGCCTAGCTTTGGCCTCG
AACACATCGCGGACCCTGTCCTTGGGGCTCAGGACCACTGGGTCGGTGAT
AAAGCCCTGTTCGTATTTCTTCACCTTTCTGACCTCATTGGCCTGAAATT
CTGGAGTGCAGTTATGGTGAATGAACCCGATCCCGCCTGTCAGTGCCATA
GCAATGGCCATGCCAGCCTCGGTGACAGTGTCCATAGGGGAGCTCACCAG
GGGTGTCTTCAGGGTGATTTTCTTGGTCAGGGCAGAAGTCAGATCCACCT
GGTCTGCGGTAAAATCAATATAGCCGGGCAGGATCAGGAAGTCGTTGTAA
GTCAGCCCGTCTCCACAATTAAACAGCTGCTGGGCGGTCAGTCCATCATC
AGGGACATAGGAAGTGCCTCCAGAAATCAGGTAGTCGGCCATGGTGGCGC
TAGCCCTGGGGAGAGAGGTCGGTGATTCGGTCAACGAGGGAGCCGACTGC
CGACGTGCGCTCCGGAGGCTTGCAGAATGCGGAACACCGCGCGGGCAGGA
ACAGGGCCCACACTACCGCCCCACACCCCGCCTCCCGCACCGCCCCTTCC
CGGCCGCTGCTCTCGGCGCGCCCCGCTGAGCAGCCGCTATTGGCCACAGC
CCATCGCGGTCGGCGCGCTGCCATTGCTCCCTGGCGCTGTCCGTCTGCGA
GGGTACTAGTGAGACGTGCGGCTTCCGTTTGTCACGTCCGGCACGCCGCG
AACCGCAAGGAACCTTCCCGACTTAGGGGCGGAGCAGGAAGCGTCGCCGG
GGGGCCCACAAGGGTAGCGGCGAAGATCCGGGTGACGCTGCGAACGGACG
TGAAGAATGTGCGAGACCCAGGGTCGGCGCCGCTGCGTTTCCCGGAACCA
CGCCCAGAGCAGCCGCGTCCCTGCGCAAACCCAGGGCTGCCAAGGAAAAG
GCGCAACCCCAACCCCGTGGTTAATTAAGGTGAAAGGAGTGGGAATTGGC
TCCGGTGCCCGTCAGTGGGCAGAGCGCACATCGCCCACAGTCCCCGAGAA
GTTGGGGGGAGGGGTCGGCAATTGAA**

SEQ ID NO: 5: codon optimized AGA
>co.hAGA
ATGCAACTTCGAAACCCAGAGCTCCACCTCGGATGTGCCCTTGCTCTGAG
GTTCCTGGCGCTGGTGTCTTGGGATATACCCGGAGCACGCGCTCTGGACA -continued ACGGGCTGGCCCGGACTCCAACCATGGGTTGGCTCCATTGGGAAAGGTTT
ATGTGCAACTTGGACTGCCAGGAAGAACCCGACTCCTGTATTTCCGAGAA
ACTCTTCATGGAGATGGCCGAGCTGATGGTTAGCGAAGGCTGGAAGGATG
CCGGTTATGAATACTTGTGTATCGACGATTGTTGGATGGCTCCCCAGCGG
GACAGTGAAGGACGACTCCAGGCAGATCCGCAACGGTTCCCTCATGGCAT
ACGGCAGCTCGCCAATTACGTGCACAGCAAGGGTTTGAAGCTGGGGATAT
ATGCTGACGTGGGCAACAAAACCTGTGCTGGTTTCCCCGGCAGCTTCGGC
TACTATGATATAGATGCACAAACCTTCGCTGATTGGGGCGTGGACCTGCT
TAAAATTTGACGGCTGTTACTGCGACAGCTTGGAAAACCTCGCCGATGGAT
ATAAACACATGAGCCTTGCACTCAATCGGACTGGCCGGAGCATTGTCTAC
TCTTGCGAGTGGCCATTGTACATGTGGCCTTTCCAGAAGCCTAACTATAC
GGAGATTAGACAGTATTGTAATCACTGGAGAAACTTTGCAGATATCGACG
ACTCATGGAAGTCCATCAAATCTATTCTGGACTGGACTTCATTCAATCAG
GAGCGCATCGTCGATGTTGCCGGTCCAGGTGGATGGAACGACCCTGACAT
GCTCGTAATTGGGAATTTCGGACTGTCCTGGAATCAGCAGGTCACACAGA
TGGCTTTGTGGGCTATCATGGCAGCCCCACTCTTTATGTCTAACGATTTG
CGGCATATTTCACCACAGGCCAAAGCCCTGCTGCAAGATAAGGACGTCAT
AGCGATTAACCAGGACCCACTGGGAAAGCAGGGCTACCAGCTGAGACAGG
GCGACAATTTTGAGGTCTGGGAAAGACCTCTTAGCGGGCTGGCGTGGGCC
GTAGCCATGATTAATCGCCAGGAAATTGGCGGCCCTCGCTCTTACACTAT
CGCGGTCGCCAGTCTGGGCAAGGGAGTCGCTTGTAACCCCGCCTGCTTCA
TAACTCAGTTGCTGCCCGTGAAACGGAAGCTGGGCTTCTATGAATGGACT
AGCAGACTCCGCAGTCATATTAATCCGACTGGTACGGTGCTGCTGCAACT
GGAGAATACCATGCAGATGTCACTTAAGGATCTTCTGTGA SEQ ID NO: 6, GBA transgene
>co.hGBA
ATGGAGTTCTCAAGCCCCTCTCGGGAAGAATGCCCAAAACCTCTGTCACG
GGTGTCTATCATGGCTGGATCACTGACTGGCCTGCTGCTGCTGCAGGCCG
TGAGCTGGGCCTCCGGAGCCCGGCCTTGCATCCCAAAGTCTTTCGGCTAC
AGCTCCGTGGTGTGCGTGTGCAACGCCACCTATTGTGACTCCTTCGATCC
CCCTACCTTTCCCGCCCTGGGCACATTTTCTCGGTACGAGTCTACACGCA
GCGGCAGGAGAATGGAGCTGAGCATGGGCCCTATCCAGGCCAATCACACC
GGAACAGGCCTGCTGCTGACCCTGCAGCCAGAGCAGAAGTTCCAGAAGGT
GAAGGGCTTTGGAGGAGCAATGACAGACGCAGCCGCCCTGAACATCCTGG
CCCTGTCCCCACCCGCCCAGAATCTGCTGCTGAAGTCCTACTTCTCTGAG
GAGGGCATCGGCTATAACATCATCAGGGTGCCCATGGCCAGCTGCGACTT
TTCCATCAGAACCTACACATATGCCGATACCCCTGACGATTTCCAGCTGC
ACAATTTTTCCCTGCCAGAGGAGGATACAAAGCTGAAGATCCCACTGATC
CACAGGGCCCTGCAGCTGGCCCAGAGGCCCGTGAGCCTGCTGGCCAGCCC
CTGGACCTCCCCTACATGGCTGAAGACCAACGGCGCCGTGAATGGCAAGG
GCTCTCTGAAGGGACAGCCAGGCGACATCTACCACCAGACATGGGCCCGC
TATTTCGTGAAGTTTCTGGATGCCTACGCCGAGCACAAGCTGCAGTTCTG -continued GGCCGTGACCGCAGAGAACGAGCCTTCTGCCGGCCTGCTGAGCGGCTATC
CCTTCCAGTGCCTGGGCTTTACACCTGAGCACCAGAGGGACTTTATCGCC
AGAGATCTGGGCCCAACCCTGGCCAACTCCACACACCACAATGTGCGGCT
GCTGATGCTGGACGATCAGCGCCTGCTGCTGCCTCACTGGGCCAAGGTGG
TGCTGACCGACCCAGAGGCCGCCAAGTACGTGCACGGCATCGCCGTGCAC
TGGTATCTGGATTTCCTGGCACCAGCAAAGGCCACCCTGGGAGAGACACA
CAGGCTGTTCCCTAACACCATGCTGTTTGCCAGCGAGGCCTGCGTGGGCT
CCAAGTTTTGGGAGCAGTCCGTGCGGCTGGGCTCTTGGGACAGGGGCATG
CAGTACTCCCACTCTATCATCACCAATCTGCTGTATCACGTGGTGGGCTG
GACAGACTGGAACCTGGCCCTGAATCCAGAGGGCGGCCCCAACTGGGTGA
GAAATTTCGTGGATAGCCCCATCATCGTGGACATCACCAAGGATACATTC
TACAAGCAGCCAATGTTTTATCACCTGGGCCACTTCTCTAAGTTTATCCC
AGAGGGCAGCCAGAGGGTGGGCCTGGTGGCCAGCCAGAAGAACGACCTGG
ATGCAGTGGCCCTGATGCACCCTGACGGCTCCGCCGTGGTGGTGGTGCTG
AATCGCTCTAGCAAGGACGTGCCTCTGACCATCAAGGACCCCGCCGTGGG
CTTTCTGGAGACCATTTCACCCGGCTATTCTATTCATACCTATCTGTGGA
GGAGGCAGTAA SEQ ID NO: 7: coIMPDH2(IY) transgene
ATGGCCGACTACCTGATTTCTGGAGGCACTTCCTATGTCCCTGATGATGG
ACTGACCGCCCAGCAGCTGTTTAATTGTGGAGACGGGCTGACTTACAACG
ACTTCCTGATCCTGCCCGGCTATATTGATTTTACCGCAGACCAGGTGGAT
CTGACTTCTGCCCTGACCAAGAAAATCACCCTGAAGACACCCCTGGTGAG
CTCCCCTATGGACACTGTCACCGAGGCTGGCATGGCCATTGCTATGGCAC
TGACAGGCGGGATCGGGTTCATTCACCATAACTGCACTCCAGAATTTCAG
GCCAATGAGGTCAGAAAGGTGAAGAAATACGAACAGGGCTTTATCACCGA
CCCAGTGGTCCTGAGCCCCAAGGACAGGGTCCGCGATGTGTTCGAGGCCA
AGCTAGGCACGGATTTTGCGGCATCCCCATTACAGATACTGGACGAATG
GGCAGCCGACTGGTGGGAATCATTTCTAGTCGAGACATCGATTTCCTGAA
GGAGGAAGAGCATGACTGTTTTCTGGAAGAGATTATGACCAAACGCGAAG
ATCTGGTGGTCGCACCTGCCGGCATCACACTGAAGGAAGCCAACGAGATT
CTGCAGCGGTCTAAGAAAGGAAAACTGCCTATCGTGAATGAAGACGATGA
GCTGGTGGCAATCATTGCCCGCACCGACCTGAAGAAAATCGAGATTACC
CTCTGGCTAGTAAGGACGCAAAGAAACAGCTGCTGTGTGGAGCCGCTATT
GGCACACACGAGGACGATAAATATCGCCTGGATCTGCTGGCTCAGGCAGG
GGTGGACGTGGTCGTGCTGGATTCAAGCCAGGGAAACAGCATCTTCCAGA
TTAATATGATCAAGTACATTAAGGACAAGTACCCAAATCTGCAGGTCATC
GGAGGCAATGTCGTGACCGCAGCCCAGGCCAAAAACCTGATTGACGCAGG
AGTGGATGCTCTGAGGGTCGGAATGGGGAGTGGATCAATCTGCATCATTC
AGGAAGTGCTGGCCTGTGGACGACCTCAGGCAACTGCTGTCTACAAGGTG
TACGAGTATGCCCGGAGATTCGGAGTCCCAGTGATCGCTGACGGGGGAAT
TCAGAATGTGGGCCACATCGCAAAAGCCCTGGCTCTGGGGGCAAGCACAG

```
TGATGATGGGCAGCCTGCTGGCTGCAACCACAGAAGCCCCCGGCGAGTAC

TTCTTTAGTGATGGGTTCAGACTGAAGAAATATAGGGGCATGGGGTCACT

GGACGCCATGGATAAGCATCTGTCCTCTCAGAACAGGTATTTTTCCGAGG

CAGACAAGATCAAAGTCGCACAGGGCGTGTCTGGAGCTGTCCAGGATAAG

GGCAGTATTCACAAATTCGTGCCTTACCTGATCGCCGGAATTCAGCATTC

ATGCCAGGATATCGGCGCTAAGAGCCTGACACAGGTGCGGGCAATGATGT

ATTCCGGCGAACTGAAGTTCGAGAAAAGAACTTCTTCAGCCCAGGTCGAA

GGCGGCGTCCACTCACTGCACTCATACGAAAAGAGACTGTTCTAA

SEQ ID NO: 8 ASAH1 transgene
>hASAH1
ATGCCGGGCCGGAGTTGCGTCGCCTTAGTCCTCCTGGCTGCCGCCGTCAG

CTGTGCCGTCGCGCAGCACGCGCCGCCGTGGACGAGGACTGCAGAAAAT

CAACCTATCCTCCTTCAGGACCAACGTACAGAGGTGCAGTTCCATGGTAC

ACCATAAATCTTGACTTACCACCCTACAAAAGATGGCATGAATTGATGCT

TGACAAGGCACCAGTGCTAAAGGTTATAGTGAATTCTCTGAAGAATATGA

TAAATACATTCGTGCCAAGTGGAAAAATTATGCAGGTGGTGGATGAAAAA

TTGCCTGGCCTACTTGGCAACTTTCCTGGCCCTTTTGAAGAGGAAATGAA

GGGTATTGCCGCTGTTACTGATATACCTTTAGGAGAGATTATTTCATTCA

ATATTTTTTATGAATTATTTACCATTTGTACTTCAATAGTAGCAGAAGAC

AAAAAAGGTCATCTAATACATGGGAGAAACATGGATTTTGGAGTATTTCT

TGGGTGGAACATAAATAATGATACCTGGGTCATAACTGAGCAACTAAAAC

CTTTAACAGTGAATTTGGATTTCCAAAGAAACAACAAAACTGTCTTCAAG

GCTTCAAGCTTTGCTGGCTATGTGGGCATGTTAACAGGATTCAAACCAGG

ACTGTTCAGTCTTACACTGAATGAACGTTTCAGTATAAATGGTGGTTATC

TGGGTATTCTAGAATGGATTCTGGGAAAGAAAGATGTCATGTGGATAGGG

TTCCTCACTAGAACAGTTCTGGAAAATAGCACAAGTTATGAAGAAGCCAA

GAATTTATTGACCAAGACCAAGATATTGGCCCCAGCCTACTTTATCCTGG

GAGGCAACCAGTCTGGGGAAGGTTGTGTGATTACACGAGACAGAAAGGAA

TCATTGGATGTATATGAACTCGATGCTAAGCAGGGTAGATGGTATGTGGT

ACAAACAAATTATGACCGTTGGAAACATCCCTTCTTCCTTGATGATCGCA

GAACGCCTGCAAAGATGTGTCTGAACCGCACCAGCCAAGAGAATATCTCA

TTTGAAACCATGTATGATGTCCTGTCAACAAAACCTGTCCTCAACAAGCT

GACCGTATACACAACCTTGATAGATGTTACCAAAGGTCAATTCGAAACTT

ACCTGCGGGACTGCCCTGACCCTTGTATAGGTTGGTGA

SEQ ID NO: 9 (GAA transgene)
>co.hGAA
ATGGGCGTGAGGCACCCCCCTTGCTCTCACAGGCTGCTGGCCGTGTGCGC

ACTGGTGAGCCTGGCCACCGCCGCCCTGCTGGGCCACATCCTGCTGCACG

ACTTCCTGCTGGTGCCCAGGGAGCTGTCCGGCAGCTCCCCAGTGCTGGAG

GAGACCCACCCAGCACACCAGCAGGGCGCCCTCTCGGCCAGGCCCCCGCGA

TGCACAGGCACACCCAGGCCGGCCCCGCGCCGTGCCAACCCAGTGCGACG

TGCCACCCAACAGCCGGTTTGACTGTGCCCCCGATAAGGCCATCACACAG

GAGCAGTGCGAGGCCAGGGGCTGCTGTTATATCCCTGCAAAGCAGGGCCT

CCAGGGCGCCCAGATGGGACAGCCATGGTGTTTCTTTCCTCCATCTTACC

CCAGCTATAAGCTGGAGAATCTGTCTAGCTCCGAGATGGGCTACACAGCC

ACCCTGACAAGAACCACACCAACATTCTTTCCCAAGGACATCCTGACCCT

GCGGCTGGACGTGATGATGGAGACAGAGAACCGCCTGCACTTCACCATCA

AGGACCCCGCCAATAGGAGATATGAGGTGCCTCTGGAGACCCCACACGTG

CACTCTCGGGCCCCTAGCCCACTGTACTCCGTGGAGTTCTCTGAGGAGCC

ATTTGGCGTGATCGTGCGGCGCCAGCTGGATGGACGCGTGCTGCTGAACA

CCACAGTGGCCCCCCTGTTCTTTGCCGACCAGTTCCTCCAGCTGAGCACA

TCCCTGCCCTCCCAGTATATCACCGGCCTGGCCGAGCACCTGTCTCCTCT

GATGCTGTCTACCAGCTGGACAAGGATCACCCTGTGGAACAGAGACCTGG

CACCAACCCCTGGCGCAAATCTGTACGGCAGCCACCCTTTCTATCTGGCC

CTGGAGGATGGAGGCTCCGCCCACGGCGTGTTTCTGCTGAACTCTAATGC

CATGGACGTGGTGCTCCAGCCAAGCCCCGCCCTGTCCTGGCGGTCTACCG

GCGGCATCCTGGACGTGTACATCTTCCTGGGCCCTGAGCCAAAGTCCGTG

GTGCAGCAGTACCTGGACGTGGTGGGCTATCCTTTCATGCCCCCTTACTG

GGGACTGGGATTTCACCTGTGCCGCTGGGGCTATTCTAGCACAGCCATCA

CCCGGCAGGTGGTGGAGAACATGACCCGCGCCCACTTTCCACTGGATGTG

CAGTGGAATGACCTGGATTACATGGACTCCAGGAGAGACTTCACCTTCAA

CAAGGACGGCTTCAGGGATTTTCCCGCCATGGTGCAGGAGCTGCACCAGG

GCGGCCGGCGCTACATGATGATCGTGGACCCCGCCATCTCCTCTAGCGGA

CCTGCCGGCAGCTACAGACCATATGACGAGGGCCTGAGGAGAGGCGTGTT

CATCACAAACGAGACCGGCCAGCCTCTGATCGGCAAGGTCTGGCCAGGCT

CCACCGCCTTCCCAGACTTCACCAATCCAACCGCCCTGGCCTGGTGGGAG

GACATGGTGGCCGAGTTCCACGACCAGGTGCCTTTTGATGGCATGTGGAT

CGACATGAACGAGCCATCTAATTTCATCAGGGGCAGCGAGGACGGCTGCC

CCAACAATGAGCTGGAGAACCCACCATATGTGCCTGGCGTGGTGGGAGGC

ACCCTCCAGGCAGCAACCATCTGTGCCTCCTCTCACCAGTTCTGTCTAC

ACACTATAACCTGCACAATCTGTACGGACTGACCGAGGCAATCGCCAGCC

ACAGAGCCCTGGTGAAGGCCAGGGGCACAAGACCTTTCGTGATCTCCAGG

TCTACCTTTGCCGGACACGGCAGATACGCAGGACACTGGACCGGCGACGT

GTGGAGCAGCTGGGAGCAGCTGGCCTCTAGCGTGCCAGAGATCCTCCAGT

TCAACCTGCTGGGCGTGCCCCTGGTGGGAGCAGACGTGTGCGGCTTTCTG

GGCAATACATCCGAGGAGCTGTGCGTGAGGTGGACCCAGCTGGGAGCCTT

CTATCCCTTCATGCGCAACCACAATAGCCTGCTGTCCCTGCCTCAGGAGC

CATACAGCTTCTCCGAGCCTGCACAGCAGGCAATGAGGAAGGCCCTGACA

CTGCGCTATGCCCTGCTGCCACACCTGTACACCCTGTTTCACCAGGCACA

CGTGGCAGGAGAGACAGTGGCCCGGCCCCTGTTCCTGGAGTTTCCTAAGG

ATTCCTCTACCTGGACAGTGGACCACCAGCTGCTGTGGGGAGAGGCCCTG

CTGATCACCCCCGTGCTCCAGGCAGGCAAGGCAGAGGTGACAGGCTATTT

CCCTCTGGGCACATGGTACGACCTCCAGACCGTGCCAGTGGAGGCCCTGG

GCAGCCTGCCTCCACCACCTGCCGCCCCCCGCGAGCCTGCCATCCACTCC
```

-continued

GAGGGACAGTGGGTGACACTGCCAGCACCTCTGGACACCATCAACGTGCA

CCTGAGGGCCGGCTATATCATCCCCCTCCAGGGCCCTGGCCTGACCACAA

CCGAGTCCAGACAGCAGCCAATGGCCCTGGCCGTGGCCCTGACCAAGGGA

GGCGAGGCCAGGGGCGAGCTGTTCTGGGACGATGGCGAGTCTCTGGAGGT

GCTGGAGAGAGGCGCCTACACACAGGTCATCTTCCTGGCCAGGAACAATA

-continued

CAATCGTGAATGAGCTGGTGAGAGTGACCTCTGAGGGAGCAGGACTCCAG

CTCCAGAAGGTGACAGTGCTGGGAGTGGCAACCGCACCACAGCAGGTGCT

GAGCAACGGCGTGCCCGTGAGCAATTTCACATACTCCCCTGATACCAAGG

TGCTGGACATCTGCGTGAGCCTGCTGATGGGCGAGCAGTTTCTGGTGTCC

TGGTGTTGA

---

We claim:

1. A dual promoter lentivirus vector that expresses 1) a protein of interest, wherein the protein of interest is encoded by a transgene and wherein the protein of interest is associated with a lysosomal storage disorder and 2) a mutant form of inosine-5'-monophosphate dehydrogenase 2 (IMPDH2(IY)), wherein the lentivirus vector when transduced into a host cell confers resistance to mycophenolic acid (MPA) and/or mycophenolate mofetil (MMF) in vitro and/or in vivo and, wherein the mutant form of IMPDH2(IY) is encoded by the nucleotide sequence of SEQ ID NO: 7, or a sequence having at least 85% sequence identity to the nucleotide sequence of SEQ ID NO: 7.

2. The dual promoter lentivirus vector of claim 1, wherein the host cell is a hematopoietic cell.

3. The dual promoter lentivirus vector of claim 1, wherein a first promoter is hPGK promoter and a second promoter is EF1α promoter.

4. The dual promoter lentivirus vector of claim 1, wherein the protein of interest is α-galactosidase A and the lysosomal storage disorder is Fabry disease.

5. The dual promoter lentivirus vector of claim 4, wherein the α-galactosidase A is encoded by the transgene AGA comprising the nucleotide sequence of SEQ ID NO: 5 or a nucleotide sequence having 80% sequence identity to the nucleotide sequence of SEQ ID NO: 5.

6. The dual promoter lentivirus vector of claim 4, wherein the lentivirus vector is encoded by the nucleotide sequence of SEQ ID NO: 3 or a nucleotide sequence having 80% sequence identity to the nucleotide sequence of SEQ ID NO: 3.

7. The dual promoter lentivirus vector of claim 1, wherein the protein of interest is glucocerebrosidase (GBA protein).

8. The dual promoter lentivirus vector of claim 7, wherein the glucocerebrosidase is encoded by the transgene GBA comprising the nucleotide sequence of SEQ ID NO: 6 or a nucleotide sequence having 80% sequence identity to the nucleotide sequence of SEQ ID NO: 6.

9. The dual promoter lentivirus vector of claim 7, wherein the lentivirus vector is encoded by the nucleotide sequence of SEQ ID NO: 3 or a nucleotide sequence having 80% sequence identity to the nucleotide sequence of SEQ ID NO: 4.

10. The dual promoter lentivirus vector of claim 1, wherein the protein of is acid ceramidase (ASAH1).

11. The dual promoter lentivirus vector of claim 10, wherein the ASAH1 is encoded by the transgene comprising the nucleotide sequence of SEQ ID NO: 8 or a nucleotide sequence having 80% sequence identity to the nucleotide sequence of SEQ ID NO: 8.

12. The dual promoter lentivirus vector of claim 1, wherein the protein of interest is α-glucosidase (GAA).

13. The dual promoter lentivirus vector of claim 12, wherein the GAA is encoded by the transgene comprising the nucleotide sequence of SEQ ID NO: 9 or a nucleotide sequence having 80% sequence identity to the nucleotide sequence of SEQ ID NO: 9.

14. A host cell expressing the dual promoter lentivirus vector of claim 1.

15. The host cell of claim 14, wherein the host cell is a hematopoietic cell.

16. A method of treating a subject having a lysosomal storage disease (LSD) associated with a defect in a single protein, the method comprising the steps of:
   i) transducing hematopoietic stem cells (HSCs) obtained from a subject or a suitable donor in vitro or ex vivo with the dual promoter lentivirus vector of claim 1,
   ii) introducing the transduced HSCs into the subject to produce a population of lentivirus vector transduced HSCs engrafted in the subject, and
   (iii) administering to the subject an amount of mycrophenolate mofetil (MMF) sufficient to enrich the population of lentivirus vector transduced HSCs engrafted in the subject, wherein the method treats one or more symptoms of the lysosomal storage disease or disorder.

17. The method of claim 16, wherein the protein of interest is selected from the group consisting of α-galactosidase A, glucocerebrosidase (GBA protein), ASAH1, or GAA.

18. The method of claim 16, wherein the subject is in need of treatment for Fabry disease, and wherein the dual promoter lentivirus vector expresses α-galactosidase A and IMPDH2(IY) in the transduced HSCs, and wherein the method treats one or more symptoms of Fabry disease.

19. The method of claim 16, wherein the dual promoter lentiviral vector comprises the nucleotide sequence of SEQ ID NO: 3 or a nucleotide sequence having at least 80% sequence identity to the nucleotide sequence of SEQ ID NO: 3, wherein the lysosomal storage disease is Fabry disease.

20. The method of claim 16, wherein the dual promoter lentivirus vector expresses glucocerebrosidase and IMPDH2 (IY) in the transduced HSCs, and wherein the method treats one or more symptoms of Gaucher disease.

21. The method of claim 20, wherein the dual promoter lentivirus vector comprises the nucleotide sequence of SEQ ID NO: 4 or a nucleotide sequence having at least 80% sequence identity to the nucleotide sequence of SEQ ID NO: 4.

22. The method of claim 16, wherein the subject is in need of treatment for Fabry disease, and wherein the dual promoter lentivirus vector expresses ASAH1 and IMPDH2(IY) in the transduced HSCs, and wherein the method treats one or more symptoms of Farber disease.

23. The method of claim 16, wherein the subject is in need of treatment for Fabry disease, and wherein the dual promoter lentivirus vector expresses GAA and IMPDH2(IY) in the transduced HSCs, and wherein the method treats one or more symptoms of Pompe disease.

24. The method of claim 16, wherein the transduced HSCs are injected into the patient.

25. The method of claim 16, wherein the MMF is administered in an amount of 0.1-5 mg/kg three times a day.

26. The method of claim 16, wherein the MMF is administered at 5-10 mg/kg three times a day or 1000 mg twice a day.

* * * * *

UNITED STATES PATENT AND TRADEMARK OFFICE
CERTIFICATE OF CORRECTION

| | |
|---|---|
| PATENT NO. | : 11,597,917 B2 |
| APPLICATION NO. | : 16/619883 |
| DATED | : March 7, 2023 |
| INVENTOR(S) | : Jeffrey A. Medin et al. |

It is certified that error appears in the above-identified patent and that said Letters Patent is hereby corrected as shown below:

In the Specification

Column 13, Line 56, "andARSA" should be --and ARSA--.

Column 17, Line 5, "0.22 m" should be --0.22µm--.

Signed and Sealed this
Twenty-fifth Day of April, 2023

Katherine Kelly Vidal
*Director of the United States Patent and Trademark Office*